(12) United States Patent
Bodie et al.

(10) Patent No.: US 9,725,726 B2
(45) Date of Patent: *Aug. 8, 2017

(54) FILAMENTOUS FUNGI HAVING AN ALTERED VISCOSITY PHENOTYPE

(75) Inventors: Elizabeth A. Bodie, San Carlos, CA (US); Robert James Pratt, II, San Jose, CA (US)

(73) Assignee: DANISCO US INC CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/111,615

(22) PCT Filed: Apr. 20, 2012

(86) PCT No.: PCT/US2012/034379
§ 371 (c)(1),
(2), (4) Date: Dec. 20, 2013

(87) PCT Pub. No.: WO2012/145584
PCT Pub. Date: Oct. 26, 2012

(65) Prior Publication Data
US 2014/0099721 A1    Apr. 10, 2014

Related U.S. Application Data

(60) Provisional application No. 61/478,162, filed on Apr. 22, 2011, provisional application No. 61/478,160, filed on Apr. 22, 2011.

(51) Int. Cl.
*C12N 15/80* (2006.01)
*C12N 1/36* (2006.01)
*C12R 1/645* (2006.01)
*C12N 9/12* (2006.01)

(52) U.S. Cl.
CPC ............. *C12N 15/80* (2013.01); *C12N 1/36* (2013.01); *C12N 9/1241* (2013.01); *C12Y 207/07013* (2013.01)

(58) Field of Classification Search
None
See application file for complete search history.

(56) References Cited

U.S. PATENT DOCUMENTS

| | | | |
|---|---|---|---|
| 2005/0042738 A1* | 2/2005 | Swarnakar et al. | 435/183 |
| 2014/0094587 A1* | 4/2014 | Bodie | C12N 1/36 530/350 |
| 2014/0127817 A1* | 5/2014 | Bodie et al. | 435/471 |
| 2014/0220689 A1* | 8/2014 | Bodie et al. | 435/440 |
| 2014/0315313 A1* | 10/2014 | Bodie | C12N 1/14 435/471 |

FOREIGN PATENT DOCUMENTS

WO    WO 2001/09352    2/2001

OTHER PUBLICATIONS

Talbot et al. 1993 (Identification and Characterization of MPG1, a gene involved in pathogenicity from the Rice Blast Fungus Magnaporthe grisea; The Plant Cell 5:1575-1590).*
Kruszewska et al. 1998 (Isolation of a Trichoderma reesei cDNA encoding GTP: a-D-mannose-1-phospate guanyltranserase involved in early steps of protein glycosylation; Curr Genet 33:445-450).*
Zakrzewska et al. 2003 (Overexpression of the gene encoding GTP: Mannose-1-Phosphate Guanyltransferase, mpg1, increases cellular GDP-mannose levels and protein mannosylation in Trichodema reesi; Applied and Environmental Microbiology, 69(8):4383-4389).*
Carris et al. 2012 (Introduction to Fungi. The Plant Health Instructor. DOI:10.1094/PHI-I-2012-0426-01).*
Eyre-Walker et al. 2007 (The distribution of fitness effects of new mutations; Nature Review/Genetics vol. 8:610-618).*
Caracuel, et al., "Fusarium oxysporum gas1 encodes a putative β-1,3-Glucanosyltransferase required for virulence on tomato plants", Molecular Plant-Microbe Interactions, vol. 18, No. 11, pp. 1140-1147, (2005).
Dai, et al., "Identification of genes associated with morphology in Aspergillus niger by using suppression subtractive hybridization", Applied and Environmental Microbiology, vol. 70, No. 4, pp. 2474-2485, (2004).
Garcia, et al., "The global transcriptional response to transient cell wall damage in *Saccharomyces cerevisiae* and its regulation by the cell integrity signaling pathway", The Journal of Biological Chemistry, vol. 279, No. 15, pp. 15183-15195, (2004).
Hajdukiewicz, et al., "The small, versatile pPZP family of Agrobacterium binary vectors for plant transformation", Plant Molecular Biology, 25: 989-994, (1994).
Hood, et al., "New Agrobacterium helper plasmids for gene transfer to plants", Transgenic Research 2, pp. 208-218, (1993).
Hughes, et al., "Assembly, organization, and function of the COPII coat", Histochem Cell Biol., 129: pp. 129-151, (2008).
Karababa, et al., "CRZ1, a target of the calcineurin pathway in Candida albicans", Molecular Microbiology, 59(5), pp. 1429-1451, (2006).
Karhinen, et al., "Endoplasmic reticulum exit of a secretory Glycoprotein in the absence of Sec24p family proteins in yeast", Traffic, 6: pp. 562-574, (2005).
Kothe, et al., "Calcineurin subunit B is required for normal vegetative growth in neurospora crassa", Fungal Genetics and Biology, 23, pp. 248-258, (1998).
Kruszewska, et al., "Isolation of a Trichoderma reesei cDNA encoding Gtp: a-D-mannose-1-phosphate guanyltransferase involved in early steps of protein glycosylation", Curr. Genet., 33: 445-450, (1998).

(Continued)

*Primary Examiner* — Gary Nickol
*Assistant Examiner* — Mary Lyons

(57) ABSTRACT

Described are compositions and methods relating to variant filamentous fungi having altered growth characteristics. Such variants are well-suited for growth in submerged cultures, e.g., for the large-scale production of enzymes and other proteins for commercial applications.

16 Claims, 3 Drawing Sheets

(56) References Cited

OTHER PUBLICATIONS

Lagorce, et al., "Genome-wide analysis of the response to cell wall mutations in the yeast *Saccharomyces cerevisiae*", The Journal of Biological Chemistry, vol. 278, No. 22, pp. 20345-20357. (2003).
Mouyna, et al., "Deletion of GEL2 encoding for a β(1-3)glucanosyltransferase affects morphogenesis and virulence in Aspergillus fumigatus", Molecular Microbiology, 56(6), pp. 1675-1688, (2005).
Munro, el al., "The PKC, HOG and $Ca^{2+}$ signaling pathways co-ordinately regulate chitin synthesis in Candida albicans", Molecular Microbiology, 63(5), pp. 1399-1413, (2007).
Pardini, et al., "The CRH family coding for cell wall Glycosylphosphatidyylinositol proteins with a predicted transglycosidase domain affects cell wall organization and virulence of Candida albicans", The Journal of Biological Chemistry, vol. 281, No. 52, pp. 40399-40411, (2006).
Passolunghi, el al., "Cloning of the Zygosaccharomyces bailii GAS1 homologue and effect of cell wall engineering on protein secretory phenotype", Microbial Cell Factories, 9: 7, pp. 1-11, (2010).
Peng, el al.. "Evidence for overlapping and distinct functions in protein transport of coat protein Sec24p family members", The Journal of Biological Chemistry, vol. 275, No. 15, pp. 11521-11528, (2000).
Perlinska-Lenart, et al., "Glycoprotein Hupersecretion alters the cell wall in Trichoderma reesei strains expressing the saccharomyces cerevisiae dolichylphosphate Mannose synthase gene". Applied and Environmental Microbiology, vol. 72, No. 123, pp. 7778-7784, (2006).
Popolo, et al., "Disulfide bond structure and domain organization of yeast β(1,3)-Glucanosyltransferases involved in cell wall biogenesis", The Journal of Biological Chemistry, vol. 283, No. 27, pp. 18553-18565, (2008).
Prokisch, et al., "Impairment of calcineurin function in Neurospora crassa reveals its essential role in hyphal growth, morphology and maintenance of the apical $Ca^+$ gradient", Mol. Gen. Genet., 256: 104-114, (1997).
Roberg, et al., "LST1 is a SEC24 homologue used for selective export of the plasma membrane ATPase from the endoplasmic reticulum", The Journal of Cell Biology, vol. 145, No. 4, pp. 659-672, (1999).
Schirawski, et al., "Endoplasmic reticulum glucosidase II is required for pathogenicity of Ustilago maydis", The Plant Cell, vol. 17, pp. 3532-3543, (2005).
Shimoni, et al., "Lst1p and Sec24p cooperate in sorting of the plasma membrane ATPase into COPII vesicles in *Saccharomyces cerevisiae*", The Journal of Cell Biology, vol. 151, No. 5, pp. 973-984, (1999).
Simola, et al., "Trehalose is required for conformational repair of heat-denatured proteins in the yeast endoplasmic reticulum but not for maintenance of membrane traffic functions after severe heat stress", Molecular Microbiology, 37(1), pp. 42-53, (2000).
Singer, et al., "Multiple effects of Trehalose on protein folding in vitro and in vivo", Molecular Cell, vol. 1, pp. 639-648, (1998).
Turchini, et al., "Increase of external osmolarity reduces morphogenetic defects and accumulation of Chitin in a gas1 mutant of *Saccharomyces cerevisiae*", Journal of Bacteriology, vol. 182, No. 4, pp. 1167-1171, (2000).
Yamazaki, et al.. "A chitinase gene, chiB, involve in the autolytic process of Aspergillus nidulans", Current Genetics, vol. 51, No. 2, pp. 89-98, (2006).
Yoshimoto, et al., "Genome-wide analysis of gene expression regulated by the Calcineurin/Crz1p signaling pathway in *Saccharomyces cerevisiae*", The Journal of Biological Chemistry, vol. 277, No. 34, pp. 31079-31088, (2002).
Zakrzewska, et al., "Overexpression of the gene encoding GTP: mannose-1-phosphate guanytransferase, mpg1, increases cellular GDP-mannose levels and protein mannosylation in Trichoderm reesei", Applied and Environmental Microbiology, vol. 69, No. 8, pp. 4383-4389, (2003).

\* cited by examiner

SEQUENCE LISTING

<160> NUMBER OF SEQ ID NOS: 38

<210> SEQ ID NO 1
<211> LENGTH: 364
<212> TYPE: PRT
<213> ORGANISM: Trichoderma reesei

<400> SEQUENCE: 1

```
Met Lys Gly Leu Ile Leu Val Gly Gly Phe Gly Thr Arg Leu Arg Pro
1               5                   10                  15

Leu Thr Leu Thr Leu Pro Lys Pro Leu Val Glu Phe Cys Asn Lys Pro
                20                  25                  30

Met Ile Val His Gln Ile Glu Ala Leu Val Ala Ala Gly Val Thr Asp
            35                  40                  45

Ile Val Leu Ala Val Asn Tyr Arg Pro Glu Ile Met Glu Lys Phe Leu
    50                  55                  60

Ala Glu Tyr Glu Glu Lys Tyr Asn Ile Asn Ile Glu Phe Ser Val Glu
65                  70                  75                  80

Ser Glu Pro Leu Asp Thr Ala Gly Pro Leu Lys Leu Ala Glu Arg Ile
                85                  90                  95

Leu Gly Lys Asp Asp Ser Pro Phe Phe Val Leu Asn Ser Asp Val Ile
            100                 105                 110

Cys Asp Tyr Pro Phe Lys Glu Leu Leu Glu Phe His Lys Ala His Gly
        115                 120                 125

Asp Glu Gly Thr Ile Val Val Thr Lys Val Glu Glu Pro Ser Lys Tyr
    130                 135                 140

Gly Val Val Val His Lys Pro Asn His Pro Ser Arg Ile Asp Arg Phe
145                 150                 155                 160

Val Glu Lys Pro Val Glu Phe Val Gly Asn Arg Ile Asn Ala Gly Met
                165                 170                 175

Tyr Ile Phe Asn Pro Ser Val Leu Lys Arg Ile Glu Leu Arg Pro Thr
            180                 185                 190

Ser Ile Glu Lys Glu Thr Phe Pro Ala Met Val Ala Asp Asn Gln Leu
        195                 200                 205

His Ser Phe Asp Leu Glu Gly Phe Trp Met Asp Val Gly Gln Pro Lys
    210                 215                 220

Asp Phe Leu Ser Gly Thr Cys Leu Tyr Leu Ser Ser Leu Thr Lys Lys
225                 230                 235                 240

Gly Ser Lys Glu Leu Thr Pro Pro Thr Glu Pro Tyr Val His Gly Gly
                245                 250                 255

Asn Val Met Ile His Pro Ser Ala Lys Ile Gly Lys Asn Cys Arg Ile
            260                 265                 270

Gly Pro Asn Val Thr Ile Gly Pro Asp Val Val Gly Asp Gly Val
        275                 280                 285

Arg Leu Gln Arg Cys Val Leu Leu Lys Gly Ser Lys Val Lys Asp His
    290                 295                 300

Ala Trp Val Lys Ser Thr Ile Val Gly Trp Asn Ser Thr Val Gly Arg
305                 310                 315                 320

Trp Ala Arg Leu Glu Asn Val Thr Val Leu Gly Asp Asp Val Thr Ile
                325                 330                 335

Gly Asp Glu Ile Tyr Val Asn Gly Gly Ser Val Leu Pro His Lys Ser
```

```
                    340             345             350
Ile Lys Ala Asn Val Asp Val Pro Ala Ile Ile Met
            355                 360

<210> SEQ ID NO 2
<211> LENGTH: 364
<212> TYPE: PRT
<213> ORGANISM: Neurospora crassa

<400> SEQUENCE: 2

Met Lys Ala Leu Ile Leu Val Gly Gly Phe Gly Thr Arg Leu Arg Pro
1               5                   10                  15

Leu Thr Leu Thr Met Pro Lys Pro Leu Val Glu Phe Gly Asn Lys Arg
                20                  25                  30

Met Ile Leu His Gln Ile Glu Ala Leu Ala Ala Ala Gly Val Thr Asp
            35                  40                  45

Ile Val Leu Ala Val Asn Tyr Arg Pro Glu Ile Met Glu Lys Tyr Leu
        50                  55                  60

Ala Glu Tyr Glu Lys Gln Phe Gly Ile Asn Ile Thr Ile Ser Ile Glu
65                  70                  75                  80

Ser Glu Pro Leu Gly Thr Ala Gly Pro Leu Lys Leu Ala Glu Asp Val
                85                  90                  95

Leu Arg Lys Asp Asp Thr Pro Phe Phe Val Leu Asn Ser Asp Val Thr
            100                 105                 110

Cys Glu Tyr Pro Phe Lys Glu Leu Ala Ala Phe His Lys Ala His Gly
        115                 120                 125

Asp Glu Gly Thr Ile Val Val Thr Lys Val Glu Pro Ser Lys Tyr
130                 135                 140

Gly Val Val Val His Lys Pro Asn His Pro Ser Arg Ile Asp Arg Phe
145                 150                 155                 160

Val Glu Lys Pro Val Gln Phe Val Gly Asn Arg Ile Asn Ala Gly Leu
                165                 170                 175

Tyr Ile Phe Asn Pro Ser Val Ile Asp Arg Val Glu Leu Arg Pro Thr
            180                 185                 190

Ser Ile Glu Gln Glu Thr Phe Pro Ala Met Val Arg Asp Gly Gln Leu
        195                 200                 205

His Ser Phe Asp Leu Glu Gly Phe Trp Met Asp Ile Gly Gln Pro Lys
210                 215                 220

Asp Phe Leu Thr Gly Thr Cys Leu Tyr Leu Ser Ser Leu Thr Lys Lys
225                 230                 235                 240

Gly Ser Lys Glu Leu Ala Pro Thr Thr Leu Pro Tyr Ile His Gly Gly
                245                 250                 255

Asn Val Leu Ile Asp Pro Ser Ala Lys Ile Gly Lys Asn Cys Arg Ile
            260                 265                 270

Gly Pro Asn Val Thr Ile Gly Pro Asn Val Val Gly Asp Gly Val
        275                 280                 285

Arg Leu Gln Arg Cys Val Leu Leu Glu Gly Ser Lys Val Lys Asp His
290                 295                 300

Ala Trp Val Lys Ser Thr Ile Val Gly Trp Asn Ser Thr Val Gly Lys
305                 310                 315                 320

Trp Ala Arg Leu Glu Asn Val Thr Val Leu Gly Asp Asp Val Thr Ile
                325                 330                 335

Gly Asp Glu Ile Tyr Val Asn Gly Gly Ser Ile Leu Pro His Lys Thr
            340                 345                 350
```

```
Ile Lys Ala Asn Val Asp Val Pro Ala Ile Ile Met
            355                 360
```

```
<210> SEQ ID NO 3
<211> LENGTH: 479
<212> TYPE: PRT
<213> ORGANISM: Aspergillus oryzae

<400> SEQUENCE: 3
```

```
Met Lys Gly Val Gly Gly Gly Thr Arg Arg Thr Thr Lys Val Cys Asn
1               5                   10                  15

Lys Met Val His Ala Val Ala Ala Gly Val Thr Asp Val Ala Val Asn
            20                  25                  30

Tyr Arg Met Lys Ala Tyr Lys Met Lys Ala Val Gly Gly Gly Thr Arg
        35                  40                  45

Arg Thr Thr Lys Val Gly Asn Arg Met His Val Ser Ala Ala Ala Gly
    50                  55                  60

Val Thr Asp Val Ala Val Asn Tyr Arg Asp Val Met Val Ser Ala Lys
65                  70                  75                  80

Lys Tyr Tyr Asn Asn Ser Val Ser Asp Thr Ala Gly Lys Ala Arg Gly
                85                  90                  95

Lys Asp Asp Ser Val Asn Ser Asp Val Cys Asp Tyr Lys His Lys Ala
            100                 105                 110

His Gly Asp Gly Thr Val Val Thr Lys Val Tyr Asn Val Lys Ser Val
        115                 120                 125

Ser Gly Thr Ala Gly Lys Ala Lys Gly Lys Asp Asp Ser Val Asn Ser
    130                 135                 140

Asp Val Cys Asp Tyr Lys Ala His Lys Lys His Gly Asp Gly Thr Val
145                 150                 155                 160

Val Thr Lys Val Asp Ser Lys Tyr Gly Val Val His Lys Asn His
                165                 170                 175

Ser Arg Asp Arg Val Lys Val Val Gly Asn Arg Asn Ala Gly Met Tyr
            180                 185                 190

Asn Ser Val Lys Arg Arg Thr Ser Lys Thr Ala Met Val Ala Asp Asn
        195                 200                 205

His Ser Ser Lys Tyr Gly Val Val His Lys Asn His Ser Arg Asp
    210                 215                 220

Arg Val Lys Val Val Gly Asn Arg Asn Ala Gly Tyr Met Asn Ser Val
225                 230                 235                 240

Asn Arg Arg Thr Ser Thr Ala Cys Lys Asp Gly His Ser Asp Gly Trp
                245                 250                 255

Met Asp Val Gly Lys Asp Ser Gly Thr Cys Tyr Ser Ser Thr Lys Lys
            260                 265                 270

Gly Ser Lys Thr Thr Tyr Val His Gly Gly Asn Val Met His Ser Ala
        275                 280                 285

Lys Gly Lys Asn Cys Arg Gly Asn Val Thr Gly Asp Gly Trp Met Asp
    290                 295                 300

Val Gly Lys Asp Ser Gly Thr Cys Tyr Thr Ser Ala Lys Arg Asn Ser
305                 310                 315                 320

Lys Ala Asn Ser Tyr Val Tyr Gly Gly Asn Val Met Val Asp Ser Ala
                325                 330                 335

Lys Gly Lys Asn Cys Arg Gly Asn Val Val Gly Asp Val Val Gly
            340                 345                 350

Asp Gly Val Arg Arg Cys Val Lys Gly Ser Lys Val Lys Asp His Ala
        355                 360                 365
```

-continued

Trp Val Lys Ser Thr Val Gly Trp Asn Ser Thr Val Gly Arg Trp Ala
370             375                 380

Arg Asn Val Thr Val Gly Asp Asp Val Thr Gly Asp Tyr Val Asn Gly
385                 390                 395                 400

Gly Ser Val His Asn Val Val Gly Asp Gly Val Arg Arg Cys Val
            405                 410                 415

Asn Ser Lys Val Lys Asp His Ala Trp Val Lys Ser Thr Val Gly Trp
            420                 425                 430

Asn Ser Ser Val Gly Arg Trp Ala Arg Asn Val Thr Val Gly Asp Asp
            435                 440                 445

Val Thr Ala Asp Val Tyr Val Asn Gly Gly Ser His Lys Ser Lys Ala
450                 455                 460

Asn Val Asp Val Ala Met Lys Ser Lys Asn Val Asp Val Ala Met
465                 470                 475

<210> SEQ ID NO 4
<211> LENGTH: 532
<212> TYPE: PRT
<213> ORGANISM: Trichoderma atroviride

<400> SEQUENCE: 4

Met Asp Gly Met Met Ser Gln Ala Met Gly Gln Gln Ala Phe Tyr Phe
1               5                   10                  15

Tyr Asn His Asn His Asp His Lys Met Ala Arg Gln Ala Ile Phe Ala
                20                  25                  30

Gln Gln Met Ala Ala Tyr Gln Met Val Pro Thr Leu Pro Pro Thr Pro
            35                  40                  45

Met Tyr Ser Arg Pro Asn Ser Ser Cys Ser Gln Pro Pro Thr Leu Tyr
        50                  55                  60

Ser Asn Gly Pro Ser Val Met Thr Pro Thr Ser Thr Pro Pro Leu Ser
65                  70                  75                  80

Arg Lys His Met Met Leu Asp Ala Glu Phe Gly Asp Asn Pro Tyr Phe
                85                  90                  95

Pro Ser Thr Pro Pro Leu Ser Thr Ser Gly Ser Thr Val Gly Ser Pro
            100                 105                 110

Lys Ala Cys Asp Met Leu Gln Thr Pro Met Asn Pro Met Phe Ser Gly
        115                 120                 125

Leu Glu Gly Ile Ala Met Lys Glu Ala Val Asp Thr Thr Glu Ser Leu
130                 135                 140

Val Val Asp Trp Ala Ser Ile Val Ser Pro Leu Ser Pro Val Tyr
145                 150                 155                 160

Phe Gln Ser Gln Val Ser Arg Val Pro Ser Pro Thr Ser Ser Pro Ser
                165                 170                 175

Asp Ile Leu Ser Thr Ala Ser Cys Pro Ser Leu Ser Pro Ser Pro Thr
            180                 185                 190

Pro Tyr Ala Arg Ser Val Thr Ser Glu His Asp Val Asp Phe Cys Asp
        195                 200                 205

Pro Arg Asn Leu Thr Val Ser Val Gly Ser Asn Pro Thr Leu Ala Pro
210                 215                 220

Glu Phe Thr Leu Thr Gly Leu Ala Glu Asp Leu Lys Gly Glu Gln Leu
225                 230                 235                 240

Ser Thr Ala Gln His Thr Phe Asp Phe Asn Pro Ala Leu Pro Ser Gly
                245                 250                 255

Leu Pro Thr Phe Glu Asp Phe Ser Asp Leu Glu Ser Glu Ala Asp Phe

```
                    260                 265                 270
Ser Asn Leu Val Asn Leu Gly Glu Val Asn Pro Ile Asp Ile Ser Arg
                275                 280                 285

Pro Arg Ala Cys Thr Gly Ser Ser Val Val Ser Leu Gly His Gly Ser
            290                 295                 300

Phe Ile Gly Asp Glu Glu Leu Ser Phe Glu Asp Asn Asp Ala Phe Gly
305                 310                 315                 320

Phe Asn Ser Leu Pro Ser Pro Thr Ser Ser Ile Asp Phe Ser Asp Val
                325                 330                 335

His Gln Asp Lys Arg Arg Lys Lys Glu Lys Lys Asp Ile Lys Pro Ile
            340                 345                 350

Met Asn Thr Ala Ala Ser Gly Ser Pro Ser Gly Asn Glu Gln Ile Gly
                355                 360                 365

Ala Thr Pro Ala Ala Ser Ala Ala Ser Asp Ser Asn Ala Ser Ser Ala
            370                 375                 380

Ser Glu Asp Pro Ser Ser Met Pro Ala Pro Thr Asn Arg Arg Gly Arg
385                 390                 395                 400

Lys Gln Ser Leu Thr Glu Asp Pro Ser Lys Thr Phe Val Cys Asp Leu
                405                 410                 415

Cys Asn Arg Arg Phe Arg Arg Gln Glu His Leu Lys Arg His His Tyr Arg
            420                 425                 430

Ser Leu His Thr Gln Glu Lys Pro Phe Glu Cys Asn Glu Cys Gly Lys
                435                 440                 445

Lys Phe Ser Arg Ser Asp Asn Leu Ala Gln His Ala Arg Thr His Ala
            450                 455                 460

Gly Gly Ala Ile Val Met Asn Leu Ile Glu Asp Gly Ser Glu Val Pro
465                 470                 475                 480

Ala Phe Asp Gly Ser Met Met Thr Gly Pro Val Gly Asp Tyr Asn
                485                 490                 495

Thr Tyr Gly Lys Val Leu Phe Gln Ile Ala Ser Glu Ile Pro Gly Ser
            500                 505                 510

Ala Ser Glu Leu Ser Ser Glu Glu Gly Asp Gln Ser Lys Lys Lys Arg
                515                 520                 525

Lys Arg Ser Asp
        530

<210> SEQ ID NO 5
<211> LENGTH: 534
<212> TYPE: PRT
<213> ORGANISM: Trichoderma reesei

<400> SEQUENCE: 5

Met Asp Gly Met Met Ser Gln Pro Met Gly Gln Gln Ala Phe Tyr Phe
1               5                   10                  15

Tyr Asn His Glu His Lys Met Ser Pro Arg Gln Val Ile Phe Ala Gln
                20                  25                  30

Gln Met Ala Ala Tyr Gln Met Met Pro Ser Leu Pro Pro Thr Pro Met
            35                  40                  45

Tyr Ser Arg Pro Asn Ser Ser Cys Ser Gln Pro Pro Thr Leu Tyr Ser
        50                  55                  60

Asn Gly Pro Ser Val Met Thr Pro Thr Ser Thr Pro Pro Leu Ser Ser
65                  70                  75                  80

Arg Lys Pro Met Leu Val Asp Thr Glu Phe Gly Asp Asn Pro Tyr Phe
                85                  90                  95
```

```
Pro Ser Thr Pro Pro Leu Ser Ala Ser Gly Ser Thr Val Gly Ser Pro
            100                 105                 110

Lys Ala Cys Asp Met Leu Gln Thr Pro Met Asn Pro Met Phe Ser Gly
        115                 120                 125

Leu Glu Gly Ile Ala Ile Lys Asp Ser Ile Asp Ala Thr Glu Ser Leu
    130                 135                 140

Val Leu Asp Trp Ala Ser Ile Ala Ser Pro Pro Leu Ser Pro Val Tyr
145                 150                 155                 160

Leu Gln Ser Gln Thr Ser Ser Gly Lys Val Pro Ser Leu Thr Ser Ser
                165                 170                 175

Pro Ser Asp Met Leu Ser Thr Thr Ala Ser Cys Pro Ser Leu Ser Pro
            180                 185                 190

Ser Pro Thr Pro Tyr Ala Arg Ser Val Thr Ser Glu His Asp Val Asp
        195                 200                 205

Phe Cys Asp Pro Arg Asn Leu Thr Val Ser Val Gly Ser Asn Pro Thr
    210                 215                 220

Leu Ala Pro Glu Phe Thr Leu Leu Ala Asp Asp Ile Lys Gly Glu Pro
225                 230                 235                 240

Leu Pro Thr Ala Ala Gln Pro Ser Phe Asp Phe Asn Pro Ala Leu Pro
                245                 250                 255

Ser Gly Leu Pro Thr Phe Glu Asp Phe Ser Asp Leu Glu Ser Glu Ala
            260                 265                 270

Asp Phe Ser Ser Leu Val Asn Leu Gly Glu Ile Asn Pro Val Asp Ile
        275                 280                 285

Ser Arg Pro Arg Ala Cys Thr Gly Ser Ser Val Val Ser Leu Gly His
    290                 295                 300

Gly Ser Phe Ile Gly Asp Glu Asp Leu Ser Phe Asp Asp Glu Ala Phe
305                 310                 315                 320

His Phe Pro Ser Leu Pro Ser Pro Thr Ser Ser Val Asp Phe Cys Asp
                325                 330                 335

Val His Gln Asp Lys Arg Gln Lys Lys Asp Arg Lys Glu Ala Lys Pro
            340                 345                 350

Val Met Asn Ser Ala Ala Gly Gly Ser Gln Ser Gly Asn Glu Gln Ala
        355                 360                 365

Gly Ala Thr Glu Ala Ala Ser Ala Ala Ser Asp Ser Asn Ala Ser Ser
    370                 375                 380

Ala Ser Asp Glu Pro Ser Ser Met Pro Ala Pro Thr Asn Arg Arg
385                 390                 395                 400

Gly Arg Lys Gln Ser Leu Thr Glu Asp Pro Ser Lys Thr Phe Val Cys
                405                 410                 415

Asp Leu Cys Asn Arg Arg Phe Arg Arg Gln Glu His Leu Lys Arg His
            420                 425                 430

Tyr Arg Ser Leu His Thr Gln Glu Lys Pro Phe Glu Cys Asn Glu Cys
        435                 440                 445

Gly Lys Lys Phe Ser Arg Ser Asp Asn Leu Ala Gln His Ala Arg Thr
    450                 455                 460

His Ser Gly Gly Ala Ile Val Met Asn Leu Ile Glu Glu Ser Ser Glu
465                 470                 475                 480

Val Pro Ala Tyr Asp Gly Ser Met Met Ala Gly Pro Val Gly Asp Asp
                485                 490                 495

Tyr Ser Thr Tyr Gly Lys Val Leu Phe Gln Ile Ala Ser Glu Ile Pro
            500                 505                 510

Gly Ser Ala Ser Glu Leu Ser Ser Glu Glu Gly Glu Gln Gly Lys Lys
```

```
                515                 520                 525
Lys Arg Lys Arg Ser Asp
    530

<210> SEQ ID NO 6
<211> LENGTH: 622
<212> TYPE: PRT
<213> ORGANISM: Aspergillus clavatus

<400> SEQUENCE: 6

Met Asp Thr Thr Tyr Thr Met Val Gly Thr Pro Val Gln Gly Gln Pro
1               5                   10                  15

Ser Phe Ala Tyr Tyr Thr Thr Asn Asp Ser Gln Ser Arg Gln Gln His
            20                  25                  30

Phe Thr Ser His Pro Ser Glu Met Gln Ala Phe Tyr Gly Gln Met Gln
        35                  40                  45

Pro Tyr Pro Gln Gln Gln Gln Thr Cys Met Pro Asp Gln Gln Ser
    50                  55                  60

Ile Tyr Ala Ala Gln Pro Met Leu Asn Met His Gln Met Ala Thr Ala
65                  70                  75                  80

Asn Ala Phe Arg Gly Ala Leu Ser Met Thr Pro Ile Val Ser Pro Gln
                85                  90                  95

Pro Thr His Leu Lys Pro Thr Ile Ile Val Gln Gln Asp Ser Pro Met
            100                 105                 110

Leu Met Pro Leu Asp Thr Arg Phe Val Ser Ser Asp Tyr Tyr Ala Phe
        115                 120                 125

Pro Ser Thr Pro Pro Leu Ser Thr Ser Gly Ser Thr Ile Ser Ser Pro
    130                 135                 140

Pro Ser Ser Gly Arg Ser Leu His Thr Pro Ile Asn Asp Cys Phe Phe
145                 150                 155                 160

Ser Phe Glu Lys Val Glu Gly Val Lys Glu Gly Cys Glu Ser Asp Val
                165                 170                 175

His Ser Glu Leu Leu Ala Asn Ala Asp Trp Ser Arg Ser Asp Ser Pro
            180                 185                 190

Pro Leu Thr Pro Val Phe Ile His Pro Pro Ser Leu Thr Ala Ser Gln
        195                 200                 205

Ser Ser Asp Leu Leu Ser Ala His Ser Ser Cys Pro Ser Leu Ser Pro
    210                 215                 220

Ser Pro Ser Pro Val Ser Ser Thr Phe Ile Ala Pro Pro His Ser Gly
225                 230                 235                 240

Leu Ser Val Glu Pro Ser Gly Thr Asp Phe Cys Asp Pro Arg Gln Leu
                245                 250                 255

Thr Val Glu Ser Ser Val Asp Ser Ser Thr Glu Leu Pro Pro Leu Pro
            260                 265                 270

Thr Leu Ser Cys Asn Glu Glu Glu Pro Lys Val Val Leu Gly Ser Ala
        275                 280                 285

Thr Val Thr Leu Pro Val His Glu Ser Leu Ser Pro Ala Tyr Thr Ser
    290                 295                 300

Ser Thr Glu Asp Pro Leu Gly Ser Leu Pro Thr Phe Asp Ser Phe Thr
305                 310                 315                 320

Asp Leu Asp Ser Glu Asp Glu Phe Val Asn Asn Leu Val Asp Phe His
                325                 330                 335

Pro Gly Gly Asn Pro Tyr Phe Leu Gly Asp Lys Arg Gln Arg Leu Gly
            340                 345                 350
```

```
Ser Tyr Leu Leu Glu Glu Asp Glu Phe Leu Ser Asp Arg Ser Phe Asp
        355                 360                 365

Asp Leu Asp Asp His Glu Ala Phe Ala His Ser Gly Leu Pro Ser Leu
    370                 375                 380

Glu Pro Ser Glu Leu Ile Ser Val Gln Gly Asp Val Ala Glu Val Ser
385                 390                 395                 400

Glu Glu Met Arg Ser Lys Lys Arg Thr Thr Ser Arg Arg Thr Leu Lys
                405                 410                 415

Arg Thr Asn Ser Ser Asp Ser Ser Glu Ser Leu Ala Thr Ser Gly
                420                 425                 430

Lys Arg Thr Gln Ala Ser Ala Asn Gly Arg Ser Gly His Ser Glu Ala
            435                 440                 445

Thr Ser Ser Ser Ala Gln Gln Ser Thr Thr Pro Ser Arg Gln Asn Ser
        450                 455                 460

Thr Ala Asn Ala Ser Ser Ser Glu Ala Pro Ser Ala Pro Val Ser
465                 470                 475                 480

Val Asn Arg Arg Gly Arg Lys Gln Ser Leu Thr Asp Asp Pro Ser Lys
                485                 490                 495

Thr Phe Val Cys Thr Leu Cys Ser Arg Arg Phe Arg Arg Gln Glu His
            500                 505                 510

Leu Lys Arg His Tyr Arg Ser Leu His Thr Gln Asp Lys Pro Phe Glu
        515                 520                 525

Cys His Glu Cys Gly Lys Lys Phe Ser Arg Ser Asp Asn Leu Ala Gln
    530                 535                 540

His Ala Arg Thr His Gly Gly Ser Ile Val Met Gly Val Ile Asp
545                 550                 555                 560

Thr Asn Ala Ser Leu Gln Ala Ser Tyr Glu Glu Arg Glu Pro Arg Leu
                565                 570                 575

Leu Gly Ala Ala Leu Tyr Glu Ala Ala Asn Ala Ala Ala Asn Lys Ser
            580                 585                 590

Thr Thr Ser Asp Ser Ser Asp Gly Thr Ile Ser Asp Thr Ser Ser Val
        595                 600                 605

Glu Gly Arg Pro Ile Lys Lys Arg Arg Arg Glu Asp His Ala
    610                 615                 620

<210> SEQ ID NO 7
<211> LENGTH: 618
<212> TYPE: PRT
<213> ORGANISM: Aspergillus fumigatus

<400> SEQUENCE: 7

Met Asp Ala Thr Tyr Thr Met Ala Gln Thr Pro Val Gln Gly Gln Pro
1               5                   10                  15

Ser Phe Ala Tyr Tyr Pro Thr Glu Ser Gln Ser Arg Gln His Phe
                20                  25                  30

Thr Ser His Pro Phe Glu Met Gln Tyr Gly Gln Val Ser Ser Tyr
            35                  40                  45

Pro Gln Gln Gln Ala Gln Gln Gln His Ser Met Pro Glu Gln Gln Pro
    50                  55                  60

Val Tyr Ala Ala Gln Pro Met Leu Asn Met His Gln Met Ala Thr Thr
65                  70                  75                  80

Asn Ala Phe Arg Gly Ala Leu Ser Met Thr Pro Ile Ala Ser Pro Gln
                85                  90                  95

Pro Thr His Leu Lys Pro Thr Ile Ile Val Gln Gln Asp Ser Pro Ala
            100                 105                 110
```

-continued

```
Leu Met Pro Leu Asp Thr Arg Phe Val Ser Asn Asp Phe Tyr Gly Phe
        115                 120                 125

Pro Ser Thr Pro Pro Leu Ser Thr Ser Gly Ser Thr Ile Ser Ser Pro
130                 135                 140

Pro Ser Ser Asn Gly Ser Leu His Thr Pro Ile Asn Asp Cys Phe Phe
145                 150                 155                 160

Ser Phe Glu Lys Val Glu Gly Val Lys Glu Gly Cys Glu Ser Asp Val
                165                 170                 175

His Cys Glu Leu Leu Ala Asn Thr Asp Trp Ser Arg Ser Asp Ser Pro
                180                 185                 190

Pro Leu Thr Pro Val Phe Ile Gln Pro Gln Ser Leu Thr Ala Ser Gln
        195                 200                 205

Ser Ser Asp Leu Leu Ser Ala Gln Ile Pro Cys Pro Ser Leu Ser Pro
210                 215                 220

Ser Pro Ser Pro Asp Ser Ala Thr Phe Ile Ser His Pro Gln Ser Ile
225                 230                 235                 240

Leu Ser Ala Glu Pro Ser Gly Ser Asp Phe Cys Asp Pro Arg Gln Leu
                245                 250                 255

Thr Val Glu Ser Ser Val Gly Ala Pro Ala Glu Leu Pro Pro Leu Pro
                260                 265                 270

Thr Leu Ser Cys Asn Glu Glu Pro Lys Val Val Leu Gly Ser Ala
        275                 280                 285

Thr Val Thr Leu Pro Val His Glu Gly Leu Ser Pro Ser Phe Ser Ser
        290                 295                 300

Ser Ser Glu Asp Pro Leu Gly Ser Leu Pro Thr Phe Asp Ser Phe Ser
305                 310                 315                 320

Asp Leu Asp Ser Glu Asp Glu Phe Ala Asn Lys Leu Val Asp Phe His
                325                 330                 335

Pro Ile Gly Asn Thr Tyr Phe Gln Gly Asp Lys Arg Gln Arg Leu Gly
                340                 345                 350

Thr Tyr Leu Leu Asp Glu Asp Glu Phe Leu Ser Glu Arg Ser Leu Glu
        355                 360                 365

Asp Leu Asp Asp Gln Glu Ala Phe Ala Gln Ser Gly Leu Pro Ser Val
        370                 375                 380

Glu Ser Thr Asp Phe Leu Ala Val Glu Gly Asp Ala Thr Gln Ser Thr
385                 390                 395                 400

Glu Glu Met Ser Ser Lys Lys Arg Val Thr Ser Arg Arg Ser Leu Lys
                405                 410                 415

Lys Ala Ser Thr Ser Glu Ser Ser Asp Ser Leu Ala Lys Lys Thr
                420                 425                 430

Gln Ala Ser Ala Thr Ser Arg Ser Gly His Ser Asp Thr Thr Ser Thr
        435                 440                 445

Val Gln Gln Ser Thr Ala Ser Ser Arg Gln Asn Ser Thr Ala Asn Thr
        450                 455                 460

Ser Asn Ser Glu Ser Pro Ala Ala Pro Val Ser Val Asn Arg Arg Gly
465                 470                 475                 480

Arg Lys Gln Ser Leu Thr Asp Asp Pro Ser Lys Thr Phe Val Cys Ser
                485                 490                 495

Leu Cys Ser Arg Arg Phe Arg Arg Gln Glu His Leu Lys Arg His Tyr
                500                 505                 510

Arg Ser Leu His Thr Gln Asp Lys Pro Phe Glu Cys His Glu Cys Gly
        515                 520                 525
```

```
Lys Lys Phe Ser Arg Ser Asp Asn Leu Ala Gln His Ala Arg Thr His
    530                 535                 540
Gly Gly Gly Ser Ile Val Met Gly Val Ile Asp Thr Asn Ser Ser Asn
545                 550                 555                 560
Thr Gln Pro Ala Phe Asp Glu Pro Glu Pro Arg Ala Leu Gly Leu Ala
                565                 570                 575
Leu Tyr Glu Ala Ala Asn Ala Ala Thr Ser Lys Ser Thr Thr Ser Glu
                580                 585                 590
Ser Ser Asp Gly Thr Ile Ser Asp Thr Ser Ser Val Gly Gly Arg Pro
            595                 600                 605
Ala Lys Lys Arg Arg Arg Asp Asp His Val
    610                 615

<210> SEQ ID NO 8
<211> LENGTH: 615
<212> TYPE: PRT
<213> ORGANISM: Neosartorya fischeri

<400> SEQUENCE: 8

Met Asp Ala Thr Tyr Thr Met Ala Gln Thr Pro Val Gln Gly Gln Pro
1               5                   10                  15
Ser Phe Ala Tyr Tyr Pro Thr Glu Ser Gln Ser Arg Gln Gln His Phe
                20                  25                  30
Thr Ser His Pro Ser Glu Met Gln Tyr Tyr Gly Gln Val Pro Pro Tyr
            35                  40                  45
Pro Gln Gln Gln His Ser Met Pro Glu Gln Gln Pro Val Tyr Ala Ala
        50                  55                  60
Gln Pro Met Leu Asn Met His Gln Met Ala Thr Thr Asn Ala Phe Arg
65                  70                  75                  80
Gly Ala Leu Ser Met Thr Pro Ile Ala Ser Pro Gln Pro Thr His Leu
                85                  90                  95
Lys Pro Thr Ile Ile Val Gln Gln Gln Asp Ser Pro Val Leu Met Pro
                100                 105                 110
Leu Asp Thr Arg Phe Val Ser Asn Asp Phe Tyr Gly Phe Pro Ser Thr
            115                 120                 125
Pro Pro Leu Ser Thr Ser Gly Ser Thr Ile Ser Ser Pro Pro Ser Ser
        130                 135                 140
Asn Gly Ser Leu His Thr Pro Ile Asn Asp Cys Phe Phe Ser Phe Glu
145                 150                 155                 160
Lys Val Glu Gly Val Lys Glu Gly Cys Glu Ser Asp Val His Cys Glu
                165                 170                 175
Leu Leu Ala Asn Thr Gly Trp Ser Arg Ser Asp Ser Pro Pro Leu Thr
            180                 185                 190
Pro Val Phe Ile Gln Pro Pro Ser Leu Thr Ala Ser Gln Ser Ser Asp
        195                 200                 205
Leu Leu Ser Ala His Met Ser Cys Pro Ser Leu Ser Pro Ser Pro Ser
        210                 215                 220
Pro Asp Ser Thr Thr Phe Ile Ser His Pro Gln Ser Val Leu Ser Ala
225                 230                 235                 240
Glu Pro Ser Gly Ser Asp Phe Cys Asp Pro Arg Gln Leu Thr Val Glu
                245                 250                 255
Ser Ser Val Gly Ala Pro Ala Glu Leu Pro Pro Leu Pro Thr Leu Ser
            260                 265                 270
Cys Asn Glu Glu Glu Pro Lys Val Val Leu Gly Ser Ala Thr Val Thr
        275                 280                 285
```

Leu Pro Val His Glu Gly Leu Ser Pro Ser Phe Ser Ser Ser Glu
    290                 295                 300

Asp Pro Leu Gly Ser Leu Pro Thr Phe Asp Ser Phe Ser Asp Leu Asp
305                 310                 315                 320

Ser Glu Asp Glu Phe Ala Asn Lys Leu Val Asp Phe His Pro Ile Gly
                325                 330                 335

Asn Thr Tyr Phe Leu Gly Asp Lys Arg Gln Arg Leu Gly Thr Tyr Leu
            340                 345                 350

Leu Asp Glu Asp Glu Phe Leu Ser Glu Arg Ser Leu Glu Asp Leu Asp
        355                 360                 365

Asp Gln Glu Ala Phe Ala Gln Ser Gly Leu Pro Ser Val Glu Ser Ser
    370                 375                 380

Asp Phe Leu Ala Ala Glu Gly Asp Ala Thr Gln Asn Thr Glu Glu Met
385                 390                 395                 400

Ser Ser Lys Lys Arg Val Thr Ser Arg Arg Ser Leu Lys Arg Ala Ser
                405                 410                 415

Thr Ser Glu Ser Ser Asp Ser Leu Ala Lys Lys Thr Gln Ala Ser
            420                 425                 430

Ala Thr Ser Arg Ser Gly His Ser Glu Thr Thr Ser Thr Val Gln Gln
        435                 440                 445

Ser Thr Ala Ser Ser Arg Gln Asn Ser Thr Ala Asn Thr Ser Ser Ser
    450                 455                 460

Gly Ser Pro Ala Ala Pro Val Ser Val Asn Arg Arg Gly Arg Lys Gln
465                 470                 475                 480

Ser Leu Thr Asp Asp Pro Ser Lys Thr Phe Val Cys Ser Leu Cys Ser
                485                 490                 495

Arg Arg Phe Arg Arg Gln Glu His Leu Lys Arg His Tyr Arg Ser Leu
            500                 505                 510

His Thr Gln Asp Lys Pro Phe Glu Cys His Glu Cys Gly Lys Lys Phe
        515                 520                 525

Ser Arg Ser Asp Asn Leu Ala Gln His Ala Arg Thr His Gly Gly Gly
    530                 535                 540

Ser Ile Val Met Gly Val Ile Asp Thr Asn Gly Ser Asn Thr Gln Pro
545                 550                 555                 560

Ala Phe Asp Glu Pro Glu Pro Arg Ala Leu Gly Leu Ala Leu Tyr Glu
                565                 570                 575

Ala Ala Asn Ala Ala Thr Ser Lys Ser Thr Thr Ser Glu Ser Ser Asp
            580                 585                 590

Gly Thr Ile Ser Asp Thr Ser Ser Val Gly Gly Arg Pro Ala Lys Lys
        595                 600                 605

Arg Arg Arg Asp Asp His Val
    610                 615

<210> SEQ ID NO 9
<211> LENGTH: 1042
<212> TYPE: PRT
<213> ORGANISM: Trichoderma reesei

<400> SEQUENCE: 9

Met Asp Tyr Thr Gln Tyr His Ala Leu Gly His Gly Glu Val Leu Asp
1               5                   10                  15

Pro Asn Asp Pro Asn Lys Thr Ser Ala Pro Ala Ala Pro Gln Phe Gln
            20                  25                  30

Pro Pro Ser Ser Pro Tyr Val Pro Pro Gly Ser Pro Tyr Gly Ala Pro

```
                35                  40                  45
Pro Tyr His Gly Gly His Gln Ala Pro Pro Met Ala Met Pro Pro Pro
 50                  55                  60

Ser Thr Pro Gly Tyr Gly Pro Pro Gln Gly Gln Ser Phe Pro Gly Ser
 65                  70                  75                  80

Pro Met Pro Ser Gln Asp Ala Gly Leu Ala Ala Gln Phe Gly Gly Met
                 85                  90                  95

Ser Leu Gly Ala Asp Ala Gly Ala Ala Arg Lys Lys Lys Lys
                100                 105                 110

Asp Arg His Ala Tyr His Ser Val Glu Pro Thr Gly Ser Ser Gln Ala
                115                 120                 125

Phe Asn Gly Leu Pro Pro Gly Thr Pro Ala Glu Gln Phe Leu Asn Val
                130                 135                 140

Asn Asn Pro Gln Gly Ile Pro Ala Leu Gly Gly Gln Phe Gly Ser Pro
145                 150                 155                 160

Leu Ala Ser Pro Met Gly Thr Pro His Met Ala Asn Pro Gly Gln Phe
                165                 170                 175

Pro Ala Pro Thr Ser Pro Phe Thr Pro Ser Ala Pro Val Ser Pro Ala
                180                 185                 190

Glu Phe Ala Ser Arg Phe Gly Ser Pro Asp Ala Ala Thr Ser Ile Gly
                195                 200                 205

Ser Ala Gly Pro Ser Gln Val Ser Pro Asp Asp Met Pro Ser Ile Pro
210                 215                 220

Ala Ser Arg Asp Ala Ile Gln Glu His Phe Phe Lys Asn Val Tyr Pro
225                 230                 235                 240

Thr Phe Glu Arg His Val Pro Pro Ala Thr Val Ser Phe Val Ala
                245                 250                 255

Phe Asp Gln Gly Asn Ala Ser Pro Lys Phe Thr Arg Leu Thr Leu Asn
                260                 265                 270

Asn Ile Pro Thr Thr Ala Glu Gly Leu His Ala Thr Gly Leu Pro Leu
                275                 280                 285

Gly Met Leu Ile Gln Pro Leu Ala Pro Leu Gln Ala Gly Glu Ala Glu
                290                 295                 300

Ile Pro Val Leu Asp Phe Gly Asp Ala Gly Pro Pro Arg Cys Arg Arg
305                 310                 315                 320

Cys Arg Ala Tyr Ile Asn Pro Phe Met Met Phe Arg Ser Gly Gly Asn
                325                 330                 335

Lys Phe Val Cys Asn Leu Cys Ser Tyr Pro Asn Glu Thr Pro Pro Glu
                340                 345                 350

Tyr Phe Cys Ala Val Ser Pro Gln Gly Val Arg Leu Asp Arg Asp Gln
                355                 360                 365

Arg Pro Glu Leu His Arg Gly Thr Val Glu Phe Val Val Pro Lys Glu
                370                 375                 380

Tyr Trp Thr Arg Glu Pro Val Gly Leu Arg Trp Leu Phe Val Ile Asp
385                 390                 395                 400

Val Thr Gln Glu Ser Tyr Asn Lys Gly Phe Met Glu Thr Phe Cys Glu
                405                 410                 415

Gly Ile Leu Ala Ala Leu Tyr Gly Gly Asn Asp Glu Asn Asp Glu
                420                 425                 430

Asp Gly Glu Pro Lys Arg Arg Ile Pro Lys Gly Ala Lys Val Gly Phe
                435                 440                 445

Ile Thr Tyr Asp Lys Asp Ile His Phe Tyr Asn Ile Asn Pro His Leu
450                 455                 460
```

```
Asp Gln Ala His Met Met Ile Met Pro Asp Leu Asp Pro Phe Leu
465                 470                 475                 480

Pro Leu Gly Glu Gly Leu Phe Val Asp Pro Tyr Glu Ser Lys Ala Ile
            485                 490                 495

Ile Thr Ser Leu Leu Thr Arg Leu Pro Glu Met Phe Ser Thr Ile Lys
                500                 505                 510

Asn Pro Glu Pro Ala Leu Leu Ala Thr Leu Asn Ala Ala Val Ala Ala
            515                 520                 525

Leu Glu Ala Thr Gly Gly Lys Val Val Cys Ser Cys Ser Thr Leu Pro
530                 535                 540

Thr Trp Gly Pro Gly Arg Leu Phe Met Arg Asp Asp Gly Asn His Pro
545                 550                 555                 560

Gly Gly Glu Leu Asp Lys Lys Leu Tyr Thr Thr Glu His Pro Ala Trp
                565                 570                 575

Lys Lys Val Ser Glu Lys Met Ala Ser Ser Gly Ile Gly Val Asp Phe
            580                 585                 590

Phe Leu Ala Ala Pro Ser Gly Gly Tyr Leu Asp Ile Ala Thr Ile Gly
            595                 600                 605

His Val Ala Ala Thr Thr Gly Gly Glu Thr Phe Tyr Tyr Pro Asn Phe
610                 615                 620

Ile Ala Pro Arg Asp Gly Ala Arg Leu Ser Met Glu Ile Thr His Ala
625                 630                 635                 640

Ile Thr Arg Glu Thr Gly Phe Gln Ala Leu Met Lys Val Arg Cys Ser
                645                 650                 655

Thr Gly Leu Gln Val Ala Ala Tyr His Gly Asn Phe Val Gln His Thr
                660                 665                 670

Phe Gly Ala Asp Leu Glu Ile Gly Val Ile Asp Ala Asp Lys Ala Leu
            675                 680                 685

Gly Val Ser Phe Ser His Asp Gly Lys Leu Asp Pro Lys Leu Asp Ala
            690                 695                 700

His Phe Gln Thr Ala Leu Leu Tyr Thr Thr Ala Ser Gly Gln Arg Arg
705                 710                 715                 720

Val Arg Cys Ser Asn Val Ile Ala Ser Val Ser Asp Thr Ser Lys Glu
                725                 730                 735

Ser Asn Thr Lys Glu Leu Ala Ile Arg Gln Cys Leu Lys Phe Val Asp
            740                 745                 750

Gln Asp Ala Val Val Gly Ile Phe Ala Lys Glu Ala Ser Thr Lys Leu
            755                 760                 765

Ala Thr Thr Ser Ala Asn Leu Gln Asp Val Arg Asn Trp Leu Thr Glu
            770                 775                 780

Arg Thr Ile Asp Ile Met Ala Tyr Tyr Lys Lys His Ser Ala Asn Gln
785                 790                 795                 800

Phe Pro Pro Ser Gln Leu Val Met Pro Glu Arg Leu Lys Glu Phe Cys
                805                 810                 815

Met Tyr Met Leu Gly Met Leu Lys Cys Arg Ala Phe Lys Gly Gly Ile
            820                 825                 830

Glu Asn Ser Asp Arg Arg Val His Glu Leu Arg Met Val Arg Ser Met
            835                 840                 845

Gly Pro Leu Glu Leu Ser Leu Tyr Leu Tyr Pro Arg Met Ile Ala Leu
850                 855                 860

His Asn Leu Gln Pro Glu Glu Gly Phe Ala Asp Pro Glu Thr Gly His
865                 870                 875                 880
```

```
Leu Lys Met Pro Pro Ser Val Arg Thr Ser Phe Ser Arg Val Glu Pro
            885                 890                 895

Gly Gly Val Tyr Leu Val Asp Asn Gly Gln Gln Cys Leu Leu Trp Phe
            900                 905                 910

His Ala Gln Thr Ser Pro Asn Leu Ile Thr Asp Leu Phe Gly Glu Gly
            915                 920                 925

His Asp Ser Leu Lys Gly Leu Asp Pro Tyr Thr Ser Thr Leu Pro Val
            930                 935                 940

Leu Glu Thr His Leu Ser Ala Gln Val Arg Asn Ile Ile Glu Phe Leu
945                 950                 955                 960

Lys Ser Met Arg Gly Ser Lys Gly Met Thr Ile Gln Leu Ala Arg Gln
            965                 970                 975

Gly Ile Asp Gly Ala Glu Tyr Glu Phe Ala Arg Met Leu Val Glu Asp
            980                 985                 990

Arg Asn Asn Glu Ala Lys Ser Tyr Val Asp Trp Leu Val His Ile His
            995                 1000                1005

Arg Gly Val Gln Leu Glu Leu Ser Gly Gln Arg Lys Lys Glu Gly
            1010                1015                1020

Asp Gly Glu Ala Thr Ala Val Met Ala Asn Phe Ala Gly Leu Arg
            1025                1030                1035

Pro Ala Tyr Trp
            1040

<210> SEQ ID NO 10
<211> LENGTH: 1015
<212> TYPE: PRT
<213> ORGANISM: Aspergillus oryzae

<400> SEQUENCE: 10

Met Ala Asp Gln Ser Met Tyr Asn Thr Leu Gly Gln Gly Thr Ser Pro
1               5                   10                  15

Ala Glu Asp Pro Ser Asn Pro Asn Arg Met Ala His Gln Val Pro Pro
            20                  25                  30

Gln Ser Gln Pro Ala Ala Gly Phe Pro Pro Gly Pro Tyr Pro Pro Gln
        35                  40                  45

Pro Gly Ala Tyr Tyr Gly Asn Pro Pro Asn Gln Tyr Asp Ala Pro
50                  55                  60

Ala Ala Ala Pro Pro Thr Gln Gln Leu Gln Ser Pro Pro Arg Gly
65                  70                  75                  80

Leu Ala Pro Ser Pro Gln Leu Ala Tyr Gly Thr Glu Thr Gln Thr His
            85                  90                  95

Met Gly Ala Pro Ala Asp Pro Met Ala Gly Leu Ala Ser Gln Met Ser
            100                 105                 110

Gly Leu Gly Ile Met Gly Asp Ser Gly Ala Arg Pro Lys Lys Lys
            115                 120                 125

His Arg His Ala His His Glu Ile Gly Gly Ala Thr Ala Ser Ala Pro
130                 135                 140

Gln Gln Phe Ala Gly Met Pro Gln Ala Gly Met Gln Pro Ser Ser Gln
145                 150                 155                 160

Phe Leu Asn Thr Gly Leu Asn Gln Ala Pro Arg Pro Ile Ser Pro Ala
            165                 170                 175

Ala Gly Val Pro Pro Ala Gly Ile Val Pro Gln Pro Gly Val Pro Ala
            180                 185                 190

Pro Gly Ser Gly Ser Val Pro Thr Gln Gly Lys Ile Asp Pro Glu Gln
            195                 200                 205
```

```
Ile Pro Ser Ile Pro Gln Ser Arg Asp Ile Pro Thr Met Tyr Tyr Phe
    210                 215                 220

Asp His Ile Tyr Pro Thr Met Glu Arg His Leu Pro Pro Ala Ala
225                 230                 235                 240

Val Pro Phe Val Ala His Asp Gln Gly Asn Ser Ser Pro Lys His Ala
                245                 250                 255

Arg Leu Thr Leu Asn Asn Ile Pro Thr Thr Ser Asp Phe Leu Ser Ser
            260                 265                 270

Thr Ala Leu Pro Leu Gly Met Val Leu Gln Pro Leu Ala Arg Leu Asp
        275                 280                 285

Pro Gly Glu Pro Glu Val Pro Val Leu Asp Phe Gly Glu Met Gly Pro
    290                 295                 300

Pro Arg Cys Arg Arg Cys Arg Ala Tyr Ile Asn Pro Phe Met Thr Phe
305                 310                 315                 320

Arg Ser Gly Gly Asn Lys Phe Val Cys Asn Met Cys Thr Phe Pro Asn
                325                 330                 335

Asp Val Ala Pro Glu Tyr Phe Ala Pro Leu Asp Met Ser Gly Ala Arg
            340                 345                 350

Val Asp Arg Leu Gln Arg Pro Glu Leu Met Ile Gly Thr Val Glu Phe
        355                 360                 365

Met Val Pro Lys Glu Tyr Trp Asn Lys Glu Pro Val Gly Leu Gln Arg
    370                 375                 380

Leu Phe Leu Ile Asp Val Ser Gln Glu Ser Val Asn Arg Gly Phe Leu
385                 390                 395                 400

Lys Gly Val Cys Lys Gly Ile Thr Glu Ala Leu Tyr Gly Ala Pro Asp
                405                 410                 415

Ala Ser Glu Glu Asp Ala Ala Ala Arg Arg Val Pro Glu Gly Ser Lys
            420                 425                 430

Ile Gly Ile Val Thr Tyr Asp Arg Glu Val His Phe Tyr Asn Leu Ser
        435                 440                 445

Ala Gln Leu Asp Gln Ala Gln Met Met Val Met Thr Asp Leu Glu Glu
    450                 455                 460

Pro Phe Val Pro Leu Ser Glu Gly Leu Phe Val Asp Pro Tyr Glu Ser
465                 470                 475                 480

Lys Asp Ile Ile Thr Ser Leu Leu His Arg Ile Pro Lys Ile Phe Ser
                485                 490                 495

His Ile Lys Lys Pro Glu Pro Ala Leu Leu Pro Ala Leu Asn Ala Ala
            500                 505                 510

Met Ser Ala Leu Gln Ala Thr Gly Gly Lys Ile Phe Ala Ser Ile Cys
        515                 520                 525

Ser Leu Pro Thr Trp Gly Pro Gly Ala Leu His Met Arg Asp Asp Pro
    530                 535                 540

Lys Val His Gly Thr Asp Ala Glu Arg Lys Leu Phe Thr Thr Asp Asn
545                 550                 555                 560

Gln Ala Trp Arg Thr Thr Ala Gly Lys Met Ala Glu His Gly Ile Gly
                565                 570                 575

Val Asp Met Phe Val Ala Ala Pro Gly Gly Thr Tyr Val Asp Val Ala
            580                 585                 590

Thr Ile Gly His Val Ala Glu Val Ser Gly Gly Glu Thr Phe Phe Tyr
        595                 600                 605

Pro Asn Phe His Ala Pro Arg Asp Ile Leu Lys Leu Ser Gln Glu Phe
610                 615                 620
```

```
Ala His Ala Val Thr Arg Glu Thr Gly Tyr Gln Ala Met Met Lys Val
625                 630                 635                 640

Arg Cys Ser Asn Gly Leu Gln Val Ser Ala Tyr His Gly Asn Phe Ile
            645                 650                 655

Gln His Ala Leu Gly Ala Asp Leu Glu Ile Gly Ser Ile Asp Ala Asp
        660                 665                 670

Lys Ala Ile Gly Val Met Phe Ser Tyr Asp Gly Lys Leu Asp Pro Lys
    675                 680                 685

Leu Asp Ala His Phe Gln Ala Leu Leu Tyr Thr Thr Ala Glu Gly
690                 695                 700

Gln Arg Arg Val Arg Cys Ile Asn Val Ala Ala Val Asn Glu Gly
705                 710                 715                 720

Gly Leu Glu Thr Met Lys Phe Ile Asp Gln Asp Cys Val Val Ser Ile
                725                 730                 735

Met Ala Lys Glu Ala Ala Lys Thr Val Asp Lys Ser Leu Lys Asp
            740                 745                 750

Ile Arg Ala Ser Ile Thr Glu Lys Thr Val Asp Ile Phe Ser Gly Tyr
        755                 760                 765

Arg Lys Val Phe Ser Gly Ser His Pro Pro Gly Gln Leu Val Leu Pro
770                 775                 780

Glu Asn Leu Lys Glu Phe Ser Met Tyr Met Leu Ala Leu Ile Lys Ser
785                 790                 795                 800

Arg Ala Phe Lys Gly Gly Gln Glu Ala Ser Asp Arg Ile His Asp
                805                 810                 815

Met Arg Met Leu Arg Ser Ile Gly Ala Thr Glu Leu Ala Leu Tyr Leu
            820                 825                 830

Tyr Pro Arg Val Ile Pro Ile His Asn Met Gln Pro Glu Asp Gly Phe
        835                 840                 845

Pro Asn Glu Gln Gly Gln Leu Gln Val Pro Pro Ser Leu Arg Ala Ser
850                 855                 860

Phe Ser Lys Ile Glu Glu Gly Gly Ala Tyr Leu Val Asp Asn Gly Gln
865                 870                 875                 880

Ile Cys Leu Leu Trp Leu His Ser Arg Val Ser Pro Asn Leu Leu Glu
                885                 890                 895

Asp Leu Leu Gly Pro Gly Gln Ser Ser Leu Gln Gly Leu Asn Pro Gln
            900                 905                 910

Thr Ser Ser Leu Pro Val Leu Glu Thr His Leu Asn Ala Gln Val Arg
        915                 920                 925

Asn Leu Leu Gln Tyr Phe Ser Thr Met Arg Gly Ser Lys Ser Val Ala
930                 935                 940

Ile Gln Leu Ala Arg Gln Gly Leu Asp Gly Ala Glu Tyr Glu Phe Ala
945                 950                 955                 960

Arg Leu Leu Val Glu Asp Arg Asn Asn Glu Ala Gln Ser Tyr Val Asp
                965                 970                 975

Trp Leu Val His Ile His Arg Gln Ile Asn Leu Glu Leu Ala Gly His
            980                 985                 990

Arg Lys Arg Glu Asp Thr Ser Ala  Glu Gly Ser Leu Thr  Ser Leu Ala
        995                 1000                1005

Gly Leu  Arg Ala Pro Tyr Trp
    1010                1015

<210> SEQ ID NO 11
<211> LENGTH: 1009
<212> TYPE: PRT
```

<213> ORGANISM: Aspergillus niger

<400> SEQUENCE: 11

```
Met Ala Asp Pro Asn Met Tyr His Thr Tyr Gly Gln Ala Pro Val Pro
1               5                   10                  15

Gly Glu Asn Pro Ser Asp Pro Asn Gln Met Ala Tyr Gln Val Pro Pro
            20                  25                  30

Gln Gly Tyr Pro Ala Ala Gly Ile Pro Pro Gly Pro Ser Pro Pro Gln
        35                  40                  45

Pro Gly Ala Ala Tyr Gly Val Pro Ala Pro Asn Gln Gln Trp Pro Ala
    50                  55                  60

Tyr Gly Ser Pro Pro Ala Gln Gln Pro Leu Gln Gln Pro Pro Ser
65                  70                  75                  80

Gln Phe Ala His Gln Ala Asp Pro Gln Ala Ala Met Gly Ala Pro Val
                85                  90                  95

Asp Pro Gly Met Ala Gly Leu Ala Ser Gln Met Ser Gly Leu Gly Ile
            100                 105                 110

Met Gly Gly Glu Gly Gly Ala Ala Arg Ser Ser Lys Lys Lys His Arg
        115                 120                 125

His Ala His His Glu Ile Ala Gly Ala Ser Ala Ser Val Ala Gln Pro
    130                 135                 140

Phe Ala Ala Pro Gln Asp Pro Met Gln Pro Thr Ser Gln Phe Leu
145                 150                 155                 160

Asn Thr Gly Leu Asn Gln Ala Pro Arg Pro Ile Ser Pro Ala Ala Ser
                165                 170                 175

Ile Pro Ala Pro Val Asn Pro Ala Phe Gly Gly Ala Gly Ala Val
            180                 185                 190

Pro Thr Gln Gly Lys Val Asp Pro Glu Gln Ile Pro Ser Ile Pro Arg
        195                 200                 205

Ser Arg Asp Leu Pro Ala Gln Tyr Tyr Phe Asn His Val Tyr Pro Thr
    210                 215                 220

Met Glu Arg His Leu Pro Pro Ala Ala Val Pro Phe Val Ala His
225                 230                 235                 240

Asp Gln Gly Asn Ser Ser Pro Lys Tyr Ala Arg Leu Thr Leu Asn Asn
                245                 250                 255

Ile Pro Ser Thr Ser Asp Phe Leu Ser Ser Thr Gly Leu Pro Leu Gly
            260                 265                 270

Met Val Leu Gln Pro Leu Ala Arg Leu Asp Gly Glu Gln Pro Ile Pro
        275                 280                 285

Val Leu Asp Phe Gly Asp Ala Gly Pro Pro Arg Cys Arg Arg Cys Arg
    290                 295                 300

Ala Tyr Ile Asn Pro Phe Met Ser Phe Arg Ser Gly Gly Asn Lys Phe
305                 310                 315                 320

Val Cys Asn Met Cys Thr Phe Pro Asn Asp Val Pro Pro Glu Tyr Phe
                325                 330                 335

Ala Pro Leu Asp Pro Ser Gly Ser Arg Ile Asp Arg Met Gln Arg Pro
            340                 345                 350

Glu Leu Met Met Gly Thr Val Glu Phe Leu Val Pro Lys Asp Tyr Trp
        355                 360                 365

Asn Lys Glu Pro Val Gly Leu Gln Trp Leu Leu Ile Asp Val Ser
    370                 375                 380

Gln Glu Ser Val Asn Lys Gly Phe Leu Lys Gly Val Cys Lys Gly Ile
385                 390                 395                 400
```

```
Met Glu Ala Leu Tyr Ser Glu Glu Thr Glu Asn Pro Glu Asp Glu Ala
                405                 410                 415

Pro Ala Arg Arg Ile Pro Glu Gly Ala Lys Ile Gly Ile Val Thr Tyr
            420                 425                 430

Asp Lys Glu Val His Phe Tyr Asn Leu Ser Ala Gln Leu Asp Gln Ala
        435                 440                 445

Gln Met Met Val Met Thr Asp Leu Glu Glu Pro Phe Val Pro Leu Ser
450                 455                 460

Glu Gly Leu Phe Val Asp Pro Tyr Glu Ser Lys Asp Val Ile Thr Ser
465                 470                 475                 480

Leu Leu Gln Arg Ile Pro Ser Ile Phe Ser His Val Lys Asn Pro Gln
                485                 490                 495

Pro Ala Leu Leu Pro Ala Leu Asn Ala Ala Leu Ser Ala Leu Arg Pro
            500                 505                 510

Thr Gly Gly Lys Ile Val Gly Thr Ile Ala Ser Leu Pro Thr Trp Gly
        515                 520                 525

Pro Gly Ala Leu Ser Leu Arg Asp Asp Pro Lys Val His Gly Thr Asp
530                 535                 540

Ala Glu Arg Lys Leu Phe Thr Thr Glu His Ala Gly Trp Arg Glu Thr
545                 550                 555                 560

Ala Gly His Leu Ala Glu Ala Gly Ile Gly Leu Asp Met Phe Ile Ala
                565                 570                 575

Ala Pro Ser Gly Thr Tyr Met Asp Val Ala Thr Ile Gly His Ile Pro
            580                 585                 590

Glu Val Thr Gly Gly Glu Thr Phe Phe Tyr Pro Asn Phe His Ala Pro
        595                 600                 605

Arg Asp Ile Arg Lys Leu Ser Lys Glu Leu Ala His Ala Ile Thr Arg
610                 615                 620

Glu Thr Gly Tyr Gln Ala Leu Met Lys Val Arg Cys Ser Asn Gly Leu
625                 630                 635                 640

Gln Val Ser Gly Tyr His Gly Asn Phe Val Gln His Thr Phe Gly Ala
                645                 650                 655

Asp Leu Glu Ile Gly Ala Ile Ala Asp Lys Ala Ile Gly Val Val
            660                 665                 670

Phe Ser Tyr Asp Gly Lys Leu Asp Pro Lys Leu Asp Ala His Phe Gln
675                 680                 685

Ala Ala Leu Leu Tyr Thr Ser Ala Asn Gly Gln Arg Arg Val Arg Cys
            690                 695                 700

Ile Asn Thr Val Ala Ala Val Asn Glu Gly Gly Met Glu Thr Met Lys
705                 710                 715                 720

Phe Val Asp Gln Asp Ala Val Val Ala Met Val Ala Lys Asp Ala Ala
                725                 730                 735

Ser Lys Thr Leu Asp Lys Ser Leu Lys Asp Ile Arg Ala Gly Val Ser
            740                 745                 750

Glu Lys Thr Val Asp Ile Phe Ser Gly Tyr Arg Lys Ile Phe Ser Gly
        755                 760                 765

Ser His Pro Pro Gly Gln Leu Val Leu Pro Glu Asn Leu Lys Glu Phe
770                 775                 780

Ser Met Tyr Met Leu Ser Leu Ile Lys Ser Arg Ala Ile Lys Gly Gly
785                 790                 795                 800

Gln Glu Ala Ser Asp Arg Arg Ile His Asp Met Arg Met Leu Arg Ser
                805                 810                 815

Ile Gly Cys Thr Glu Leu Ser Leu Tyr Leu Tyr Pro Arg Ile Ile Pro
```

```
                        820                 825                 830
Ile His Asn Met Gln Pro Thr Asp Gly Phe Pro Asn Glu Gln Gly Gln
                835                 840                 845
Leu Gln Val Pro Pro Ser Leu Arg Ala Ser Phe Ser Lys Ile Glu Glu
        850                 855                 860
Gly Gly Ala Tyr Leu Val Asp Asn Gly Gln Gln Cys Leu Leu Trp Leu
865                 870                 875                 880
His Ser His Val Ser Pro Asn Leu Leu Glu Asp Leu Phe Gly Glu Gly
                885                 890                 895
Gln Thr Ser Leu Gln Gly Leu Ser Pro Gln Ile Ser Thr Ile Pro Val
                900                 905                 910
Leu Glu Thr His Leu Asn Ala Gln Val Arg Asn Leu Leu Gln Tyr Phe
                915                 920                 925
Ser Thr Ile Arg Gly Ser Lys Ala Val Thr Ile Gln Leu Ala Arg Gln
                930                 935                 940
Gly Leu Asp Gly Ala Glu Tyr Glu Phe Ala Arg Met Leu Val Glu Asp
945                 950                 955                 960
Arg Asn Asn Glu Ala Gln Ser Ser Val Asp Trp Leu Val His Ile His
                965                 970                 975
Arg Gln Ile Asn Leu Glu Leu Ala Gly His Arg Lys Arg Glu Asp Thr
                980                 985                 990
Ala Gly Glu Gly Gly Leu Thr Ser  Leu Ala Gly Leu Arg  Ala Pro Tyr
                995                 1000                1005
Trp

<210> SEQ ID NO 12
<211> LENGTH: 999
<212> TYPE: PRT
<213> ORGANISM: Penicillium funiculosum

<400> SEQUENCE: 12

Met Ala Asp Tyr Ser Thr Tyr His Ser Ser Gly Tyr Ala Gly Ala Pro
1               5                   10                  15
Gly Glu Asp Pro Asn Arg Gln Gln Pro Ala Val Pro Ala Pro Tyr His
                20                  25                  30
Ser Pro Asn Ala Pro Pro Gly Gln Ala Ile Gln Gln Pro Gly Ile Thr
        35                  40                  45
Pro Tyr Gly Ala Ala Gln Pro Pro Gln Phe Pro Gly Gln Pro Gly Val
        50                  55                  60
Gly Tyr Gly Val Ala Pro Val Pro Ser Pro Gln Ala Leu Gly Gly
65                  70                  75                  80
Pro Asp Val Gly Asp Leu Ala Thr Arg Ile Gly Gly Leu Gly Ile Ile
                85                  90                  95
Ser Asp Ala Gly Thr Arg Ser His Lys Lys His Arg His Ala Tyr
                100                 105                 110
His Asp Ile Gly Gly Pro Asn Ala Gln Gly Leu Asn Thr Phe Pro Ser
        115                 120                 125
Gln Thr Asn Leu Gln Ser Gln Phe Leu Asn Thr Gly Leu Asn Gln Pro
        130                 135                 140
Glu Gln Gln Pro Ala Ala Pro Ala Ala Phe Pro Gly Ala Pro Val Gly
145                 150                 155                 160
Gln Val Pro Ala Asn Val Ala Pro Gly Ala Ala Pro Glu Val Gly Gly
                165                 170                 175
Val Gly Ser Val Pro Thr Gln Gly Lys Ile Asp Pro Glu Gln Ile Pro
```

```
            180                 185                 190
Ser Val Pro Arg Ser Asp Leu Pro Ala Gln Tyr Tyr Phe Asn Asn
            195                 200                 205

Val Tyr Pro Thr Met Glu Arg His Val Pro Pro Ala Ser Ile Pro
            210                 215                 220

Phe Ile Ala His Asp Gln Gly Asn Ser Ser Pro Lys Val Ala Arg Leu
225                 230                 235                 240

Thr Leu Asn Asn Ile Pro Ser Ser Ser Asp Phe Leu Gln Ser Thr Gly
                245                 250                 255

Leu Pro Leu Gly Met Ile Leu Gln Pro Leu Ala Lys Leu Asp Ala Gly
            260                 265                 270

Glu Gln Pro Val Pro Val Ile Asp Phe Gly Asp Ile Gly Pro Pro Arg
            275                 280                 285

Cys Arg Arg Cys Arg Thr Tyr Ile Asn Pro Phe Met Thr Phe Arg Ser
            290                 295                 300

Gly Gly Asn Lys Phe Val Cys Asn Met Cys Thr Phe Pro Asn Asp Val
305                 310                 315                 320

Pro Pro Glu Tyr Phe Ala Pro Val Asp Pro Ser Gly Val Arg Val Asp
                325                 330                 335

Arg Leu Gln Arg Pro Glu Leu Met Leu Gly Thr Val Glu Phe Thr Val
            340                 345                 350

Pro Lys Glu Tyr Trp Val Lys Glu Pro Ala Gly Leu His Gln Leu Phe
            355                 360                 365

Leu Ile Asp Val Ser Gln Glu Ser Val Asn Arg Gly Phe Leu Lys Gly
            370                 375                 380

Val Cys Asp Gly Ile Ile Asn Ala Leu Tyr Gly Glu Glu Pro Val
385                 390                 395                 400

Glu Gly Ala Glu Pro Glu Thr Arg Lys Val Pro Glu Gly Ser Lys Ile
                405                 410                 415

Gly Ile Val Thr Phe Asp Arg Glu Ile His Phe Tyr Asn Leu Leu Pro
            420                 425                 430

Arg Leu Asp Lys Ala Gln Met Met Val Met Thr Asp Leu Glu Glu Pro
            435                 440                 445

Phe Val Pro Leu Ser Glu Gly Leu Phe Val Asp Pro Tyr Glu Ser Lys
450                 455                 460

Asp Val Ile Thr Ser Leu Leu Glu Gln Leu Pro Ser Leu Phe Ala Arg
465                 470                 475                 480

Val Lys Ser Pro Glu Ser Thr Leu Leu Pro Thr Ile Lys Ala Ala Ile
                485                 490                 495

Ser Ala Leu Gln Ala Thr Gly Gly Lys Ile Ile Cys Cys Leu Thr Ser
            500                 505                 510

Leu Pro Thr Tyr Gly Pro Gly Lys Leu Val Met Lys Asp Lys Ser Gln
            515                 520                 525

Ala Pro Asp Gly Glu Asn Lys Leu Phe Ala Ile Asp Asn Pro Asp Tyr
            530                 535                 540

Lys Ala Ala Ala Thr Lys Leu Thr Glu Ala Gly Val Gly Ile Asp Phe
545                 550                 555                 560

Phe Val Ala Ala Pro Gly Gly Ser Phe Met Asp Leu Thr Thr Ile Gly
                565                 570                 575

Tyr Thr Ala Ala Ile Ser Gly Gly Glu Cys Phe Phe Tyr Pro Asn Phe
            580                 585                 590

His Ser Pro Arg Asp Ser Leu Lys Leu Ala Gln Glu Ile Ser His Thr
            595                 600                 605
```

```
Val Thr Arg Glu Thr Gly Tyr Gln Ala Leu Met Lys Val Arg Cys Ser
    610                 615                 620

Asn Gly Leu Gln Val Ser Ala Tyr Tyr Gly Asn Phe Leu Gln His Thr
625                 630                 635                 640

Phe Gly Ala Asp Leu Glu Ile Gly Thr Ile Asp Ala Asp Lys Ala Leu
                645                 650                 655

Gly Val Leu Phe Ser Tyr Asp Gly Lys Leu Asp Pro Lys Leu Asp Ala
                660                 665                 670

His Phe Gln Ala Ala Leu Leu Tyr Thr Ala Ala Asn Gly Gln Arg Arg
            675                 680                 685

Val Arg Cys Ile Asn Ile Val Ala Gly Val Asn Glu Gly Gly Ile Glu
    690                 695                 700

Thr Met Lys Cys Ile Asp Gln Asp Ala Val Val Ala Ile Ile Ala Lys
705                 710                 715                 720

Glu Ala Ala Ser Lys Ala Gly Asp Lys Thr Leu Lys Asp Ile Arg Ala
                725                 730                 735

Ser Ile Thr Glu Lys Thr Val Asp Ile Phe Ser Gly Tyr Arg Lys Asn
                740                 745                 750

Phe Ser Gly Ser His Pro Pro Gly Gln Leu Val Leu Pro Glu Asn Leu
            755                 760                 765

Lys Glu Phe Ser Met Tyr Met Leu Gly Leu Leu Lys Ser Arg Ala Phe
    770                 775                 780

Lys Gly Gly Ser Glu Thr Ala Asp Arg Arg Val His Asp Leu Arg Met
785                 790                 795                 800

Leu Arg Ser Ile Gly Cys Leu Glu Leu Ser Leu Tyr Leu Tyr Pro Arg
                805                 810                 815

Ile Ile Pro Ile His Asn Met Ser Ala Glu Asp Gly Phe Ala Asn Glu
                820                 825                 830

Gln Gly Gln Leu Gln Val Pro Pro Ala Leu Arg Ala Ser Phe Ser Arg
            835                 840                 845

Val Glu Glu Gly Gly Ala Tyr Leu Ile Asp Asn Gly Gln Gly Ile Leu
    850                 855                 860

Leu Trp Ile His Ser Phe Val Ser Pro Asn Leu Leu Glu Asp Leu Phe
865                 870                 875                 880

Gly Pro Gly Ile Thr Ser Leu Gln Ala Leu Asp Pro Asn Thr Ser Ser
                885                 890                 895

Leu Pro Val Leu Glu Thr His Leu Asn Ala Gln Val Arg Asn Leu Leu
                900                 905                 910

Gln Tyr Leu Ser Thr Val Arg Gly Ser Lys Ala Val Thr Ile Gln Leu
            915                 920                 925

Ala Arg Gln Gly Ile Asp Gly Ala Glu Tyr Glu Phe Ala Arg Ser Leu
    930                 935                 940

Val Glu Asp Arg Asn Asn Glu Ala Gln Ser Tyr Val Asp Trp Leu Val
945                 950                 955                 960

His Ile His Arg Gln Ile Asn Leu Glu Leu Ala Gly His Arg Lys Lys
                965                 970                 975

Glu Asp Ser Ala Thr Ser Ser Gly Glu Gly Ala Leu Ser Ser Leu Ala
                980                 985                 990

Gly Ile Arg Ala Pro Tyr Trp
            995

<210> SEQ ID NO 13
<211> LENGTH: 1011
```

```
<212> TYPE: PRT
<213> ORGANISM: Penicillium chrysogenum

<400> SEQUENCE: 13

Met Ala Asp Ser Ser Met Tyr Asn Thr Met Gly Gln Gly Ser Ser Glu
1               5                   10                  15

Asp Pro Ser Asn Pro Gln Tyr Met Ala Gln Val Pro Pro Gln Gln Tyr
            20                  25                  30

Pro Ala Gly Tyr Pro Pro Thr Ala Ala Pro Leu Gln Pro Gly Ala Pro
        35                  40                  45

Tyr Ala Asn Pro Ala Pro Asn Gln Trp Pro Ala Tyr Gly Ser Pro Gln
    50                  55                  60

Gln Pro Gly Met Ala Ser Pro Gly Ile Ala Tyr Asn Ala Pro Gln Gln
65                  70                  75                  80

Pro Met Gly Ala Ala Val Asp Pro Gly Met Ala Gly Leu Ala Ser Gln
                85                  90                  95

Met Gly Gly Leu Asp Ile Ala Ala Asp Ala Gly Ala Arg Thr His Arg
            100                 105                 110

Lys Lys His Arg His Ala His His Asp Ile Gly Gly Ala Ala Pro
        115                 120                 125

Pro Ala Gln Gly Phe Asn Thr Gly Met Asp Gln Gly Leu Gln Gln
    130                 135                 140

Pro Gln Pro Gln Gln Ser Gln Phe Leu Asn Thr Gly Leu Asn Gln
145                 150                 155                 160

His Ala Asp Arg Pro Val Ser Pro Ala Val Gly Leu Val Ser Gly Gln
                165                 170                 175

Ser Val Ala Ala Ile Pro Gly Ile Gln Ser Gly Ala Gly Ser Val Pro
            180                 185                 190

Thr Ser Gly Arg Ile Asp Pro Glu His Ile Pro Ser Ile Pro Arg Ser
        195                 200                 205

Arg Asp Leu Pro Ala Gln Tyr Tyr Phe Asn His Val Tyr Pro Thr Met
    210                 215                 220

Asp Gln His Leu Pro Pro Ala Ala Ile Pro Phe Val Ala Gln Asp
225                 230                 235                 240

Gln Gly Asn Ser Ser Pro Lys Tyr Ala Arg Leu Thr Leu Asn Asn Ile
                245                 250                 255

Pro Ser Ala Ser Asp Phe Leu Thr Ser Thr Gly Leu Pro Leu Gly Met
            260                 265                 270

Ile Leu Gln Pro Leu Ala Pro Leu Asp Pro Gly Glu Gln Pro Ile Pro
        275                 280                 285

Val Leu Asp Phe Gly Asp Val Gly Pro Pro Arg Cys Arg Arg Cys Arg
    290                 295                 300

Thr Tyr Ile Asn Pro Phe Met Ser Phe Arg Ser Gly Gly Ser Lys Phe
305                 310                 315                 320

Val Cys Asn Met Cys Thr Phe Pro Asn Asp Thr Pro Glu Tyr Phe
                325                 330                 335

Ala Pro Leu Asp Pro Ser Gly Ala Arg Val Asp Arg Met Gln Arg Pro
            340                 345                 350

Glu Leu Leu Met Gly Thr Val Glu Phe Thr Val Pro Lys Glu Tyr Trp
        355                 360                 365

Asn Lys Glu Pro Val Gly Leu Gln Thr Leu Phe Leu Ile Asp Val Ser
    370                 375                 380

Arg Glu Ser Val His Arg Gly Phe Leu Lys Gly Val Cys Ala Gly Ile
385                 390                 395                 400
```

```
Lys Asp Ala Leu Tyr Gly Asp Asp Lys Ala Ser Glu Gly Thr Glu
            405             410             415

Gly Asp Gly Ser Ser Arg Lys Leu Pro Val Gly Ala Lys Val Gly Ile
        420             425             430

Val Thr Tyr Asp Lys Glu Val His Phe Tyr Asn Leu Ala Ala Ala Leu
        435             440             445

Asp Gln Ala Gln Met Met Val Met Thr Asp Leu Asp Glu Pro Phe Val
    450             455             460

Pro Leu Ser Glu Gly Leu Phe Val Asp Pro Tyr Glu Ser Lys Ser Val
465             470             475             480

Ile Thr Ser Leu Leu Ser Arg Ile Pro Lys Ile Phe Ser Ile Lys
            485             490             495

Asn Pro Glu Ser Ala Leu Leu Pro Thr Leu Asn Ser Ala Leu Ser Ala
            500             505             510

Leu Gln Ala Thr Gly Gly Lys Ile Val Cys Ala Val Ala Ser Leu Pro
        515             520             525

Thr Cys Gly Pro Gly His Leu Ala Ile Arg Glu Asp Pro Lys Val His
    530             535             540

Gly Thr Asp Ala Glu Arg Lys Leu Phe Thr Thr Glu Asn Pro Ala Trp
545             550             555             560

Lys Lys Thr Ala Ser Lys Leu Ala Glu Ala Gly Val Gly Leu Asp Leu
            565             570             575

Phe Met Ala Ala Pro Gly Gly Thr Tyr Leu Asp Val Ala Thr Ile Gly
        580             585             590

His Val Ser Ser Leu Thr Gly Gly Glu Thr Phe Phe Tyr Pro Asn Phe
        595             600             605

His Ala Pro Arg Asp Leu Leu Lys Leu Arg Lys Glu Ile Ala His Ala
    610             615             620

Val Thr Arg Glu Thr Gly Tyr Gln Thr Leu Met Lys Val Arg Cys Ser
625             630             635             640

Asn Gly Leu Gln Val Ser Ala Tyr His Gly Asn Phe Val Gln His Thr
            645             650             655

Leu Gly Ala Asp Leu Glu Ile Ala Gly Val Asp Ala Asp Lys Ala Val
        660             665             670

Gly Val Leu Phe Ser Tyr Asp Gly Lys Leu Asp Pro Lys Leu Asp Ala
        675             680             685

His Phe Gln Ala Ala Leu Leu Tyr Thr Ser Ala Asp Gly Gln Arg Arg
    690             695             700

Val Arg Cys Ile Asn Val Val Ala Ala Val Asn Glu Gly Gly Leu Glu
705             710             715             720

Thr Met Lys Phe Val Asp Gln Asp Ala Val Val Ser Val Ile Ala Lys
            725             730             735

Glu Ala Ala Ser Lys Thr Leu Asp Lys Asn Leu Lys Asp Ile Arg Ala
        740             745             750

Ser Ile Ser Glu Lys Thr Val Asp Ile Phe Ser Gly Tyr Arg Lys Ile
        755             760             765

Phe Ser Gly Ser His Pro Pro Gly Gln Leu Val Leu Pro Glu Asn Leu
    770             775             780

Lys Glu Phe Ser Met Tyr Met Leu Ser Leu Val Lys Ser Arg Ala Phe
785             790             795             800

Lys Ala Gly Pro Glu Ser Ser Asp Arg Arg Ile His Asp Met Arg Leu
            805             810             815
```

-continued

```
Ile Arg Ser Met Gly Cys Thr Glu Met Ala Leu Tyr Leu Tyr Pro Arg
                820                 825                 830

Ile Ile Pro Val His Asn Met Gln Pro Glu Asp Gly Phe Ala Asn Glu
            835                 840                 845

His Gly Gln Leu Gln Ile Pro Pro Thr Met Arg Ala Ser Tyr Ser Arg
        850                 855                 860

Ile Glu Asp Gly Gly Val Tyr Ile Val Asp Asn Gly Gln Ala Ile Leu
865                 870                 875                 880

Leu Trp Ile His Ala Gln Val Ser Pro Asn Leu Leu Glu Asp Leu Phe
                885                 890                 895

Gly Pro Gly His Asn Ser Leu Gln Gly Leu Asn Pro Asn Thr Ser Ser
            900                 905                 910

Leu Pro Val Leu Glu Thr His Leu Asn Ala Gln Val Arg Asn Leu Leu
        915                 920                 925

Gln Tyr Leu Ser Thr Val Arg Gly Ser Lys Ser Val Thr Ile Gln Leu
930                 935                 940

Ala Arg Gln Gly Leu Asp Gly Ala Glu Tyr Glu Phe Ala Arg Leu Leu
945                 950                 955                 960

Leu Glu Asp Arg Asn Asn Glu Ala Gln Ser Tyr Val Asp Trp Leu Val
                965                 970                 975

His Ile His Arg Gln Ile Asn Leu Glu Leu Ala Gly His Arg Lys Lys
            980                 985                 990

Glu Glu Gly Gly Glu Gly Ala Leu  Ala Ser Leu Ser Ala Met Arg Thr
        995                 1000                1005

Pro Tyr Trp
    1010
```

<210> SEQ ID NO 14
<211> LENGTH: 1052
<212> TYPE: PRT
<213> ORGANISM: Neurospora crassa

<400> SEQUENCE: 14

```
Met Ala Asp Tyr Thr Met Tyr His Ala Leu Gly Gln Gly Glu Thr Leu
1               5                   10                  15

Asp Pro Asn Asp Pro Asn Arg Thr Thr Gln Pro Ala Pro Gln Phe
                20                  25                  30

Gln Pro Pro Val Ala Pro Asn Pro Tyr His Pro Gly Ala Glu Tyr Asn
            35                  40                  45

Ala Pro Gly Gln Gln Gln Gln Gln Gln Tyr Gly Gln Gln Tyr
        50                  55                  60

Gly Gln Gln Tyr Gly Gln Gln Tyr Gly Gln Gln Tyr Gly Gln Glu
65                  70                  75                  80

Tyr Gly His Gln Gln Gln Gln Gln Gln Tyr Gly Ala Pro
                85                  90                  95

Ser Pro Tyr Gly Ala Pro Pro Ala His Ser Pro Val Ser Pro Met Asp
            100                 105                 110

Asp Val Gly Leu Ala Ala Gln Met Gly Gly Met Ser Leu Gly Ala Gly
        115                 120                 125

Ala Gly Ala Ala Asp His His Gly Arg Lys Lys Lys Asp Arg His
130                 135                 140

Ala Phe His Thr Val Glu Ala Pro Ala Gly Ser Ser Gln Pro Phe Asn
145                 150                 155                 160

Gly Met Pro Pro Ala Gly Ile Pro Ala Thr Gln Phe Leu Asn Ala Asp
                165                 170                 175
```

-continued

Pro Ser Leu Ala Gly Arg Ile Pro Gly Pro His Gly Gln Phe Pro
            180                 185             190

Met Pro Ala Ser Pro Ala Phe Gly Pro Val Pro Thr Ser Ala Ala Asp
        195                 200             205

Phe Ala Ala Arg Asp Ala Thr Gln Gly Val Gly Ser Gly Val Phe Ala
    210                 215                 220

Ala Gly Gly Pro Gln Gly Gly Lys Pro Ser Pro Asp Asp Thr Pro Ser
225                 230             235                 240

Val Pro Leu Ser Arg Asp Ala Val Gln Pro Tyr Phe His Thr Asn Val
                245                 250                 255

Tyr Pro Thr Phe Glu Arg Leu Val Pro Pro Ala Val Thr Ser Phe
            260                 265             270

Val Ala Leu Asp Gln Gly Asn Ser Ser Pro Lys Phe Ala Arg Leu Thr
        275                 280             285

Met Thr Asn Leu Pro Ala Ser Ala Glu Gly Leu Lys Ser Thr Gly Leu
    290                 295                 300

Pro Leu Gly Leu Leu Leu Gln Pro Leu Ala Glu Thr Gln Pro Gly Glu
305                 310             315                 320

Leu Pro Ile Pro Val Leu Asp Phe Gly Glu Gln Gly Pro Pro Arg Cys
                325                 330                 335

His Arg Cys Arg Ala Tyr Met Asn Pro Phe Met Met Phe Lys Ala Gly
            340                 345             350

Gly Asn Lys Phe Val Cys Asn Leu Cys Thr Tyr Ala Asn Asp Thr Pro
        355                 360             365

Pro Glu Tyr Phe Cys Ala Leu Ser Pro Gln Gly Val Arg Val Asp Arg
    370                 375                 380

Asp Gln Arg Pro Glu Leu Thr Arg Gly Thr Val Glu Phe Val Val Pro
385                 390             395                 400

Lys Glu Tyr Trp Thr Lys Glu Pro Val Gly Met Arg Tyr Leu Phe Val
                405                 410                 415

Ile Asp Val Thr Gln Glu Ser Tyr Asn Lys Gly Phe Leu Glu Ser Phe
            420                 425             430

Cys Glu Gly Ile Leu Ser Ala Leu Tyr Gly Gly Ser Glu Glu Gly Glu
        435                 440             445

Asp Gln Asp Glu Thr Gly Glu Pro Lys Arg Lys Ile Pro Ala Gly Ala
    450                 455                 460

Lys Val Gly Phe Val Thr Phe Asp Gln Glu Ile His Phe Tyr Asn Val
465                 470             475                 480

Ser Pro Ala Leu Glu Gln Ala Gln Met Ile Val Met Pro Asp Ile Glu
                485                 490                 495

Asp Pro Phe Leu Pro Leu Ser Asp Gly Leu Phe Val Asp Pro Tyr Glu
            500                 505             510

Ser Lys Ala Val Ile Ser Ser Leu Leu Thr Arg Leu Pro Gln Met Phe
        515                 520             525

Ser Asn Ile Lys Asn Pro Glu Pro Ala Leu Leu Ser Ala Leu Asn Ser
    530                 535                 540

Ala Val Ala Ala Leu Glu Lys Thr Gly Gly Lys Val Phe Cys Ser Leu
545                 550             555                 560

Ala Ala Leu Pro Thr Trp Gly Pro Gly Arg Leu Phe Met Arg Asp Asp
                565                 570                 575

Gly Lys His Pro Gly Glu Pro Asp Lys Lys Leu Phe Thr Thr Glu
            580                 585             590

His Pro Gly Trp Arg Lys Leu Ala Glu Lys Met Val Ser Leu Gly Val
            595                 600                 605

Gly Ala Asp Phe Phe Met Ala Ser Pro Ser Gly Gly Tyr Leu Asp Ile
        610                 615                 620

Ala Thr Ile Gly His Val Ser Ser Thr Gly Gly Glu Thr Phe Phe
625                 630                 635                 640

Tyr Pro Asn Phe Val Val Gln Arg Asp Ser Thr Lys Leu Ser Leu Glu
                645                 650                 655

Ile His His Ala Val Arg Arg Glu Thr Gly Tyr Ala Ala Leu Met Lys
            660                 665                 670

Val Arg Cys Ser Asn Gly Leu Gln Val Asn Ala Tyr His Gly Asn Phe
        675                 680                 685

Ile Gln His Thr Phe Gly Ala Asp Leu Glu Ile Gly Val Ile Asp Ala
    690                 695                 700

Asp Lys Ala Leu Ala Val Thr Phe Gly Tyr Asp Gly Lys Leu Asp Ser
705                 710                 715                 720

Lys Leu Asp Ala His Phe Gln Ala Ala Leu Leu Tyr Thr Thr Ala Ser
                725                 730                 735

Gly Gln Arg Arg Val Arg Cys Ile Asn Val Ile Ala Gly Val Ser Asp
            740                 745                 750

Leu Ala Arg Asp Cys Met Lys Tyr Ile Asp Gln Asp Ala Ile Val Ser
        755                 760                 765

Ile Leu Ala Lys Glu Ala Ser Thr Lys Leu Ser Thr Thr Ser Ala Asn
    770                 775                 780

Leu Lys Glu Val Arg Ser Ser Leu Thr Glu Lys Thr Ile Asp Ile Leu
785                 790                 795                 800

Ala Leu Tyr Arg Lys Asn His Leu Ala Val Pro His Pro Pro Gln Gln
                805                 810                 815

Leu Val Met Pro Glu Arg Leu Lys Glu Phe Thr Met Tyr Val Leu Gly
            820                 825                 830

Met Leu Lys Cys Arg Ala Phe Lys Gly Gly Asn Glu Thr Thr Asp Arg
        835                 840                 845

Arg Val His Asp Met Arg Leu Ile Arg Ser Met Gly Ala Arg Glu Leu
850                 855                 860

Ser Leu Tyr Leu Tyr Pro Arg Ile Ile Pro Leu His Ser Leu Gln Pro
865                 870                 875                 880

Glu Asp Gly Tyr Pro Asp Ala Thr Thr Gly His Leu Arg Met Pro Ser
                885                 890                 895

Thr Met Arg Ala Ser Phe Ala Arg Val Glu Pro Gly Gly Val Tyr Leu
            900                 905                 910

Val Asp Asn Gly Gln Val Cys Leu Leu Trp Met His Ala Gln Thr Ala
        915                 920                 925

Pro Ala Leu Ile Gln Asp Leu Phe Gly Glu Asp Lys Thr Thr Leu Gln
    930                 935                 940

Ser Leu Asp Pro Tyr Thr Ser Thr Ile Pro Val Leu Glu Thr His Leu
945                 950                 955                 960

Asn Ala Gln Thr Arg Asn Ile Ile Glu Tyr Met Arg Thr Val Arg Gly
                965                 970                 975

Ser Lys Gly Leu Thr Ile Gln Leu Ala Arg Gln Gly Ile Asp Gly Ala
            980                 985                 990

Glu Phe Glu Phe Ala Arg Met Leu Val Glu Asp Arg Asn Asn Glu Ala
        995                 1000                1005

Gln Ser Tyr Val Asp Trp Leu Val His Val His Lys Gly Val Gln

```
              1010                1015                1020
Leu Glu Leu Ala Gly Gln Arg Lys Arg Glu Asp Gly Glu Ser His
        1025                1030                1035

Ser Ala Leu Gly Ser Phe Thr Gly Leu Arg Pro Ala Tyr Trp
        1040                1045                1050

<210> SEQ ID NO 15
<211> LENGTH: 1038
<212> TYPE: PRT
<213> ORGANISM: Fusarium oxysporum

<400> SEQUENCE: 15

Met Ala Asp Tyr Ala Gln Tyr His Ala Leu Gly Gln Gly Glu Val Ile
1               5                   10                  15

Asp Pro Asn Asp Pro Asn Arg Thr Ser Gln Pro Ser Ala Gln Gln Phe
            20                  25                  30

Gln Pro Pro Ile Ala Pro Ser Pro Tyr Gln Gln Ala Ser Pro Tyr
        35                  40                  45

Gly Ala Pro Gln Tyr Leu Gly Gly Gln Gln Ala Pro Pro Met Thr
    50                  55                  60

Gly Ser Pro Ala Pro Ala Pro Gly Tyr Gly Tyr Ala Pro Pro Gln Ala
65                  70                  75                  80

Gln Ala Pro Pro Gly Gln Ala Pro Pro Ser Gln Asp Ala Thr Leu Ala
                85                  90                  95

Ala Gln Leu Gly Gly Met Asn Leu Gly Asp Gly His Gly Thr Ala Arg
            100                 105                 110

Arg Lys Lys Lys Asp Arg His Ala Tyr His Thr Val Glu Pro Thr Gly
        115                 120                 125

Ser Ser Gln Ala Phe Asn Gly Met Pro Pro Gln Gly Thr Ser Ala Thr
    130                 135                 140

Gln Phe Leu Asp Ser Val Pro Gly Gly Pro Gly Phe Gly Gly Gln Phe
145                 150                 155                 160

Gly Ser Pro Gln Gly Thr Pro Gln Met Gln Ser Gln Ser Gln Phe Ser
                165                 170                 175

Ala Pro Val Asn Pro Ala Phe Gly Pro Gly Pro Val Ala Gly Thr Pro
            180                 185                 190

Gly Val Gly Glu Gly Leu Gly Thr Ala Ser Val Ser Thr Ser Gly Pro
        195                 200                 205

Lys Gly Val Ser Pro Asp Asp Met Pro Ser Val Pro Ala Ser Arg Asp
    210                 215                 220

Ala Ile Gln Gln Tyr Tyr Leu Lys Asn Val Tyr Pro Thr Phe Glu Arg
225                 230                 235                 240

His Val Pro Pro Pro Ser Thr Val Ser Phe Val Ala Tyr Asp Gln Gly
                245                 250                 255

Asn Ser Ser Pro Lys Tyr Thr Arg Leu Thr Leu Asn Asn Ile Pro Thr
            260                 265                 270

Thr Gln Asp Ala Leu Gln Ala Thr Gly Leu Ser Leu Gly Leu Leu Leu
        275                 280                 285

Gln Pro Leu Ala Pro Leu Gln Ala Gly Glu Ala Glu Ile Pro Val Leu
    290                 295                 300

Asp Phe Gly Glu Ala Gly Pro Pro Arg Cys Arg Cys Arg Ala Tyr
305                 310                 315                 320

Met Asn Pro Phe Met Met Phe Arg Ser Gly Gly Asn Lys Phe Val Cys
                325                 330                 335
```

Asn Leu Cys Ala Tyr Pro Asn Asp Thr Pro Pro Glu Tyr Phe Ser Ala
                340                 345                 350

Thr Asn Pro Gln Gly Val Arg Val Asp Arg Asp Thr Arg Pro Glu Leu
            355                 360                 365

His Arg Gly Thr Val Glu Phe Val Val Pro Lys Glu Tyr Trp Thr Arg
        370                 375                 380

Glu Pro Val Gly Leu Arg Trp Leu Phe Leu Ile Asp Val Thr Gln Glu
385                 390                 395                 400

Ser Tyr Asn Lys Gly Tyr Val Glu Ala Phe Cys Glu Gly Ile Arg Val
                405                 410                 415

Ala Leu Tyr Gly Gly Glu Asp Gln Glu Leu Asp Glu Asn Gly Glu Pro
            420                 425                 430

Lys Arg Arg Ile Pro Glu Gly Ala Lys Val Gly Phe Val Thr Tyr Asp
        435                 440                 445

Lys Asp Ile His Phe Tyr Asn Val Asn Pro Ala Leu Asp Gln Ala Gln
        450                 455                 460

Met Met Ile Met Pro Asp Leu Glu Asp Pro Phe Val Pro Leu Ser Glu
465                 470                 475                 480

Gly Leu Phe Val Asp Pro Tyr Glu Ser Lys Asp Val Ile Thr Ser Leu
                485                 490                 495

Leu Thr Arg Leu Pro Asp Met Phe Ser Thr Ile Lys Asn Pro Glu Pro
            500                 505                 510

Ala Leu Leu Ala Ala Leu Asn Ser Ala Leu Ala Ala Leu Glu Ala Thr
        515                 520                 525

Gly Gly Lys Val Val Ala Ser Cys Ser Ala Leu Pro Thr Trp Gly Pro
530                 535                 540

Gly Arg Leu Phe Met Arg Asp Asn Gly Asn His Pro Gly Gly Glu Ile
545                 550                 555                 560

Asp Lys Lys Leu Tyr Thr Thr Glu His Pro Ala Trp Lys Lys Val Ala
                565                 570                 575

Glu Lys Met Ala Ala Ser Gly Val Gly Ala Asp Phe Phe Leu Ala Ala
            580                 585                 590

Pro Ser Gly Gly Tyr Leu Asp Ile Ala Thr Ile Gly His Val Ser Ser
        595                 600                 605

Thr Thr Gly Gly Glu Thr Phe Tyr Tyr Pro Asn Phe Ile Ala Ala Arg
        610                 615                 620

Asp Ser Arg Lys Leu Ser Leu Glu Ile Ser His Ala Val Thr Arg Glu
625                 630                 635                 640

Thr Gly Phe Gln Ala Leu Met Lys Val Arg Cys Ser Asn Gly Leu Gln
                645                 650                 655

Val Ser Gly Tyr His Gly Asn Phe Ile Gln His Thr Phe Gly Ala Asp
            660                 665                 670

Leu Glu Ile Gly Val Ile Asp Ala Asp Lys Ala Met Gly Val Ser Phe
        675                 680                 685

Ser Tyr Asp Gly Lys Leu Asp Pro Lys Leu Asp Ala His Phe Gln Ser
        690                 695                 700

Ala Leu Leu Tyr Thr Thr Ala Ser Gly Glu Arg Arg Val Arg Cys Ser
705                 710                 715                 720

Asn Val Ile Ala Ser Val Thr Glu Thr Ser Lys Glu Ser Gly Ala Arg
                725                 730                 735

Glu Gln Gly Ile Arg Glu Cys Leu Lys Phe Val Asp Gln Asp Ala Val
            740                 745                 750

Ile Gly Met Leu Ala Lys Glu Ala Ser Thr Lys Leu Ala Thr Thr Ser

```
            755                 760                 765
Ser Asn Leu Lys Asp Ile Arg His Trp Leu Ser Glu Lys Ala Ile Asp
    770                 775                 780

Val Leu Ala Cys Tyr Arg Lys His Ala Ala Gln Gln His Pro Pro Gly
785                 790                 795                 800

Gln Leu Val Met Pro Glu Arg Leu Lys Glu Tyr Cys Met Tyr Leu Leu
                805                 810                 815

Gly Leu Leu Lys Cys Arg Ala Leu Lys Gly Val Glu Asn Ser Asp
                820                 825                 830

Arg Arg Val His Glu Met Arg Met Leu Arg Ser Met Gly Ala Leu Glu
                835                 840                 845

Leu Ser Leu Tyr Leu Tyr Pro Arg Met Ile Pro Ile His Asn Leu Ala
    850                 855                 860

Pro Glu Glu Gly Phe Ala Asp Pro Glu Thr Gly His Leu Lys Met Pro
865                 870                 875                 880

Pro Ala Ile Arg Thr Ser Phe Ser Arg Val Glu Pro Gly Gly Val Tyr
                885                 890                 895

Leu Val Asp Asn Gly Gln Gln Cys Leu Leu Trp Phe His Ser Gln Thr
                900                 905                 910

Ser Pro Asn Leu Ile Ser Asp Leu Phe Gly Glu Asp Lys Asp Ser Leu
                915                 920                 925

Lys Ser Leu Asp Pro Tyr Thr Ser Ala Leu Pro Leu Leu Glu Thr His
    930                 935                 940

Leu Asn Ala Gln Val Arg Asn Ile Ile Glu Phe Leu Arg Thr Met Arg
945                 950                 955                 960

Gly Ser Lys Gly Leu Thr Ile Gln Leu Ala Arg Gln Gly Ile Asp Gly
                965                 970                 975

Ala Glu Phe Asp Phe Ala Arg Met Leu Val Glu Asp Arg Asn Asn Glu
                980                 985                 990

Ala Gln Ser Tyr Val Asp Trp Leu Val His Ile His Lys Gly Val Gln
                995                 1000                1005

Leu Glu Leu Ser Gly Gln Arg Lys Lys Glu Gly Glu Glu His Thr
    1010                1015                1020

Ala Ala Ser Leu Ser Asn Phe Ala Gly Leu Arg Pro Ala Tyr Trp
    1025                1030                1035

<210> SEQ ID NO 16
<211> LENGTH: 34
<212> TYPE: PRT
<213> ORGANISM: Artificial Sequence
<220> FEATURE:
<223> OTHER INFORMATION: synthetic consensus sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
```

```
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 16

Ile Gln Leu Ala Arg Gln Gly Xaa Asp Gly Xaa Glu Xaa Xaa Xaa Ala
1               5                   10                  15

Arg Xaa Leu Xaa Glu Asp Arg Asn Xaa Glu Ala Xaa Ser Xaa Val Asp
            20                  25                  30

Trp Leu

<210> SEQ ID NO 17
<211> LENGTH: 29
<212> TYPE: DNA
<213> ORGANISM: Artificial Sequence
<220> FEATURE:
<223> OTHER INFORMATION: synthesized primer

<400> SEQUENCE: 17
ttcctgacaa cgaggacatc tcaagctgt                                      29

<210> SEQ ID NO 18
<211> LENGTH: 26
<212> TYPE: DNA
<213> ORGANISM: Artificial Sequence
<220> FEATURE:
<223> OTHER INFORMATION: synthesized primer

<400> SEQUENCE: 18
caaacatagc agcgtccatt gcacga                                         26

<210> SEQ ID NO 19
<211> LENGTH: 56
<212> TYPE: DNA
<213> ORGANISM: Artificial Sequence
<220> FEATURE:
<223> OTHER INFORMATION: synthesized primer

<400> SEQUENCE: 19
ggggacaagt ttgtacaaaa aagcaggctt gatggttgac tattgggttt ctgtgc        56

<210> SEQ ID NO 20
<211> LENGTH: 18
<212> TYPE: DNA
<213> ORGANISM: Artificial Sequence
<220> FEATURE:
<223> OTHER INFORMATION: synthesized primer

<400> SEQUENCE: 20
gtcgcccgtc tccgttgt                                                  18

<210> SEQ ID NO 21
<211> LENGTH: 27
<212> TYPE: DNA
<213> ORGANISM: Artificial Sequence
<220> FEATURE:
<223> OTHER INFORMATION: synthesized primer
```

```
<400> SEQUENCE: 21
gctttcgagc tcacacgaca tccttca                                              27

<210> SEQ ID NO 22
<211> LENGTH: 19
<212> TYPE: DNA
<213> ORGANISM: Artificial Sequence
<220> FEATURE:
<223> OTHER INFORMATION: synthesized primer

<400> SEQUENCE: 22
tccccgagac gccaaacga                                                       19

<210> SEQ ID NO 23
<211> LENGTH: 20
<212> TYPE: DNA
<213> ORGANISM: Artificial Sequence
<220> FEATURE:
<223> OTHER INFORMATION: synthesized primer

<400> SEQUENCE: 23
ggccgaggac ccttccatca                                                      20

<210> SEQ ID NO 24
<211> LENGTH: 27
<212> TYPE: DNA
<213> ORGANISM: Artificial Sequence
<220> FEATURE:
<223> OTHER INFORMATION: synthesized primer

<400> SEQUENCE: 24
cccctccgga tgaggtggct tgtggct                                              27

<210> SEQ ID NO 25
<211> LENGTH: 32
<212> TYPE: DNA
<213> ORGANISM: Artificial Sequence
<220> FEATURE:
<223> OTHER INFORMATION: synthesized primer

<400> SEQUENCE: 25
ggcggctagc agacgcactc gtagagcaag gt                                        32

<210> SEQ ID NO 26
<211> LENGTH: 25
<212> TYPE: DNA
<213> ORGANISM: Artificial Sequence
<220> FEATURE:
<223> OTHER INFORMATION: synthesized primer

<400> SEQUENCE: 26
aggtccgatc aacgactctg gcaac                                                25

<210> SEQ ID NO 27
<211> LENGTH: 29
<212> TYPE: DNA
<213> ORGANISM: Artificial Sequence
<220> FEATURE:
<223> OTHER INFORMATION: synthesized primer

<400> SEQUENCE: 27
ttcctgacaa cgaggacatc tcaagctgt                                            29

<210> SEQ ID NO 28
```

```
<211> LENGTH: 28
<212> TYPE: DNA
<213> ORGANISM: Artificial Sequence
<220> FEATURE:
<223> OTHER INFORMATION: synthesized primer

<400> SEQUENCE: 28
gggttgtcgt tagctaacca gagcgtaa                                          28

<210> SEQ ID NO 29
<211> LENGTH: 36
<212> TYPE: DNA
<213> ORGANISM: Artificial Sequence
<220> FEATURE:
<223> OTHER INFORMATION: synthesized primer

<400> SEQUENCE: 29
ggtcagtaac atagcaggac tatagtagtg gctcac                                 36

<210> SEQ ID NO 30
<211> LENGTH: 33
<212> TYPE: DNA
<213> ORGANISM: Artificial Sequence
<220> FEATURE:
<223> OTHER INFORMATION: synthesized primer

<400> SEQUENCE: 30
agatactagt gcgaggcatc cgtgatggat ctc                                    33

<210> SEQ ID NO 31
<211> LENGTH: 32
<212> TYPE: DNA
<213> ORGANISM: Artificial Sequence
<220> FEATURE:
<223> OTHER INFORMATION: synthesized primer

<400> SEQUENCE: 31
gggtcccggg ctcgggagcg taactcttgt cc                                     32

<210> SEQ ID NO 32
<211> LENGTH: 23
<212> TYPE: DNA
<213> ORGANISM: Artificial Sequence
<220> FEATURE:
<223> OTHER INFORMATION: synthesized primer

<400> SEQUENCE: 32
cgccgtcagt tgacgacagt gct                                               23

<210> SEQ ID NO 33
<211> LENGTH: 29
<212> TYPE: DNA
<213> ORGANISM: Artificial Sequence
<220> FEATURE:
<223> OTHER INFORMATION: synthesized primer

<400> SEQUENCE: 33
ttcctgacaa cgaggacatc tcaagctgt                                         29

<210> SEQ ID NO 34
<211> LENGTH: 23
<212> TYPE: DNA
<213> ORGANISM: Artificial Sequence
<220> FEATURE:
<223> OTHER INFORMATION: synthesized primer

<400> SEQUENCE: 34
```

```
caccggtgaa gccttccgtg agt                                                    23
```

<210> SEQ ID NO 35
<211> LENGTH: 36
<212> TYPE: DNA
<213> ORGANISM: Artificial Sequence
<220> FEATURE:
<223> OTHER INFORMATION: synthesized primer

<400> SEQUENCE: 35

```
ggtcagtaac atagcaggac tatagtagtg gctcac                                      36
```

<210> SEQ ID NO 36
<211> LENGTH: 24
<212> TYPE: DNA
<213> ORGANISM: Artificial Sequence
<220> FEATURE:
<223> OTHER INFORMATION: synthesized primer

<400> SEQUENCE: 36

```
ggagccaaca gagacggtca ggtt                                                   24
```

<210> SEQ ID NO 37
<211> LENGTH: 23
<212> TYPE: DNA
<213> ORGANISM: Artificial Sequence
<220> FEATURE:
<223> OTHER INFORMATION: synthesized primer

<400> SEQUENCE: 37

```
gcccagcgtc gagtgagaca agt                                                    23
```

<210> SEQ ID NO 38
<211> LENGTH: 2630
<212> TYPE: DNA
<213> ORGANISM: Trichoderma reesei

<400> SEQUENCE: 38

```
ggcaaggcgt acgcatgagc ggagcggcag taggtacttg cgcctccgtg ctcatctgct            60
gcccgcagcg cgtaccggcg tcgtgacatc tggacacctc gttcgtccct actttagatc           120
catccagccc gaacctcatt ttcctctctc cttttccctt ccatcctccc gcaaccaccg           180
cgtcttttct tccctcccga gccgacactc gagtctctgc cctgcgagca ttgcaccgtc           240
gctcgttctt ctctacgctc actatccaac atactagttt attctttttc ccttcttcta           300
ccatcttctg cctctttact tacgaaatca aaccccccc tttaaaacat ccacgaatct            360
cctttgcact tcagcttcgt cgcatacatt caccatgaag ggtaggtgac gcgccggttc           420
cccaatctgc ccatcattgg cttcactcca gctccaatgg caagatctcg ctgacaatct           480
ctctcccctg cgcaggactt attcttgtcg gcggctttgg cactcgcctt cgccctctcg           540
tacgtccacg ccagcaccac cagcagcgat ccgacctgca tcccactacc gcattgacgc           600
ggatggggtg gcatggaggg ggaaaaccac cataagcgca gcctctcaca cccgcgaacc           660
tccactgacc attgtgcgac gccaatctag accctgacgc tccccaagcc tctggttgag           720
ttctgcaaca agcccatgat tgtgcaccag atcgaggctc tcgtcgccgc tggcgtgacc           780
gacattgtcc tcgccgtcaa ctaccgccca gaaatcatgg aaaagttcct ggccgaggtg           840
agtcgtgcac atcacaccct atgcccctc actacaaacc cttgcctatt cgcctgccca           900
ttcgctgtac caagcttttc gccccccccc cccccccct cccctcccct cctactcagc           960
```

-continued

```
atatctcccc cccaccaatg acaatggacg caaaggctga ttgcgtacgc tcgaccgttt    1020
agtacgagga gaaatacaac atcaacattg agttctccgt cgagtcggag cccctcgaca    1080
ccgccggccc cctcaagctt gctgagcgca tcctcggcaa ggatgactcg cccttcttcg    1140
tcctcaactc cgacgtcatc tgcgactatc ccttcaagga gctcctcgag ttccacaagg    1200
cccacggcga tgagggcacc attgtcgtca ccaaggtcga ggagccgtcc aagtacggtg    1260
tcgtcgtcca caagcccaac caccctcgc gcatcgaccg cttcgtcgag aagcccgtcg    1320
agttcgtcgg caaccgcatc aacgccggca tgtacatctt caaccctcc gtcctgaagc    1380
gcatcgagct tcgccccacg tcgatcgaga aggagacgtt ccccgccatg gttgccgaca    1440
accagctgca ctcgttcgat ctcgagggct tctggatgga cgttggccag cccaaggact    1500
tcctcagcgg cacctgcctg tacctgtcct ccctcaccaa gaagggcagc aaggagctga    1560
ccctcccac cgagccctac gttcacggcg gcaacgtcat gattcaccct tcggccaaga    1620
ttggaaagaa ctgcagaata ggccccaatg tcaccattgg cccggatgtt gtcgtcggtg    1680
acggcgtccg cctgcagcga tgcgtcctcc tcaagggctc caaggtcaag gaccacgcct    1740
gggtcaagtc gacgattgtt ggctggaaca gcaccgtcgg tcgctgggcc cgtctcgaga    1800
atgtgactgt tctcggtgac gacgtgacca ttggcgacga gatttacgtc aacgcggca    1860
gcgtcctgcc tcacaagtcc atcaaggcca acgttgacgt tcccgccatc attatgtgat    1920
ttatctcatg ttgtcacgca tccttggctc gcatgggcgt ttttgttccc catgcgctgc    1980
tttccgagat gatctttgtt tcttcttcaa accccatctt ttcttctttt aacttgacat    2040
ttctcttttt tttttttttt tccttttaca gaaccccatt tacgccttac cgcaaactca    2100
ccactcctcc gctattctca agagataccc tatattggtg ggggaaacag tctttgagag    2160
aaaagaaaac caagccacat tttatataat tactactagt ctcgacatct tttttccctt    2220
tcttcttctt cctcaagaaa aaagatgtcg tgtacactta tgttgagccc caagtaaatc    2280
gtttggcgtc tcggggaacc ggttggcaaa gcattcttgg agggacaggg acgagggctg    2340
agggttgaga agagcaatga cggacgaggc actcaagatt tccatgtatg aaaagatgat    2400
agcgtagcga atgaagtgta tttacgcttg cgccgactgt gttgtctggt gacgcgattg    2460
ctgaggtcga gcttgtccag tacgagcact gcttgaagat gaacaaatcg aggtggttcc    2520
cccataggct gaccttatac agaatttcgc tatgcatcag aagtaagtcg ttatcacatt    2580
tgatgagata gcatctccgc tcacttgtca tttcagttag aatattcatt                2630
```

FILAMENTOUS FUNGI HAVING AN ALTERED VISCOSITY PHENOTYPE

CROSS REFERENCE TO RELATED APPLICATIONS

The present application is a 371 National Stage application of PCT/US2012/034379, filed on Apr. 20, 2012, which claims priority to U.S. Provisional Application Ser. Nos. 61/478,162, and 61/478,160, both filed on Apr. 22, 2011, which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40003-WO_ST25.txt" created on Oct. 11, 2013, which is 106,496 bytes in size.

TECHNICAL FIELD

The present strains and methods relate to genetic mutations in filamentous fungi that give rise to strain variants having altered growth characteristics. Such variants are well-suited for growth in submerged cultures, e.g., for the large-scale production of enzymes and other proteins or metabolites for commercial applications.

BACKGROUND

Filamentous fungi are capable of expressing native and heterologous proteins to high levels, making them well-suited for the large-scale production of enzymes and other proteins for industrial, pharmaceutical, animal health and food and beverage applications. Filamentous fungi are typically grown in mycelial submerged cultures in bioreactors, which are adapted to introduce and distribute oxygen and nutrients into the culture medium (i.e., broth). The morphological characteristics of the mycelium affect the rheological properties of the broth, thereby affecting bioreactor performance.

Generally, the higher the viscosity of the broth, the less uniform the distribution of oxygen and nutrients and the more energy required to agitate the culture. In some cases, the viscosity of the broth becomes sufficiently high to significantly interfere with the dissolution of oxygen and nutrients, thereby adversely affecting the growth of the fungi. Additionally, the power required to mix and aerate viscous broth can significantly increase the cost of production, and incur higher capital expenditures in terms of motors and power supplies.

SUMMARY

Described are strains and methods relating to filamentous fungi having genetic alterations that give rise to altered viscosity phenotypes.

In one aspect, a variant strain of filamentous fungus derived from a parental strain is provided, the variant strain comprising a genetic alteration that causes cells of the variant strain to produce an altered amount of functional Mpg1 protein compared to cells of the parental strain, wherein the cells of the variant strain are produced during aerobic fermentation in submerged culture cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

In some embodiments, the altered amount of functional Mpg1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

In some embodiments, the genetic alteration comprises a disruption of the mpg1 gene present in the parental strain. In some embodiments, disruption of the mpg1 gene is the result of deletion of all or part of the mpg1 gene. In some embodiments, disruption of the mpg1 gene is the result of deletion of a portion of genomic DNA comprising the mpg1 gene. In some embodiments, disruption of the mpg1 gene is the result of mutagenesis of the mpg1 gene.

In some embodiments, disruption of the mpg1 gene is performed using site-specific recombination. In some embodiments, disruption of the mpg1 gene is performed in combination with introducing a selectable marker at the genetic locus of the mpg1 gene.

In some embodiments, the variant strain does not produce functional Mpg1 protein. In some embodiments, the variant strain does not produce Mpg1 protein.

In some embodiments, the variant strain further comprises a gene encoding a protein of interest. In some embodiments, the variant strain further comprises a disruption of the sfb3 gene. In some embodiments, the variant strain further comprises a disruption of the seb1 gene. In some embodiments, the variant strain further comprises a disruption of the sfb3 and seb1 genes. In some embodiments, the variant strain further comprises a disruption of at least one gene selected from the group consisting of the sfb3 gene, the seb1 gene, the gas1 gene, the crz1 gene, and the tps2 gene. In some embodiments, the variant strain produces substantially the same amount of, or more, protein per unit amount of biomass as the parental strain.

In some embodiments, the filamentous fungus is a *Pezizomycotina* species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*. In some embodiments, the filamentous fungus is *Trichoderma reesei*.

In another aspect, a method for producing a variant strain of filamentous fungus cells is provided, comprising: introducing a genetic alteration into a parental strain of filamentous fungal cell, which genetic alteration alters the production of functional Mpg1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the genetic alteration reduces or prevents the production of functional Mpg1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

In some embodiments, the genetic alteration comprises disrupting the mpg1 gene in a parental filamentous fungal cell using genetic manipulation. In some embodiments, the genetic alteration comprises deleting the mpg1 gene in a parental filamentous fungal cell using genetic manipulation. In some embodiments, the genetic alteration is performed using site-specific genetic recombination.

In some embodiments, disruption of the mpg1 gene is performed in combination with introducing a selectable marker at the genetic locus of the mpg1 gene. In some embodiments, disruption of the mpg1 gene is performed in combination with disrupting the sfb3 gene. In some embodiments, disruption of the mpg1 gene is performed in combination with disrupting at least one gene selected from the group consisting of the sfb3 gene, the seb1 gene, the gas1 gene, the crz1 gene, and the tps2 gene.

In some embodiments, the variant strain produces substantially the same amount of, or more, protein per unit amount of biomass as the parental strain.

In some embodiments, the filamentous fungus is a *Pezizomycotina* species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*. In some embodiments, the filamentous fungus is *Trichoderma reesei*.

In some embodiments, the parental strain further comprises a gene encoding a protein of interest. In some embodiments, the gene encoding the protein of interest is present in the parental strain prior to introducing the genetic alteration that reduces or prevents the production of functional Mpg1 protein. In some embodiments the protein of interest within the parental strain is encoded by an endogenous gene or a heterologous gene.

In another aspect, a protein of interest produced by any of the aforementioned variant strains is provided.

In yet another aspect, a filamentous fungus produced by any of the aforementioned methods and having any of the aforementioned properties is provided.

In another aspect, a variant strain of filamentous fungus derived from a parental strain is provided, the variant strain comprising: (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and (b) a gene encoding a protein of interest, wherein the gene encoding the protein of interest is present in the variant strain prior to the genetic alteration in (a).

In some embodiments, the genetic alteration of the resulting variant strain comprises a disruption of the mpg1 gene present in the parental strain. In some embodiments, disruption of the mpg1 gene is performed in combination with introducing a selectable marker at the genetic locus of the mpg1 gene. In some embodiments, disruption of the mpg1 gene is performed in combination with disrupting the sfb3 gene. In some embodiments, disruption of the mpg1 gene is performed in combination with disrupting the seb1 gene. In some embodiments, disruption of the mpg1 gene is performed in combination with disrupting at least one gene selected from the group consisting of the sfb3 gene, the seb1 gene, the gas1 gene, the crz1 gene, and the tps2 gene.

These and other aspects and embodiments of present variant strains and methods will be apparent from the description, including the accompanying Figures.

DETAILED DESCRIPTION

I. Overview

Figure 1:
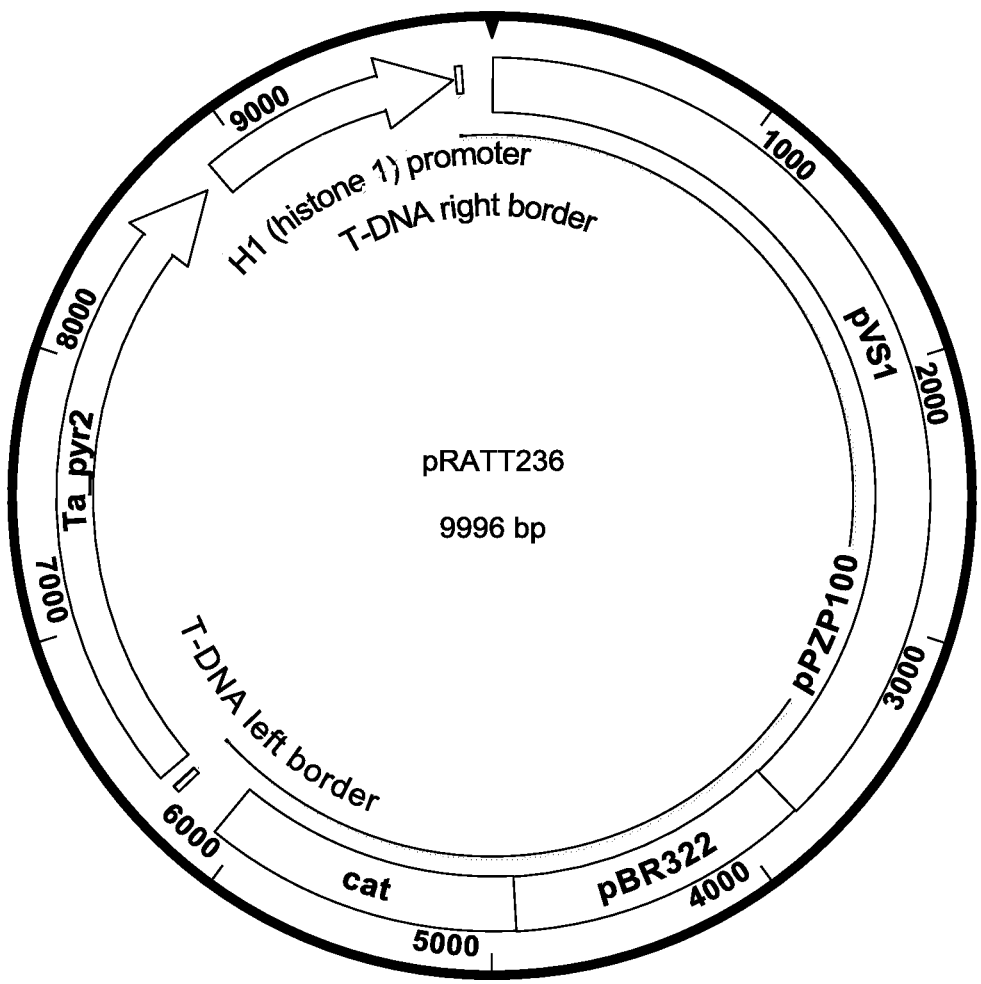
FIG. 1 is a map of the *Agrobacterium tumefaciens* pRATT 236 vector.

The present strains and methods relate to variant strains of filamentous fungus cells having genetic modifications that affect their morphology and growth characteristics. When the variant cells are grown in submerged culture, they produce a cell broth that has different rheological properties compared to a cell broth comprising cells of the parental strain. Some of these variant strains are well-suited for the large-scale production of enzymes and other commercially important proteins.

II. Definitions

Prior to describing the present strains and methods in detail, the following terms are defined for clarity. Terms not defined should be accorded their ordinary meanings as used in the relevant art.

As used herein, "*Trichoderma reesei*" refers to a filamentous fungus of the phylum *Ascomycota*, subphylum *Pezizomycotina*. This organism was previously classified as *Trichoderma longibrachiatum*, and also as *Hypocrea jecorina*.

As used herein, the phrase "variant strain of filamentous fungus cells," or similar phrases, refer to strains of filamentous fungus cells that are derived (i.e., obtained from or obtainable from) from a parental (or reference) strain belonging to the *Pezizomycotina*, e.g., by genetic manipulation. In the present description, parental and variant strains can be described as having certain characteristics, such as genetic modifications, expression phenotypes, morphology, and the like; however, the skilled person will appreciate that it is technically the cells of the parental or variant strain that have such characteristics, and "the strains" are referred to for convenience.

As used herein, the term "protein of interest" refers to a polypeptide that is desired to be expressed in a filamentous fungus. Such a protein can be an enzyme, a substratebinding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme (s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'S, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases can be searched using FASTA (Pearson et al. (1988) *Proc. Natl. Acad. Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, or strains, found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression.

As used herein, the terms "genetic manipulation" and "genetic alteration" are used interchangeably and refer to the alteration/change of a nucleic acid sequence. The alteration can included but is not limited to a substitution, deletion, insertion or chemical modification of at least one nucleic acid in the nucleic acid sequence.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, the term "rheology" refers to a branch of physics dealing with the deformation and flow of matter.

As used herein, "viscosity" is a measure of the resistance of a fluid to deformation by mechanical stress, such as shear stress or tensile stress. In the present context, viscosity can also refer to the resistance of a cell broth comprising filamentous fungus cells to mechanical stress, e.g., as provided by a rotor/impeller. Because the viscosity of a cell broth can be difficult to measure directly, indirect measurements of viscosity can be used, such as the dissolved oxygen content of the culture broth at a preselected amount of agitation, the amount of agitation required to maintain a preselected dissolved oxygen content, the amount of power required to agitate a cell broth to maintain a preselected dissolved oxygen content, or even colony morphology on solid medium.

As used herein, an "altered-viscosity" variant strain of filamentous fungus cells refers to a variant strain that produces a cell broth that has either a reduced or increased viscosity (i.e., reduced or increased resistance to shear or tensile stress) compared to an equivalent cell broth produced by a parental strain. Generally, equivalent cell broths have comparable cell masses. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cell broths are described, herein. Generally, comparable (or equivalent) cell broths have comparable cell masses.

As used herein, a "reduced-viscosity" variant strain of filamentous fungus cells refers to a variant strain that produces a cell broth that has reduced viscosity (i.e., reduced resistance to shear or tensile stress) compared to an equivalent cell broth produced by a parental strain. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more.

As used herein, "dissolved oxygen" (DO) refers to the amount of oxygen ($O_2$) present in a liquid medium as measured in vol/vol units. The dissolved oxygen level can be maintained at a high level, e.g., between 170-100% and 20%, between 100-80% and 20%, between 70% and 20%, between 65% and 20%, between 60% and 20%, between 55% and 20%, between 50% and 20%, between 45% and 20%, between 44% and 20%, between 43% and 20%, between 42% and 20%, between 41% and 20%, between 40% and 20%, between 35% and 20%, between 30% and 20%, and between 25% and 20% throughout the fermentation. In particular, the dissolved oxygen can be high at the beginning of the fermentation and to be permitted to fall as the fermentation progresses. The dissolved oxygen level can be controlled by the rate at which the fermentation is agitated, e.g. stirred, and/or by the rate of addition of air or oxygen. The culture can be agitated, e.g., stirred at between 400-700 rpm and the dissolved oxygen level is maintained above 20%, above 25%, above 30%, above 35%, above 40%, above 45%, above 50% and above 55% or more by altering the air or oxygen flow rate and impeller speed.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, variant cells "maintain or retain a high level of protein expression and/or secretion" compared to a parental strain if the difference in protein expression between the variant strain and a parental strain is less than about 20%, less than about 15%, less than about 10%, less than about 7%, less than about 5%, or even less than about 3%.

As used herein, host cells have been "modified to prevent the production of a specified protein" if they have been genetically or chemically altered to prevent the production of a functional protein/polypeptide that exhibits an activity characteristic of the wild-type protein, particularly an activity that promotes elongation of hyphae or otherwise increases the viscosity of a filamentous fungus in liquid culture. Such modifications include, but are not limited to, deletion or disruption of the gene encoding the protein (as described herein), modification of the gene such that the encoded polypeptide lacks the aforementioned activity, modification of the gene to affect post-translational processing or stability, and combinations, thereof.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

As used herein, a variant strain produces "substantially the same amount" of protein per unit amount of biomass as a parental strain if the amount of protein produced by the variant strain is no more than 20% reduced, no more than 15% reduced, no more than 10% reduced, an even no more than 5% reduced compared to the amount of protein produced by the parental strain, wherein the amount of protein is normalized to the total amount of biomass of cells from which protein production is measured, wherein biomass can be expressed in terms of either wet (e.g., of cell pellet) or dry weight.

As used herein, a variant strain produces "substantially more protein per unit amount of biomass" than a parental strain if the amount of protein produced by the variant strain is at least 5% increased, at least 10% increased, at least 15% increased, or more, compared to the parental strain, wherein the amount of protein is normalized to the total amount of biomass of cells from which protein production is measured, wherein biomass can be expressed in terms of either wet (e.g., of cell pellet) or dry weight.

As used herein, "fluorochromes" are fluorescent dyes. Preferred fluorochromes bind to cellulose and/or chitin in the cell walls of fungi.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

CFU colony forming units
EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
DO dissolved oxygen
g or gm gram
μg microgram
mg milligram
kg kilogram
lb pound
μL and μl microliter
mL and ml milliliter
mm millimeter
μm micrometer
mol mole
mmol millimole
M molar
mM millimolar
μM micromolar
nm nanometer
U unit
ppm parts per million
sec and " second
min and ' minute
hr and h hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute
Δ relating to a deletion
CER $CO_2$ evolution rate
bp base pairs

III. Filamentous Fungal Strain with Altered Mpg1 Protein Production

In one aspect, a variant strain of filamentous fungus derived from a parental strain is provided, the variant strain comprising a genetic alteration that causes cells of the variant strain to produce an altered amount of functional Mpg1 protein compared to cells of the parental strain. The cells of the variant strain subsequently produce, during aerobic fermentation in submerged culture, a cell broth that requires an altered amount of agitation to maintain a preselected dissolved oxygen content, or a cell mass that maintains an altered dissolved oxygen content at a preselected amount of agitation, compared to the cells of the parental strain.

In some cases, the genetic alteration causes cells of the variant strain to produce a reduced amount of functional Mpg1 protein compared to cells of the parental strain, and the resulting cell broth requires reduced agitation to maintain a preselected dissolved oxygen content or maintains a higher dissolved oxygen content at a preselected amount of agitation compared to the cells of the parental strain. In such cases, it is believed that the cell mass of the variant strain exhibits reduced viscosity compared to a cell mass of the parental strain, which accounts for the observations relating to dissolved oxygen content and agitation, as described in the Examples.

The reduction in the amount of functional Mpg1 protein can result from disruption of the mpg1 gene present in the parental strain. Because disruption of the mpg1 gene is a primary genetic determinant for conferring a reduced viscosity phenotype to the variant strain, such variant strains need only comprise a disrupted mpg1 gene, while all other genes can remain intact. In some cases, the variant strains can optionally include additional genetic alterations compared to the parental stain from which they are derived. Such additional genetic alterations are not necessary to confer a reduction in viscosity but can further reduce viscosity or confer other advantages for the variant strain.

Disruption of the mpg1 gene can be performed using any suitable methods that substantially prevent expression of a function mpg1 gene product, i.e., the Mpg1 protein. Exemplary methods of disruption as are known to one of skill in the art include but are not limited to: Complete or partial deletion of the mpg1 gene, including complete or partial deletion of, e.g., the Mpg1-coding sequence, the promoter, the terminator, an enhancer, or another regulatory element; and complete or partial deletion of a portion of the chromosome that includes any portion of the mpg1 gene. Particular methods of disrupting the mpg1 gene include making nucleotide substitutions or insertions in any portion of the mpg1 gene, e.g., the Mpg1-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can be used to disrupt the mpg1 gene.

Mutations in the seb1 gene can reduce the efficiency of the mpg1 promoter, reduce the efficiency of a mpg1 enhancer, interfere with the splicing or editing of the mpg1 mRNA, interfere with the translation of the mpg1 mRNA, introduce a stop codon into the Mpg1-coding sequence to prevent the translation of full-length Mpg1 protein, change the coding sequence of the Mpg1 protein to produce a less active or inactive protein or reduce Mpg1 interaction with other cell wall components, change the coding sequence of the Mpg1 protein to produce a less stable protein or target the protein for destruction, cause the Mpg1 protein to misfold or be incorrectly modified (e.g., by glycosylation), or interfere with cellular trafficking of the Mpg1 protein.

In one embodiment, these and other genetic manipulations act to reduce or prevent the expression of a functional Mpg1 protein, or reduce or prevent the normal biological activity of the Mpg1 protein, thereby producing a morphology change in the cell that results in a reduced viscosity phenotype.

In other cases, the genetic alteration increases or restores the expression of a functional Mpg1 protein, or increases the normal biological activity of the Mpg1 protein, thereby producing a morphology change in the cell that results in an increased or restored viscosity phenotype. Exemplary genetic alterations that increase or restore Mpg1 function are those that introduce addition copies of the mpg1 gene into a cell, increase the efficiency of the mpg1 promoter, enhancer, or other control element, increase the translation of the mRNA encoding the Mpg1 protein, increase the stability of mRNA encoding the Mpg1 protein, introduce changes in the mpg1 gene that increase the activity or stability of the Mpg1 protein, introduce changes in the mpg1 gene that modulate the interaction with other proteins or cell wall components, and the like. Other genetic alterations that increase or restore Mpg1 function are those that reverse the effect of genetic alterations that reduce or prevent the expression of a functional Mpg1 protein Filamentous fungus cells for manipulation and use as described are generally from the phylum *Ascomycota*, subphylum *Pezizomycotina*, particularly fungi that have a vegetative hyphae state and include a homolog of the mpg1 gene. Such organisms include filamentous fungus cells used for the production of commercially important industrial and pharmaceutical proteins, including, but are not limited to *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. Particular organisms include, but are not limited to, *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum*, and *Chrysosporium lucknowense*.

As described by Kruszewska et al. (1998) *Cur. Genet.* 33:445-50 and Zakrzewska et al. (2003) *Applied and Environmental Microbiology* 69:4383-89), Mpg 1(PID 122551) from *Trichoderma reesei* encodes a GTP:alpha-D-mannose-1-phoshate guanyltransferase. Over-expression of the mpg1 gene increases GDP-mannose levels, which can play a major regulatory role in early stages of protein glycosylation. However, Mpg1 has heretofore not been described previously as being associated with altered morphology, particularly not an altered morphology that gives rise to a low viscosity phenotype. The present disclosure provides experimental evidence of the association of Mpg1 with altered morphology.

The amino acid sequence of the *Trichoderma reesei* Mpg 1 ((jgi|Trire2|122551) protein is shown, below, as SEQ ID NO: 1:

MKGLILVGGFGTRLRPLTLTLPKPLVEFCNKPMIVHQIEALVAAGVTD

IVLAVNYRPEIMEKFLAEYEEKYNINIEFSVESEPLDTAGPLKLAERI

LGKDDSPFFVLNSDVICDYPFKELLEFHKAHGDEGTIVVTKVEEPSKY

GVVVHKPNHPSRIDRFVEKPVEFVGNRINAGMYIFNPSVLKRIELRPT

SIEKETFPAMVADNQLHSFDLEGFWMDVGQPKDFLSGTCLYLSSLTKK

GSKELTPPTEPYHGGNVMIHPSAKIGKNCRIGPNVTIGPDVVVGDGVR

LQRCVLLKGSKVKDHAWVKSTIVGWNSTVGRWARLENVTVLGDDVTIG

DEIYVNGGSVLPHKSIKANVDVPAIIM

The amino acid sequence of the *Neurospora crassa* Mpg1 protein is shown, below, as SEQ ID NO: 2:

MKALILVGGFGTRLRPLTLTMPKPLVEFGNKRMILHQIEALAAAGVTD

IVLAVNYRPEIMEKYLAEYEKQFGINITISIESEPLGTAGPLKLAEDV

LRKDDTPFFVLNSDVTCEYPFKELAAFHKAHGDEGTIVVTKVEEPSKY

GVVVHKPNHPSRIDRFVEKPVQFVGNRINAGLYIFNPSVIDRVELRPT

SIEQETFPAMVRDGQLHSFDLEGFWMDIGQPKDFLTGTCLYLSSLTKK

GSKELAPTTLPYIHGGNVLIDPSAKIGKNCRIGPNVTIGPNVVVGDGV

RLQRCVLLEGSKVKDHAWVKSTIVGWNSTVGKWARLENVTVLGDDVTI

GDEIYVNGGSILPHKTIKANVDVPAIIM

The amino acid sequence of the *Aspergillus oryzae* Mannose-1-phosphate guanyltransferase protein is shown, below, as SEQ ID NO: 3:

MKGVGGGTRRTTKVCNKMVHAVAAGVTDVAVNYRMKAYKMKAVGGGT

RRTTKVGNRMHVSAAAGVTDVAVNYRDVMVSAKKYYNNSVSDTAGKA

RGKDDSVNSDVCDYKHKAHGDGTVVTKVYNVKSVSGTAGKAKGKDDS

VNSDVCDYKAHKKHGDGTVVTKVDSKYGVVVHKNHSRDRVKVVGNRN

AGMYNSVKRRTSKTAMVADNHSSKYGVVVHKNHSRDRVKVVGNRNAG

YMNSVNRRTSTACKDGHSDGWMDVGKDSGTCYSSTKKGSKTTYVHGG

NVMHSAKGKNCRGNVTGDGWMDVGKDSGTCYTSAKRNSKANSYVYGG

NVMVDSAKGKNCRGNVVGDVVVGDGVRRCVKGSKVKDHAWVKSTVGW

NSTVGRWARNVTVGDDVTGDYVNGGSVHNVVVGDGVRRCVNSKVKDH

AWVKSTVGWNSSVGRWARNVTVGDDVTADVYVNGGSHKSKANVDVAM

KSKNVDVAM

In some embodiments of the present compositions and methods, the amino acid sequence of the Mpg1 protein that is altered in production levels has a specified degree of overall amino acid sequence identity to the amino acid sequence of SEQ ID NOs: 1, 2, or 3, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, or 3. The nucleotide sequences encoding each amino acid sequence can be identified from a BLAST search for each corresponding protein as is know to one skilled in the art.

In some embodiments of the present compositions and methods, the mpg1 gene that is disrupted encodes a Mpg1 protein that has a specified degree of overall amino acid sequence identity to the amino acid sequence of SEQ ID NOs: 1, 2, or 3, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, or 3.

The amino acid sequence information provided, herein, readily allows the skilled person to identify an Mpg1 protein, and the nucleic acid sequence encoding an Mpg1 protein, in any filamentous fungi, and to make appropriate disruptions in the mpg1 gene to affect the production of the Mpg1 protein. The polynucleotide sequences encoding SEQ ID NOs: 1, 2 and 3 can be found in the GenBank or JGI databases, as are known to one of skill in the art.

In another aspect, a method for altering the morphology of filamentous fungus cells is provided. The variant filamentous fungus cells exhibit altered growth morphology on solid medium and produce cell masses having different viscosities when grown in submerged culture compared to parental cell growth and cell broth viscosities.

In some cases, the method comprises disrupting the mpg1 gene in a parental strain using suitable genetic methods, wherein during aerobic fermentation the disrupted mpg1 variant strain produces during aerobic fermentation in submerged culture a cell broth that requires reduced agitation to maintain a preselected dissolved oxygen content, or maintains an increased dissolved oxygen content at a preselected amount of agitation, compared to the cells of the parental strain. Such methods can be used to disrupt the mpg1 gene in any manner described above and elsewhere as are known t one of skill in the art. Preferably, disruption of the mpg1 gene is performed by genetic manipulation using sequence-specific molecular biology techniques, as opposed to chemical mutagenesis, which is generally not targeted to specific nucleic acid sequences. However, chemical mutagenesis can be used with satisfactory results.

In some embodiments, the parental strain into which the reduced viscosity phenotype is introduced creating a reduced viscosity strain already comprises a gene of interest intended to be expressed at high levels. In this manner, the present methods obviate the need to introduce a gene of interest into a pre-existing reduced viscosity strain for production. Thus, the present methods can be used to produce a reduced viscosity variant strain of filamentous fungus cells from a parental strain already comprising a gene of interest.

IV. Additive Effect Produced by Altering Seb1 Production

In some embodiments of the present compositions and methods, genetic alterations that affect Mpg1 production are combined with genetic alterations that affect Seb1 production. The seb1 gene from *Trichoderma atroviride* is a STRE-element-binding protein, and the seb1 gene is believed to be an orthologue of the yeast msn2/4 gene and the *Aspergillus nidulans* msnA gene. Notably, the seb1 gene cannot complement the msn2/4 gene in yeast, so it is probably not a functional homologue. Seb1 is involved with but not essential in the osmotic stress response but has not been described as being associated with altered morphology, particularly those giving rise to a low viscosity phenotype.

A BLAST search of the publicly available genomic DNA sequence of *Trichoderma reesei* performed using the *T. atroviride* Seb1 amino acid sequence (SEQ ID NO: 4) as a query revealed that the *T. reesei* genome includes a single gene that is closely homologous to seb1. No further homologs or similar sequences were identified, suggesting that seb1 is a unique single copy gene. Homologs of the Seb1 proteins were found in e.g., *T. reesei* (SEQ ID NO: 5), *Aspergillus clavatus* (SEQ ID NO: 6), *Aspergillus fumigatus* Af93 (SEQ ID NO: 7), and *Neosartorya fischeri* NRRL 181 (SEQ ID NO: 8):

The amino acid sequence of the *Trichoderma atroviride* Seb1 protein is shown, below, as SEQ ID NO: 4:

MDGMMSQAMGQQAFYFYNHNHDHKMARQAIFAQQMAAYQMVPTLP

PTPMYSRPNSSCSQPPTLYSNGPSVMTPTSTPPLSRKHMMLDAEFG

-continued

DNPYFPSTPPLSTSGSTVGSPKACDMLQTPMNPMFSGLEGIAMKEA

VDTTESLVVDWASIVSPPLSPVYFQSQVSRVPSPTSSPSDILSTAS

CPSLSPSPTPYARSVTSEHDVDFCDPRNLTVSVGSNPTLAPEFTLT

GLAEDLKGEQLSTAQHTFDFNPALPSGLPTFEDFSDLESEADFSNL

VNLGEVNPIDISRPRACTGSSVVSLGHGSFIGDEELSFEDNDAFGF

NSLPSPTSSIDFSDVHQDKRRKKEKKDIKPIMNTAASGSPSGNEQI

GATPAASAASDSNASSASEDPSSMPAPTNRRGRKQSLTEDPSKTFV

CDLCNRRFRRQEHLKRHYRSLHTQEKPFECNECGKKFSRSDNLAQH

ARTHAGGAIVMNLIEDGSEVPAFDGSMMTGPVGDDYNTYGKVLFQI

ASEIPGSASELSSEEGDQSKKKRKRSD

The predicted amino acid sequence of the *Trichoderma reesei* Seb1 protein is shown, below, as SEQ ID NO: 5:

MDGMMSQPMGQQAFYFYNHEHKMSPRQVIFAQQMAAYQMMPSLPPTPMYSRPNSSCSQPPTLYS

NGPSVMTPTSTPPLSSRKPMLVDTEFGDNPYFPSTPPLSASGSTVGSPKACDMLQTPMNPMFSG

LEGIAIKDSIDATESLVLDWASIASPPLSPVYLQSQTSSGKVPSLTSSPSDMLSTTASCPSLSP

SPTPYARSVTSEHDVDFCDPRNLTVSVGSNPTLAPEFTLLADDIKGEPLPTAAQPSFDFNPALP

SGLPTFEDFSDLESEADFSSLVNLGEINPVDISRPRACTGSSVVSLGHGSFIGDEDLSFDDEAF

HFPSLPSPTSSVDFCDVHQDKRQKKDRKEAKPVMNSAAGGSQSGNEQAGATEAASAASDSNASS

ASDEPSSSMPAPTNRRGRKQSLTEDPSKTFVCDLCNRRFRRQEHLKRHYRSLHTQEKPFECNEC

GKKFSRSDNLAQHARTHSGGAIVMNLIEESSEVPAYDGSMMAGPVGDDYSTYGKVLFQIASEIP

GSASELSSEEGEQGKKKRKRSD

The amino acid sequence of the *Aspergillus clavatus* Seb1 protein is shown, below, as SEQ ID NO: 6:

MDTTYTMVGTPVQGQPSFAYYTTNDSQSRQQHFTSHPSEMQAFYGQMQPYPQQQQQTCMPDQQS

IYAAQPMLNMHQMATANAFRGALSMTPIVSPQPTHLKPTIIVQQDSPMLMPLDTRFVSSDYYAF

PSTPPLSTSGSTISSPPSSGRSLHTPINDCFFSFEKVEGVKEGCESDVHSELLANADWSRSDSP

PLTPVFIHPPSLTASQSSDLLSAHSSCPSLSPSPSVSSTFTAPPHSGLSVEPSGTDFCDPRQL

TVESSVDSSTELPPLPTLSCNEEEPKVVLGSATVTLPVHESLSPAYTSSTEDPLGSLPTFDSFT

DLDSEDEFVNNLVDFHPGGNPYFLGDKRQRLGSYLLEEDEFLSDRSFDDLDDHEAFAHSGLPSL

EPSELISVQGDVAEVSEEMRSKKRTTSRRILKRTNSSDSSSESLATSGKRTQASANGRSGHSEA

TSSSAQQSTTPSRQNSTANASSSSEAPSAPVSVNRRGRKQSLTDDPSKTFVCTLCSRRFRRQEH

LKRHYRSLHTQDKPFECHECGKKFSRSDNLAQHARTHGGGSIVMGVIDTNASLQASYEEREPRL

LGAALYEAANAAANKSTTSDSSDGTISDTSSVEGRPIKKRRREDHA

The amino acid sequence of the *Aspergillus fumigatus* Af93 Seb1 protein is shown, below, as SEQ ID NO: 7:

MDATYTMAQTPVQGQPSFAYYPTESQSRQQHFTSHPFEMQYYGQVSSYPQQQAQQQHSMPEQQP

VYAAQPMLNMHQMATTNAFRGALSMTPIASPQPTHLKPTIIVQQDSPALMPLDTRFVSNDFYGF

PSTPPLSTSGSTISSPPSSNGSLHTPINDCFFSFEKVEGVKEGCESDVHCELLANTDWSRSDSP

PLTPVFIQPQSLTASQSSDLLSAQIPCPSLSPSPSPDSATFISHPQSILSAEPSGSDFCDPRQL

-continued

```
TVESSVGAPAELPPLPTLSCNEEEPKVVLGSATVTLPVHEGLSPSFSSSSEDPLGSLPTFDSFS

DLDSEDEFANKLVDFHPIGNTYFQGDKRQRLGTYLLDEDEFLSERSLEDLDDQEAFAQSGLPSV

ESTDFLAVEGDATQSTEEMSSKKRVISRRSLKKASTSESSSDSLAKKTQASATSRSGHSDTTST

VQQSTASSRQNSTANTSNSESPAAPVSVNRRGRKQSLTDDPSKTFVCSLCSRRFRRQEHLKRHY

RSLHTQDKPFECHECGKKFSRSDNLAQHARTHGGGSIVMGVIDTNSSNTQPAFDEPEPRALGLA

LYEAANAATSKSTTSESSDGTISDISSVGGRPAKKRRRDDHV
```

The amino acid sequence of the *Neosartorya fischeri* NRRL 181 Seb1 protein is shown, below, as SEQ ID NO: 8:

```
MDATYTMAQTPVQGQPSFAYYPTESQSRQQHFTSHPSEMQYYGQVPPYPQQQHSMPEQQPVYAA

QPMLNMHQMATTNAFRGALSMTPIASPQPTHLKPTIIVQQQDSPVLMPLDTRFVSNDFYGFPST

PPLSTSGSTISSPPSSNGSLHTPINDCFFSFEKVEGVKEGCESDVHCELLANTGWSRSDSPPLT

PVFIQPPSLTASQSSDLLSAHMSCPSLSPSPSPDSTTFISHPQSVLSAEPSGSDFCDPRQLTVE

SSVGAPAELPPLPTLSCNEEEPKVVLGSATVTLPVHEGLSPSFSSSSEDPLGSLPTFDSFSDLD

SEDEFANKLVDFHPIGNTYFLGDKRQRLGTYLLDEDEFLSERSLEDLDDQEAFAQSGLPSVESS

DFLAAEGDATQNTEEMSSKKRVTSRRSLKRASTSESSSDSLAKKTQASATSRSGHSETTSTVQQ

STASSRQNSTANTSSSGSPAAPVSVNRRGRKQSLTDDPSKTFVCSLCSRRFRRQEHLKRHYRSL

HTQDKPFECHECGKKFSRSDNLAQHARTHGGGSIVMGVIDTNGSNTQPAFDEPEPRALGLALYE

AANAATSKSTTSESSDGTISDTSSVGGRPAKKRRRDDHV
```

In some embodiments of the present compositions and methods, the amino acid sequence of the Seb1 protein that is altered in production levels has a specified degree of overall amino acid sequence identity to the amino acid sequence of SEQ ID NOs: 4, 5, 6, 7, or 8, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 4, 5, 6, 7, or 8. The polynucleotide sequences encoding SEQ ID NOs: 4, 5, 6, 7, or 8 can be found in the GenBank or JGI databases, as are known to one of skill in the art.

In some embodiments of the present compositions and methods, a seb1 gene is disrupted, wherein the seb1 gene encodes a Seb1 protein that has a specified degree of overall amino acid sequence identity to the amino acid sequence of SEQ ID NOs: 4, 5, 6, 7, or 8, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 4, 5, 6, 7, or 8.

The skilled person will appreciate that genetic alterations that affect Seb1 production can be made in the same manner as genetic alterations that affect Mpg1 production, which are detailed, herein. Alterations in the Seb1 protein resulting in alterations in viscosity are further described in Provisional Application No. 61/478,160, filed Apr. 22, 2011, incorporated herein by reference.

V. Additive Effect Produced by Altering Sfb3 Production

In some embodiments of the present compositions and methods, genetic alterations that affect Mpg1 production, or Mpg1 and Seb1 production, are combined with genetic alterations that affect Sfb3 production. The Sfb3 gene (also known as Lst1) has previously been characterized in budding yeast (i.e., *Saccharomyces cerevisiae*), where it encodes a protein associated with the COPII protein coat surrounding transport vesicles that carry proteins from the endoplasmic reticulum to the Golgi apparatus. Sfb3, as well as Sfb2, are homologs of Sec24, all of which genes are involved with packaging specific cargo proteins into the vesicles.

While Sec24 is an essential gene in yeast, Sfb3 and Sfb2 are not, although the deletion of Sfb3 in yeast is known to affect the transport of a plasma membrane transport protein (Pma1p) and a glucanosyltransferase (Gas1p) that is involved in cell wall synthesis.

Using BLAST to search the publicly available genome sequence of *Trichoderma reesei* using *S. cerevisiae* Sec24p, Sfb3p or Sfb2p amino acid sequences as query sequences reveals that *T. reesei* has a single gene that is most closely homologous to yeast Sec24 and a single gene that is most closely homologous to yeast Sfb3. No other homolog was identified suggesting that *T. reesei* does not have a gene equivalent to Sfb2. Moreover, homologs of the Sfb3 proteins were found in e.g., *T. reesei* (SEQ ID NO: 9), *A. oryzae* (SEQ ID NO: 10), *A. niger* (SEQ ID NO: 11), *P. funiculosum* (SEQ ID NO: 12), *P. chrysogenum* (SEQ ID NO: 13), *N. Crassa* (SEQ ID NO: 14), and *F. oxysporum* (SEQ ID NO: 15):

*Trichoderma reesei* Sfb3 amino acid sequence (SEQ ID NO: 9):

MDYTQYHALGHGEVLDPNDPNKTSAPAAPQFQPPSSPYVPPGSPYGAPPYHGGHQAPPMAMPPP

STPGYGPPQGQSFPGSPMPSQDAGLAAQFGGMSLGADAGGAAARKKKKDRHAYHSVEPTGSSQA

FNGLPPGTPAEQFLNVNNPQGIPALGGQFGSPLASPMGTPHMANPGQFPAPTSPFTPSAPVSPA

EFASRFGSPDAATSIGSAGPSQVSPDDMPSIPASRDAIQEHFFKNVYPTFERHVPPPATVSFVA

FDQGNASPKFTRLTLNNIPTTAEGLHATGLPLGMLIQPLAPLQAGEAEIPVLDFGDAGPPRCRR

CRAYINPFMMFRSGGNKFVCNLCSYPNETPPEYFCAVSPQGVRLDRDQRPELHRGTVEFVVPKE

YWTREPVGLRWLFVIDVTQESYNKGFMETFCEGILAALYGGNDEENDEDGEPKRRIPKGAKVGF

ITYDKDIHFYNINPHLDQAHMMIMPDLEDPFLPLGEGLFVDPYESKAIITSLLTRLPEMFSTIK

NPEPALLATLNAAVAALEATGGKVVCSCSTLPTWGPGRLFMRDDGNHPGGELDKKLYTTEHPAW

KKVSEKMASSGIGVDFFLAAPSGGYLDIATIGHVAATTGGETFYYPNFIAPRDGARLSMEITHA

ITRETGFQALMKVRCSTGLQVAAYHGNFVQHTFGADLEIGVIDADKALGVSFSHDGKLDPKLDA

HFQTALLYTTASGQRRVRCSNVIASVSDTSKESNTKELAIRQCLKFVDQDAVVGIFAKEASTKL

ATTSANLQDVRNWLTERTIDIMAYYKKHSANQFPPSQLVMPERLKEFCMYMLGMLKCRAFKGGI

ENSDRRVHELRMVRSMGPLELSLYLYPRMIALHNLQPEEGFADPETGHLKMPPSVRTSFSRVEP

GGVYLVDNGQQCLLWFHAQTSPNLITDLFGEGHDSLKGLDPYTSTLPVLETHLSAQVRNIIEFL

KSMRGSKGMTIQLARQGIDGAEYEFARMLVEDRNNEAKSYVDWLVHIHRGVQLELSGQRKKEGD

GEATAVMANFAGLRPAYW

*Aspergillus oryzae* RIB40 Sfb3 amino acid sequence (GI: 83766074; SEQ ID NO: 10):

MADQSMYNTLGQGTSPAEDPSNPNRMAHQVPPQSQPAAGFPPGPYPPQPGAYYGNPPPNQYDAPAA

APPTQQLQSPPPRGLAPSPQLAYGTETQTHMGAPADPMAGLASQMSGLGIMGDSGARPGKKKHRHA

HHEIGGATASAPQQFAGMPQAGMQPSSQFLNTGLNQAPRPISPAAGVPPAGIVPQPGVPAPGSGSV

PTQGKIDPEQIPSIPQSRDIPTMYYFDHIYPTMERHLPPPAAVPFVAHDQGNSSPKHARLTLNNIP

TTSDFLSSTALPLGMVLQPLARLDPGEPEVPVLDFGEMGPPRCRRCRAYINPFMTFRSGGNKFVCN

MCTFPNDVAPEYFAPLDMSGARVDRLQRPELMIGTVEFMVPKEYWNKEPVGLQRLFLIDVSQESVN

RGFLKGVCKGITEALYGAPDASEEDAAARRVPEGSKIGIVTYDREVHFYNLSAQLDQAQMMVMTDL

EEPFVPLSEGLFVDPYESKDIITSLLHRIPKIFSHIKKPEPALLPALNAAMSALQATGGKIFASIC

SLPTWGPGALHMRDDPKVHGTDAERKLFTTDNQAWRTTAGKMAEHGTGVDMFVAAPGGTYVDVATI

GHVAEVSGGETFFYPNFHAPRDILKLSQEFAHAVTRETGYQAMMKVRCSNGLQVSAYHGNFIQHAL

GADLEIGSIDADKAIGVMFSYDGKLDPKLDAHFQAALLYTTAEGQRRVRCINVVAAVNEGGLETMK

FIDQDCVVSIMAKEAAAKTVDKSLKDIRASITEKTVDIFSGYRKVFSGSHPPGQLVLPENLKEFSM

YMLALIKSRAFKGGQEASDRRIHDMRMLRSIGATELALYLYPRVIPIHNMQPEDGFPNEQGQLQVP

PSLRASFSKIEEGGAYLVDNGQICLLWLHSRVSPNLLEDLLGPGQSSLQGLNPQTSSLPVLETHLN

AQVRNLLQYFSTMRGSKSVAIQLARQGLDGAEYEFARLLVEDRNNEAQSYVDWLVHIHRQINLELA

GHRKREDTSAEGSLTSLAGLRAPYW

*Aspergillus niger* Sfb3 amino acid sequence (SEQ ID NO: 11)

```
MADPNMYHTYGQAPVPGENPSDPNQMAYQVPPQGYPAAGIPPGPSPPQPGAAYGVPAPNQQWPA
YGSPPPAQQPLQQPPSQFAHQADPQAAMGAPVDPGMAGLASQMSGLGIMGGEGGAARSSKKKHR
HAHHEIAGASASVAQPFAAAPQDPMQPTSQFLNTGLNQAPRPISPAASIPAPVNPAFGGGAGAV
PTQGKVDPEQIPSIPRSRDLPAQYYFNHVYPTMERHLPPPAAVPFVAHDQGNSSPKYARLTLNN
IPSTSDFLSSTGLPLGMVLQPLARLDGEQPIPVLDFGDAGPPRCRRCRAYINPFMSFRSGGNKF
VCNMCTFPNDVPPEYFAPLDPSGSRIDRMQRPELMMGTVEFLVPKDYWNKEPVGLQWLLLIDVS
QESVNKGFLKGVCKGIMEALYSEETENPEDEAPARRIPEGAKIGIVTYDKEVHFYNLSAQLDQA
QMMVMTDLEEPFVPLSEGLFVDPYESKDVITSLLQRIPSIFSHVKNPQPALLPALNAALSALRP
TGGKIVGTIASLPTWGPGALSLRDDPKVHGTDAERKLFTTEHAGWRETAGHLAEAGIGLDMFIA
APSGTYMDVATIGHIPEVTGGETFFYPNFHAPRDIRKLSKELAHAITRETGYQALMKVRCSNGL
QVSGYHGNFVQHTFGADLEIGAIDADKAIGVVFSYDGKLDPKLDAHFQAALLYTSANGQRRVRC
INTVAAVNEGGMETMKFVDQDAVVAMVAKDAASKTLDKSLKDIRAGVSEKTVDIFSGYRKIFSG
SHPPGQLVLPENLKEFSMYMLSLIKSRAIKGGQEASDRRIHDMRMLRSIGCTELSLYLYPRIIP
IHNMQPTDGFPNEQGQLQVPPSLRASFSKIEEGGAYLVDNGQQCLLWLHSHVSPNLLEDLFGEG
QTSLQGLSPQISTIPVLETHLNAQVRNLLQYFSTIRGSKAVTIQLARQGLDGAEYEFARMLVED
RNNEAQSSVDWLVHIHRQINLELAGHRKREDTAGEGGLTSLAGLRAPYW
```

*Penicillium funiculosum* Sfb3 amino acid sequence (SEQ ID NO: 12)

```
MADYSTYHSSGYAGAPGEDPNRQQPAVPAPYHSPNAPPGQAIQQPGITPYGAAQPPQFPGQPGV
GYGVAPVPSPPQALGGPDVGDLATRIGGLGIISDAGTRSHKKKHRHAYHDIGGPNAQGLNTFPS
QTNLQSQFLNTGLNQPEQQPAAPAAFPGAPVGQVPANVAPGAAPEVGGVGSVPTQGKIDPEQIP
SVPRSRDLPAQYYFNNVYPTMERHVPPPASIPFIAHDQGNSSPKVARLTLNNIPSSSDFLQSTG
LPLGMILQPLAKLDAGEQPVPVIDFGDIGPPRCRRCRTYINPFMTFRSGGNKFVCNMCTFPNDV
PPEYFAPVDPSGVRVDRLQRPELMLGTVEFTVPKEYWVKEPAGLHQLFLIDVSQESVNRGFLKG
VCDGIINALYGEEEPVEGAEPETRKVPEGSKIGIVTFDREIHFYNLLPRLDKAQMMVMTDLEEP
FVPLSEGLFVDPYESKDVITSLLEQLPSLFARVKSPESTLLPTIKAAISALQATGGKIICCLTS
LPTYGPGKLVMKDKSQAPDGENKLFAIDNPDYKAAATKLTEAGVGIDFFVAAPGGSFMDLTTIG
YTAAISGGECFFYPNFHSPRDSLKLAQEISHTVTRETGYQALMKVRCSNGLQVSAYYGNFLQHT
FGADLEIGTIDADKALGVLFSYDGKLDPKLDAHFQAALLYTAANGQRRVRCINIVAGVNEGGIE
TMKCIDQDAVVAIIAKEAASKAGDKTLKDIRASITEKTVDIFSGYRKNFSGSHPPGQLVLPENL
KEFSMYMLGLLKSRAFKGGSETADRRVHDLRMLRSIGCLELSLYLYPRIIPIHNMSAEDGFANE
QGQLQVPPALRASFSRVEEGGAYLIDNGQGILLWIHSFVSPNLLEDLFGPGITSLQALDPNTSS
LPVLETHLNAQVRNLLQYLSTVRGSKAVTIQLARQGIDGAEYEFARSLVEDRNNEAQSYVDWLV
HIHRQINLELAGHRKKEDSATSSGEGALSSLAGIRAPYW
```

*Penicillium chrysogenum* Sfb3 amino acid sequence (SEQ ID NO: 13)

```
MADSSMYNTMGQGSSEDPSNPQYMAQVPPQQYPAGYPPTAAPLQPGAPYANPAPNQWPAYGSPQ
QPGMASPGIAYNAPQQPMGAAVDPGMAGLASQMGGLDIAADAGARTHRKKHRHAHHDIGGGAAP
```

-continued

```
PAQGFNIGMDQGGLQQPQPQQQSQFLNTGLNQHADRPVSPAVGLVSGQSVAAIPGIQSGAGSVP

TSGRIDPEHIPSIPRSRDLPAQYYFNHVYPTMDQHLPPPAAIPFVAQDQGNSSPKYARLTLNNI

PSASDFLTSTGLPLGMILQPLAPLDPGEQPIPVLDFGDVGPPRCRRCRTYINPFMSFRSGGSKF

VCNMCTFPNDTPPEYFAPLDPSGARVDRMQRPELLMGTVEFTVPKEYWNKEPVGLQTLFLIDVS

RESVHRGFLKGVCAGIKDALYGDDDKASEGTEGDGSSRKLPVGAKVGIVTYDKEVHFYNLAAAL

DQAQMMVMTDLDEPFVPLSEGLFVDPYESKSVITSLLSRIPKIFSSIKNPESALLPTLNSALSA

LQATGGKIVCAVASLPTCGPGHLAIREDPKVHGTDAERKLFTTENPAWKKTASKLAEAGVGLDL

FMAAPGGTYLDVATIGHVSSLTGGETFFYPNFHAPRDLLKLRKEIAHAVTRETGYQTLMKVRCS

NGLQVSAYHGNFVQHTLGADLEIAGVDADKAVGVLFSYDGKLDPKLDAHFQAALLYTSADGQRR

VRCINVVAAVNEGGLETMKFVDQDAVVSVIAKEAASKTLDKNLKDIRASISEKTVDIFSGYRKI

FSGSHPPGQLVLPENLKEFSMYMLSLVKSRAFKAGPESSDRRIHDMRLIRSMGCTEMALYLYPR

IIPVHNMQPEDGFANEHGQLQIPPTMRASYSRIEDGGVYIVDNGQAILLWIHAQVSPNLLEDLF

GPGHNSLQGLNPNTSSLPVLETHLNAQVRNLLQYLSTVRGSKSVTIQLARQGLDGAEYEFARLL

LEDRNNEAQSYVDWLVHIHRQINLELAGHRKKEEGGEGALASLSAMRTPYW
```

Neurospora crassa Sfb3 amino acid sequence (SEQ ID NO: 14)

```
MADYTMYEALGQGETLDPNDPNRITQPAPPQFQPPVAPNPYHPGAEYNAPGQQQQQQQQYGQQY

GQQYGQQYGQQQYGQEYGHQQQQQQQQQYGAPSPYGAPPAHSPVSPMDDVGLAAQMGGMSLGAG

AGAADHHGRKKKKDRHAFHTVEAPAGSSQPFNGMPPAGIPATQFLNADPSLAGRIPGPGHGQFP

MPASPAFGPVPTSAADFAARDATQGVGSGVFAAGGPQGGKPSPDDTPSVPLSRDAVQPYFHTNV

YPTFERLVPPPAVTSFVALDQGNSSPKFARLTMTNLPASAEGLKSTGLPLGLLLQPLAETQPGE

LPIPVLDFGEQGPPRCHRCRAYMNPFMMFKAGGNKFVCNLCIYANDTPPEYFCALSPQGVRVDR

DQRPELTRGTVEFVVPKEYWTKEPVGMRYLFVIDVTQESYNKGFLESFCEGILSALYGGSEEGE

DQDETGEPKRKIPAGAKVGFVTFDQEIHFYNVSPALEQAQMIVMPDIEDPFLPLSDGLFVDPYE

SKAVISSLLTRLPQMFSNIKNPEPALLSALNSAVAALEKTGGKVFCSLAALPTWGPGRLFMRDD

GKHPGGEPDKKLFTTEHPGWRKLAEKMVSLGVGADFFMASPSGGYLDIATIGHVSSTTGGETFF

YPNFVVQRDSTKLSLEIHHAVRRETGYAALMKVRCSNGLQVNAYHGNFIQHTFGADLEIGVIDA

DKALAVTFGYDGKLDSKLDAHFQAALLYTTASGQRRVRCINVIAGVSDLARDCMKYIDQDAIVS

ILAKEASTKLSTTSANLKEVRSSLTEKTIDILALYRKNHLAVPHPPQQLVMPERLKEFTMYVLG

MLKCRAFKGGNETTDRRVHDMRLIRSMGARELSLYLYPRIIPLHSLQPEDGYPDATTGHLRMPS

TMRASFARVEPGGVYLVDNGQVCLLWMHAQTAPALIQDLFGEDKTTLQSLDPYTSTIPVLETHL

NAQTRNIIEYMRTVRGSKGLTIQLARQGIDGAEFEFARMLVEDRNNEAQSYVDWLVHVHKGVQL

ELAGQRKREDGESHSALGSFTGLRPAYW
```

Fusarium oxysporum Sfb3 amino acid sequence (SEQ ID NO: 15)

```
MADYAQYHALGQGEVIDPNDPNRTSQPSAQQFQPPIAPSPYQQQASPYGAPQYLGGQQAPPPMT

GSPAPAPGYGYAPPQAQAPPGQAPPSQDATLAAQLGGMNLGDGHGTARRKKKDRHAYHTVEPTG

SSQAFNGMPPQGTSATQFLDSVPGGPGFGGQFGSPQGTPQMQSQSQFSAPVNPAFGPGPVAGTP

GVGEGLGTASVSTSGPKGVSPDDMPSVPASRDAIQQYYLKNVYPTFERHVPPPSTVSFVAYDQG
```

-continued

```
NSSPKYTRLTLNNIPTTQDALQATGLSLGLLLQPLAPLQAGEAEIPVLDFGEAGPPRCRRCRAY

MNPFMMFRSGGNKFVCNLCAYPNDTPPEYFSATNPQGVRVDRDTRPELHRGTVEFVVPKEYWTR

EPVGLRWLFLIDVTQESYNKGYVEAFCEGIRVALYGGEDQELDENGEPKRRIPEGAKVGFVTYD

KDIHFYNVNPALDQAQMMIMPDLEDPFVPLSEGLFVDPYESKDVITSLLTRLPDMFSTIKNPEP

ALLAALNSALAALEATGGKVVASCSALPTWGPGRLFMRDNGNHPGGEIDKKLYTTEHPAWKKVA

EKMAASGVGADFFLAAPSGGYLDIATIGHVSSTTGGETFYYPNFIAARDSRKLSLEISHAVTRE

TGFQALMKVRCSNGLQVSGYHGNFIQHTFGADLEIGVIDADKAMGVSFSYDGKLDPKLDAHFQS

ALLYTTASGERRVRCSNVIASVTETSKESGAREQGIRECLKFVDQDAVIGMLAKEASTKLATTS

SNLKDIRHWLSEKAIDVLACYRKHAAQQHPPGQLVMPERLKEYCMYLLGLLKCRALKGGVENSD

RRVHEMRMLRSMGALELSLYLYPRMIPIHNLAPEEGFADPETGHLKMPPAIRTSFSRVEPGGVY

LVDNGQQCLLWFHSQTSPNLISDLFGEDKDSLKSLDPYTSALPLLETHLNAQVRNIIEFLRTMR

GSKGLTIQLARQGIDGAEFDFARMLVEDRNNEAQSYVDWLVHIHKGVQLELSGQRKKEGEEHTA

ASLSNFAGLRPAYW
```

In some embodiments of the present compositions and methods, the amino acid sequence of the Sfb3 protein that is altered in production levels has a specified degree of overall amino acid sequence identity to the amino acid sequence of SEQ ID NOs: 9. 10, 11, 12, 13, 14, or 15, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 9. 10, 11, 12, 13, 14, or 15. The nucleotide sequences encoding each amino acid sequence can be identified from a BLAST search for each corresponding protein as is know to one skilled in the art.

In some embodiments of the present compositions and methods, a sfb3 gene is disrupted, wherein the sfb3 gene encodes a Sfb3 protein that has a specified degree of overall amino acid sequence identity to the amino acid sequence of SEQ ID NOs: 9. 10, 11, 12, 13, 14, or 15, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 9. 10, 11, 12, 13, 14, or 15.

An alignment of the amino acid sequences of the Sfb3 proteins from approximately 40 *Pezizomycotina* species revealed a specific amino acid sequence, i.e., IQLARQGXDGXEXXXARXLXEDRNXEAXSXVDWL (SEQ ID NO: 16, where X is any amino acid residue), which is close to the C-terminus of the Sfb3 proteins, and not found in Sec24 proteins. This consensus sequence can be used to identify Sfb3 proteins and variants thereof in other members of the *Pezizomycotina*.

The skilled person will appreciate that genetic alterations that affect Sfb3 production can be made in the same manner as genetic alterations that affect Mpg1 and/or Seb1 production, which are detailed, herein. Alterations in the Sfb3 protein resulting in alterations in viscosity are further described in PCT Publication No. WO 2012/027580 A1, published 1, Mar. 2012, filed as International Application No. PCT/US2011/049164, filed 25, Aug. 2011, incorporated herein by reference.

VI. Utility

The use of reduced viscosity strains of filamentous fungi is known to improve the distribution of oxygen and nutrients in a submerged culture, reduce the amount of energy required to agitate a submerged culture, and increase the cell mass present in the culture, leading to increased protein production. Moreover, the present variant strains of filamentous fungus offer significant advantages over previously-described reduced viscosity strains.

First, the present variant strains can have a fully defined genome, making them well-suited for subsequent genetic manipulation, complementation, mating, and the like. Second, the present strains are not adversely affected in protein production, for example, by the manipulation(s) that resulted in the attendant viscosity alteration. Third, reduced viscosity strains can be produced from essentially any parental strain, including parental strains that already produce a protein intended for high level expression (i.e., a protein of interest), already encode a selectable marker, or already include other features that are desirable in a production host. Thus, the present strain and methods eliminate the need to transfer a gene encoding a protein of interest into a preexisting reduced viscosity production strain.

The present strains and methods find use in the production of commercially important protein in submerged cultures of filamentous fungi. Commercially important proteins include, for example, cellulases, xylanases, pectinases, lyases, proteases, kinases, amylases, pullulanases, lipases, esterases, perhydrolases, transferases, laccases, catalases, oxidases, reductases, chlorophyllases, hydrophobin, chymosin, carbonic anhydrase, hymidylate synthase, dihydrofolate reductase, tyrosine kinases, multi-drug resistance proteins (e.g., ABC P-gp proteins), CAD (carbamyl-P synthase, aspartate transcarbamylase, dihydroorotase), topoisomerases, ribonucleotide reductase, and antibodies and other enzymes and non-enzyme proteins capable of being expressed in filamentous fungi. Such proteins can be suitable for industrial, pharmaceutical, animal health and food and beverage use.

The following numbered paragraphs further describe various aspects and embodiments of the present compositions and methods. The subject matter of each of the numbered paragraphs can be used alone or in combination with the subject matter of any other numbered paragraph, as indicated.

1. In one aspect, a variant strain of filamentous fungus derived from a parental strain is provided, the variant strain comprising a genetic alteration that causes cells of the variant strain to produce an altered amount of functional Mpg1 protein compared to cells of the parental strain, wherein the cells of the variant strain produce during aerobic fermentation in submerged culture a cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.
2. In some embodiments of the variant strain of paragraph 1, the altered amount of functional Mpg1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.
3. In some embodiments of the variant strain of paragraphs 1 or 2, the genetic alteration comprises a disruption of the mpg1 gene present in the parental strain.
4. In some embodiments of the variant strain of paragraph 3, disruption of the mpg1 gene is the result of deletion of all or part of the mpg1 gene.
5. In some embodiments of the variant strain of paragraph 3, disruption of the mpg1 gene is the result of deletion of a portion of genomic DNA comprising the mpg1 gene.
6. In some embodiments of the variant strain of paragraph 3, disruption of the mpg1 gene is the result of mutagenesis of the mpg1 gene.
7. In some embodiments of the variant strain of any of paragraphs 3-6, disruption of the mpg1 gene is performed using site-specific recombination.
8. In some embodiments of the variant strain of any of paragraphs 3-7, disruption of the mpg1 gene is performed in combination with introducing a selectable marker at the genetic locus of the mpg1 gene.
9. In some embodiments of the variant strain of any of paragraphs 1-8, the variant strain does not produce functional Mpg1 protein.
10. In some embodiments of the variant strain of any of paragraphs 1-8, the variant strain does not produce Mpg1 protein.
11. In some embodiments of the variant strain of any of paragraphs 1-10, the variant strain further comprises a gene encoding a protein of interest.
12. In some embodiments of the variant strain of any of paragraphs 1-11, further comprises a disruption of the sfb3 gene.
13. In some embodiments of the variant strain of any of paragraphs 1-12, further comprises a disruption of at least one gene selected from the group consisting of the sfb3 gene, the seb1 gene, the gas1 gene, the crz1 gene, and the tps2.
14. In some embodiments of the variant strain of any of paragraphs 1-13, the variant strain produces substantially the same amount of, or more, protein per unit amount of biomass as the parental strain.
15. In some embodiments of the variant strain of any of paragraphs 1-14, the filamentous fungus is a *Pezizomycotina* species.
16. In some embodiments of the variant strain of any of paragraphs 1-15, the filamentous fungus is a *Trichoderma* spp.
17. In some embodiments of the variant strain of any of paragraphs 1-16, the filamentous fungus is *Trichoderma reesei*.
18. In another aspect, a method for producing a variant strain of filamentous fungus cells is provided, comprising: introducing a genetic alteration into a parental strain of filamentous fungal cell, which genetic alteration alters the production of functional Mpg1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.
19. In some embodiments of the method of paragraph 18, the genetic alteration reduces or prevents the production of functional Mpg1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.
20. In some embodiments of the method of paragraph 18 or 19, the genetic alteration comprises disrupting the mpg1 gene in a parental filamentous fungal cell using genetic manipulation.
21. In some embodiments of the method of any of paragraphs 18-20, the genetic alteration comprises deleting the mpg1 gene in a parental filamentous fungal cell using genetic manipulation.
22. In some embodiments of the method of any of paragraphs 18-21, the genetic alteration is performed using site-specific genetic recombination.
23. In some embodiments of the method of any of paragraphs 18-22, disruption of the mpg1 gene is performed in combination with introducing a selectable marker at the genetic locus of the mpg1 gene.
24. In some embodiments of the method of any of paragraphs 18-23, disruption of the mpg1 gene is performed in combination with disrupting the sfb3 gene.
25. In some embodiments of the method of any of paragraphs 18-24, disruption of the mpg1 gene is performed in combination with disruption of at least one gene selected from the group consisting of the sfb3 gene, the seb1 gene, the gas1 gene, the crz1 gene, and the tps2 gene.
26. In some embodiments of the method of any of paragraphs 18-25, the variant strain produces substantially the same amount of, or more, protein per unit amount of biomass as the parental strain.
27. In some embodiments of the method of any of paragraphs 18-26, the filamentous fungus is a *Pezizomycotina* species.
28. In some embodiments of the method of any of paragraphs 18-27, the filamentous fungus is a *Trichoderma* spp.

29. In some embodiments of the method of any of paragraphs 18-28, the filamentous fungus is *Trichoderma reesei*.
30. In some embodiments of the method of any of paragraphs 18-29, the parental strain further comprises a gene encoding a protein of interest.
31. In some embodiments of the method of paragraph 30, the gene encoding the protein of interest is present in the parental strain prior to introducing the genetic alteration that reduces or prevents the production of functional Mpg1 protein.
32. In another aspect, a protein of interest produced by the variant strain of paragraph 11 is provided.
33. In another aspect, a variant strain of filamentous fungus produced by the method of any of paragraphs 18-31 is provided.
34. In another aspect, a variant strain of filamentous fungus derived from a parental strain is provided, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
(b) a gene encoding a protein of interest,
wherein the gene encoding the protein of interest is present in the variant strain prior to the genetic alteration in (a).
35. In some embodiments of the variant strain of paragraph 34, the genetic alteration comprises a disruption of the mpg1 gene present in the parental strain.
36. In some embodiments of the variant strain of paragraph 35, disruption of the mpg1 gene is performed in combination with introducing a selectable marker at the genetic locus of the mpg1 gene.
37. In some embodiments of the variant strain of paragraph 35 or 36, disruption of the mpg1 gene is performed in combination with disrupting at least one gene selected from the group consisting of the sfb3 gene, the seb1 gene, the gas1 gene, the crz1 gene, and the tps2 gene.
38. In some embodiments of the variant strain of any of paragraphs 35-37, disruption of the mpg1 gene is performed in combination with disrupting the seb1 gene.

These and other aspects and embodiments of the present strains and methods will be apparent to the skilled person in view of the present description. The following examples are intended to further illustrate, but not limit, the strains and methods.

EXAMPLES

Example 1

Identification of the Mpg1 Gene as Responsible for Morphological Changes in Filamentous Fungus A. Overview Filamentous fungi disruption libraries were prepared by transforming an exemplary filamentous fungus, i.e., *Trichoderma reesei*, with a nucleic acid containing the pyr2 gene and the *T. reesei* histone H1 promoter, using *Agrobacterium tumefaciens*-mediated transformation. In this manner, the pyr2 gene served as both a selectable marker and a gene tag. The histone H1 promoter also served as a gene tag and as a promoter to upregulate genes if inserted before the start codon of a gene. The particular *A. tumefaciens* strain used was EHA 105, which is considered to be a hypervirulent (Hood et al., 1993). However, other *A. tumefaciens* strains, e.g., A136 and EHA 101, produce similar transformation frequencies in *T. reesei*. *A. rhizogenes* strains, e.g., ATCC 43057, can also be used. The particular disruption library contained about 50,000 transformants.

B. *Trichoderma reesei* MAGI Strain

The *T. reesei* Morph 1.1 (i.e., "Morph") mutant is deleted for four major cellulases genes (i.e., cbhI, cbhII, eglI and eglII), which makes it useful for expressing other proteins in the absence of cellulase background activity. The MAGI strain was generated by targeting the insertion of a reporter cassette to the orotidine 5'-monophosphate pyrophosphorylase (pyr2) locus of *Trichoderma reesei* Morph 1.1. This reporter cassette contains a codon optimized green fluorescent protein (GFP) from *Ptilosarcus* species and an alpha-amylase under the control of the *T. reesei* cellobiohydrolase I (cbhI) promoter and transcriptional terminator sequences. A hygromycin B phosphotransferase gene is also integrated with the reporters at the pyr2 locus. Coincident with integration of the reporter cassette, a 3' portion of the pyr2 gene is deleted making the strains uridine auxotrophs.

C. Preparation of DNA

The vector used for disruption was pRATT 236 based on the PZP 100 vector, which includes the left and right T-DNA border regions, a pBR322 born site for mobilization from *E. coli* to *Agrobacterium*, ColE1 and pVS1 plasmid origins for replication in *E. coli* and *Agrobacterium*, respectively, and a bacterial marker for conferring chloramphenicol resistance (Hajdukiewiez, O. et al., 1994). A representation of the vector is shown in FIG. 1.

A disruption cassette containing the pyr2 gene of *Trichoderma atroviride* followed by the his1 promoter oriented to transcribe outward into the insertion site was prepared by standard molecular biology techniques and ligated to generate the pRATT 236 vector. The resulting vector was propagated in *E. coli* TOP10 cells (Invitrogen, Carlsbad, Calif., USA). LA agar plates (10 g/L tryptone, 5 g/L yeast extract, 10 g/L NaCl, 10 g/L agar) with 25 ppm chloramphenicol were used to select for *E. coli* transformants. *E. coli* containing the vector were grown in LB medium (10 g/L tryptone, 5 g/L yeast extract, 10 g/L NaCl) plus 25 ppm chloramphenicol. Vector DNA was isolated using standard methods.

D. Transformation of *Agrobacterium* Cells

Competent *Agrobacterium* cells were made as follows. Briefly, *Agrobacterium* cells were revived from cryopreservation by growing on LA medium at 28° C. for about three days. Colonies were then selected and grown in LB medium containing 0.1% glucose in 50 ml volumes in 250 ml dented bottom flasks at 28° C. until growth was apparent. Alternatively, colonies were started in a 5 ml culture tube and transferred to a 250 ml flask when growth was apparent. About 10% of the volume of the 250 ml flask was then transferred into a fresh flask with the same medium, which was grown to an OD (600 nm; $OD_{600}$) of about 0.4-0.8 (about 5-6 hours of growth). The cells were recovered by centrifugation in a cold centrifuge at 10,000 rpm for 10 minutes, and then washed three times in cold 1 M HEPES, pH 7.0. Next, the cells were washed once in cold 1 mM HEPES with 10% glycerol, and aliquots were frozen at −70° C. Cell viability was determined (typically about $1 \times 10^9$ CFU/ml after freezing).

The vector DNA was used to transform *Agrobacterium* cells by electroporation. Competent *Agrobacterium* cells were thawed on ice and about 40 μl of the cells were mixed with about 1 μg of DNA in a 0.2 cm electroporation cell (on ice). The cells were electroporated at 2.5 volts (200 Ohms, at 25 µF) with a Buchler 3-150 electroporator. SOC medium (Invitrogen) was added to the electroporation cell immediately after electroporation. Alternatively, the *Agrobacterium* cells can be transformed by electroporation using the ligation mixture, thereby eliminating the need to propagate the vector DNA in *E. coli*. In the alternative method, about 1 µl of the ligation mixture is used for transformation. After the addition of SOC to the electroporation mixture, dilutions of the mixture were plated onto LA medium plus 250 ppm chloramphenicol culture plates and incubated at 28° C. for four days. $1 \times 10^7$ CFU/ml of *Agrobacterium* transformants were obtained and about 90-100% contained the vector DNA, as determined by PCR analysis. As little at 25 ppm chloramphenicol can be used to obtain colonies in a shorter time frame but a larger number of colonies must to be screened to identify bonafide transformants.

E. *Agrobacterium*-mediated Transformation of *T. reesei*

25 ml of minimal medium (2.05 g/L $K_2HPO_4$, 1.45 g/L $KH_2PO_4$, 0.15 g/L NaCl, 0.5 g/L $MgSO_4.7H_2O$, 0.1 g/L $CaCl_2.6H_2O$, 0.0025 g/L, $FeSO_4.7H_2O$, 0.5 g/L $(NH_4)_2SO_4$, and 2 g/L glucose, with 25 ppm chloramphenicol added after sterilization) in a 250 ml flask was inoculated with either a frozen stock of vector-transformed *Agrobacterium* or directly from a fresh LA plate. The minimal medium culture was then incubated at 28° C. with shaking until cloudy (overnight to several days). 10 ml of the culture was transferred to 50 ml of induction medium (2.05 g/L $K_2HPO_4$, 1.45 g/L $KH_2PO_4$, 0.15 g/L NaCl, 0.5 g/L $MgSO_4.7H_2O$, 0.1 g/L $CaCl_2.6H_2O$, 0.0025 g/L, $FeSO_4.7H_2O$, 0.5 g/L $(NH_4)_2SO_4$, 1.8 g/L glucose, 5 g/L glycerol, prepared in 40 mM MES, pH 5.3, with 200 µL of 1 M acetosyringone added after sterilization) in 250 ml flasks. The staring $OD_{600}$ was about 0.1, and the vector-transformed *Agrobacterium* cells were grown to an $OD_{600}$ of about 0.4-0.8.

A fresh culture of *T. reesei* MAGI cells was prepared by resuspending spores in 10 ml of sterile water. Transformation of the *T. reesei* MAGI cells was performed as follows: About 100 µl of *Agrobacterium* whole broth ($OD_{600}$=0.4-0.8) was mixed with 100 µl of fungal spores ($10^7$ sfu/ml) in a tube (other ratios of *Agrobacterium* cells to fungal spores will also produce satisfactory results). About 0.1-1.0 ml of this mix was plated onto induction agar plates (induction medium with 15 g/L agar and 0.25 mg/mL uridine) with embedded nitrocellulose filters. The plates were incubated at about 18-28° C. for about 24-48 hours to allow the growth of the *T. reesei* cells. Next, the nitrocellulose filters were transferred to Vogel's medium (Vogel, *Microbiol. Genet. Bull.* 13:42-43, 1956) supplemented with 250 ppm carbenicillin to kill/inhibit *Agrobacterium* growth. The cultures were then incubated at 28° C. until growth of filamentous fungi (representing transformants of the disruption library) on the filters was evident.

F. Screening for Morphology Mutants

Transformants in the disruption library were screened for alterations in morphology in solid and liquid culture using light microscopy. Following transformation, individual transformants were picked from the nitrocellulose filters using a colony picker and transferred to 96-well microtiter plates containing potato dextrose agar (CP-700, Norgren Systems LLC, Fairlea, W. Va., USA). Alternatively, spores from transformants were combined, germinated, and single spores were added to microtiter wells using a cell sorter. Spores were collected by suspending spores from a potato dextrose transformation plate in 20 ml sterile distilled water using a cell spreader. Spores were inoculated into a 250 mL flask containing 50 ml of a minimal medium and incubated at 28° C. with agitation for 24 h until germlings were obtained. Using high speed sorting (MoFlo sorter, Cytomation, Fort Collins, Colo., USA) at an event rate of 15,000 event per second, 60 psi with a 70 µm nozzle), individual germlings were separated into microtiter plate wells containing potato dextrose agar (Difco, Detroit, Mich., USA). The microtiter plates containing the transformants obtained by either method described above, were incubated for 7 days at 28° C. The individual germinates spores were replicate plated into 384 well black sensoplates with glass bottoms (Greiner Bio-one, Germany) containing YEG (5 g yeast extract, 20 g glucose per 1 L water) and incubated at 20° C., for 24 h. The morphology of individual transformants was examined microscopically.

Alternately, slow growing transformants were isolated directly from the transformation plates and re-plated on potato dextrose agar (Difco). Transformants showing colonial growth on the potato dextrose plates were grown in YEG medium in shake flasks at 28° C., 150 rpm, for 24 h and the morphology of the transformants was examined microscopically.

G. Isolation and Characterization of *T. reesei* MAGI 10-8 g

Mutant MAGI 10-8 g obtained from the above procedure was observed to have altered morphology in liquid culture having shorter filaments than the MAGI parent. In liquid medium, cultures containing the MAGI 10-8 g mutant also showed a higher level of dissolved oxygen during growth compared to cultures containing the MAGI parent (Table 1).

Strains MAGI and MAGI 10-8 g were grown under similar conditions in submerged (liquid) culture, and their growth phenotypes were compared. Briefly, spores of each strain were added separately to 500-mL of minimal medium in a 3-L flask with both side and bottom baffles. After autoclaving for 30 minutes, sterile 60% glucose was added to a final concentration of 27.5 g/L. Since the MAGI strain is Δpyr2 it was supplemented with 2 mg/mL uridine. The culture was grown for 48 hrs at 34° C. in a shaking incubator.

After 48 hrs, the contents of each flask were added separately to 14-L fermentors containing 9.5 L of medium containing 4.7 g/L $KH_2PO_4$, 1.0 g/L $MgSO_4.7H_2O$, 4.3 g/L $(NH_4)_2SO_4$ and 2.5 mL/L of the same trace element solution. These components were heat sterilized together at 121° C. for 30 minutes. A solution of 60% glucose and 0.48% $CaCl_2.2H_2O$ was separately autoclaved, cooled, and added to the fermentor to a final concentration of 75 g/L glucose and 0.6 g/L $CaCl_2.2H_2O$. The medium was adjusted to pH 3.5 with 28% $NH_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO content levels dropped, at least partly as a consequence of the increased viscosity of the broth due to the proliferation of filamentous fungus hyphae. When DO content levels fell below 40%, the agitation rate was increased to maintain the dissolved oxygen at 40%. Upon reaching 750 rpm agitation, DO content level would be allowed to drop below 40%. If the DO content did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for all both strains.

The DO content level in each fermentor at a given level of agitation, and the amount of agitation required to maintain a given DO content level are indirect measures of the viscosity of the different broths, due to the different strain growth phenotypes. Although it would be ideal to vary only one variable (i.e., DO or agitation) and measure the other, it is desirable to prevent the DO from falling below 40% to in production of sufficient biomass in each fermentor, thereby permitting a more meaningful comparison between the growth of the different strains.

Generally, where it is necessary to increase the agitation rate to maintain a target DO level, the amount of agitation can be estimated by the amount of power supplied to the motor driving the fermentor turbine, which provides a metric that correlates with the viscosity of the broth. In particular, the extra power required to agitate the suspended culture is proportional to the agitation rate raised to the 3rd power.

The nucleic acid sequence of the mpg1 gene was obtained from the JGI data base: Protein ID: 122551, Name: estExt_fgenesh5_pg.C_130115, available at: http://genome.jgi-psf.org/cgi-bin/dispGeneModel?db=Trire2&id=122551, (The Genome Portal of the Department of Energy Joint Genome Institute I. V. Grigoriev, H. Nordberg, I. Shabalov, A. Aerts, M. Cantor, D. Goodstein, A. Kuo, S. Minovitsky, R. Nikitin, R. A. Ohm, R. Otillar, A. Poliakov, I. Ratnere, R. Riley, T. Smirnova, D. Rokhsar, and I. Dubchak Nucleic Acids Res 2011 0: gkr947v1-gkr947) as disclosed below. The untranslated region is italicized and flanked 5' and 3' by upstream or downstream sequence, coding regions are in bold and introns are in lower case (SEQ ID NO: 38):

```
GGCAAGGCGTACGCATGAGCGGAGCGGCAGTAGGTACTTGCGCCTCCGTGCTCATCTGCTGCCC

GCAGCGCGTACCGGCGTCGTGACATCTGGACACCTCGTTCGTCCCTACTTTAGATCCATCCAGC

CCGAACCTCATTTTCCTCTCTCCTTTTCCCTTCCATCCTCCCGCAACCACCGCGTCTTTTCTTC

CCTCCCGAGCCGACACTCGAGTCTCTGCCCTGCGAGCATTGCACCGTCGCTCGTTCTTCTCTAC

GCTCACTATCCAACATACTAGTTTATTCTTTTTCCCTTCTTCTACCATCTTCTGCCTCTTTACT

TACGAAATCAAACCCCCCCCTTTAAAACATCCACGAATCTCCTTTGCACTTCAGCTTCGTCGCA

TACATTCACCATGAAGGgtaggtgacgcgccggttcccaatctgcccatcattggcttcactc cagctccaatggcaagatctcgctgacaatctctctccctgcgcagGACTTATTCTTGTCGGC GGCTTTGGCACTCGCCTTCGCCCTCTCgtacgtccacgccagcaccaccagcagcgatccgacc tgcatcccactaccgcattgacgcggatggggtggcatggaggggaaaaccaccataagcgca gcctctcacaccgcgaacctccactgaccattgtgcgacgccaatctagACCCTGACGCTCCC

CAAGCCTCTGGTTGAGTTCTGCAACAAGCCCATGATTGTGCACCAGATCGAGGCTCTCGTCGCC

GCTGGCGTGACCGACATTGTCCTCGCCGTCAACTACGCCCAGAAATCATGGAAAAGTTCCTGG

CCGAGgtgagtcgtgcacatcacaccctatgaccctcactacaaaccttgcctattcgcctg cccattcgctgtaccaagcttttcgcccccccccccccccctccctcccctcctactcagc atatctcccccaccaatgacaatggacgcaaaggctgattgcgtacgctcgaccgtttagTA

CGAGGAGAAATACAACATCAACATTGAGTTCTCCGTCGAGTCGGAGCCCCTCGACACCGCCGGC

CCCCTCAAGCTTGCTGAGCGCATCCTCGGCAAGGATGACTCGCCCTTCTTCGTCCTCAACTCCG

ACGTCATCTGCGACTATCCCTTCAAGGAGCTCCTCGAGTTCCACAAGGCCCACGGCGATGAGGG

CACCATTGTCGTCACCAAGGTCGAGGAGCCGTCCAAGTACGGTGTCGTCGTCCACAAGCCCAAC

CACCCCTCGCGCATCGACCGCTTCGTCGAGAAGCCCGTCGAGTTCGTCGGCAACCGCATCAACG

CCGGCATGTACATCTTCAACCCCTCCGTCCTGAAGCGCATCGAGCTTCGCCCCACGTCGATCGA

GAAGGAGACGTTCCCCGCCATGGTTGCCGACAACCAGCTGCACTCGTTCGATCTCGAGGGCTTC

TGGATGGACGTTGGCCAGCCCAAGGACTTCCTCAGCGGCACCTGCCTGTACCTGTCCTCCCTCA

CCAAGAAGGGCAGCAAGGAGCTGACCCCTCCCACCGAGCCCTACGTTCACGGCGGCAACGTCAT

GATTCACCCTTCGGCCAAGATTGGAAAGAACTGCAGAATAGGCCCCAATGTCACCATTGGCCCG

GATGTTGTCGTCGGTGACGGCGTCCGCCTGCAGCGATGCGTCCTCCTCAAGGGCTCCAAGGTCA

AGGACCACGCCTGGGTCAAGTCGACGATTGTTGGCTGGAACAGCACCGTCGGTCGCTGGGCCCG

TCTCGAGAATGTGACTGTTCTCGGTGACGACGTGACCATTGGCGACGAGATTTACGTCAACGGC
```

-continued

```
GGCAGCGTCCTGCCTCACAAGTCCATCAAGGCCAACGTTGACGTTCCCGCCATCATTATGTGAT

TTATCTCATGTTGTCACGCATCCTTGGCTCGCATGGGCGTTTTTGTTCCCCATGCGCTGCTTTC

CGAGATGATCTTTGTTTCTTCTTCAAACCCCATCTTTTCTTCTTTTAACTTGACATTTCTCTTT

TTTTTTTTTTTTCCTTTTACAGAACCCCATTTACGCCTTACCGCAAACTCACCACTCCTCCGC

TATTCTCAAGAGATACCCTATATTGGTGGGGGAAACAGTCTTTGAGAGAAAAGAAAACCAAGCC

ACATTTTATATAATTACTACTAGTCTCGACATCTTTTTTCCCTTTCTTCTTCTTCCTCAAGAAA

AAAGATGTCGTGTACACTTATGTTGAGCCCCAAGTAAATCGTTTGGCGTCTCGGGGAACCGGTT

GGCAAAGCATTCTTGGAGGGACAGGGACGAGGGCTGAGGGTTGAGAAGAGCAATGACGGACGAG

GCACTCAAGATTTCCATGTATGAAAAGATGATAGCGTAGCGAATGAAGTGTATTTACGCTTGCG

CCGACTGTGTTGTCTGGTGACGCGATTGCTGAGGTCGAGCTTGTCCAGTACGAGCACTGCTTGA

AGATGAACAAATCGAGGTGGTTCCCCCATAGGCTGACCTTATACAGAATTTCGCTATGCATCAG

AAGTAAGTCGTTATCACATTTGATGAGATAGCATCTCCGCTCACTTGTCATTTCAGTTAGAATA

TTCATT
```

As shown in Table 1, MAGI 10-8 g has a reduction in broth viscosity compared to the parent MAGI. At the end of the batch growth phase, when all the glucose has been consumed, both strains had achieved a similar biomass concentration. To get there, the MAGI control strain saw agitation increased to the maximum of 750 rpm and then saw DO drop down to as low as 35%. The strain MAGI 10-8 g did not require as much energy to achieve the same biomass concentration. Agitation rate was increased slightly to 513 rpm when the % DO dropped to 40. Protein production was not adversely affected in MAGI 10-8 g compared to MAGI (not shown).

TABLE 1

Broth viscosity of MAGI compared to MAGI 10-8 g

| Strain | Deletion | DO (%) | Agitation (rpm) | Biomass (g/kg) | CER (mmol/L/hr) |
|---|---|---|---|---|---|
| MAGI | none | 35 | 750 | 39 | 125 |
| MAGI 10-8 g | mpg1 | 40 | 513 | 40 | 128 |

Inverse PCR was used to identify the insertion site of the T-DNA containing the pyr2 his1 genes in the *T. reesei* genome. Briefly, high molecular-weight genomic DNA from strain MAGI 10-8 g was digested to completion with the restriction enzyme SpeI. After heat inactivation of the enzymes, the reaction was diluted five-fold in ligation buffer and T4 DNA ligase was added. Following an overnight ligation reaction, the ligase was heat inactivated and the reaction was precipitated with ammonium acetate and ethanol. The washed DNA pellet was dissolved in TE and used as template for PCR with primers RPG253 and RPG255 (referring to Table 2). The resulting PCR product was cleaned then sequenced with nested primers RPG239 and RPG207 to determine the nucleotide sequence flanking the site of the T-DNA insertion. BLASTn analysis of this sequence against the JGI *Trichoderma reesei* v 2.0 genome sequence revealed that the T-DNA had deleted the region 369089 to 370324 of Scaffold 13.

The site of insertion was confirmed by PCR using primers homologous to the genomic DNA flanking the insertion site and primers homologous to the T-DNA. In particular, primers RPG256 and RPG268 were used to confirm the sequence at the 3' end of the T-DNA and primers RPG268 and RPG269 amplified the full T-DNA insertion at the identified site.

The site of the T-DNA insertion in mutant MAGI 10-8 g was at Scaffold 13 from 369089 to 370324 in the *T. reesei* JGI genomic database v2. The gene found at this site is the mpg1 gene (PDI 122551) which is found in other fungi including *Aspergillus clavatus*, *Aspergillus fumigatus*, and *Neosartorya fischeri*. As described by Kruszewska et al. (1998) *Cur. Genet.* 33:445-50 and Zakrzewska et al. (2003) *Applied and Environmental Microbiology* 69:4383-4389 mpg1 from *Trichoderma reesei* encodes for a GTP:alpha-D-mannose-1-phoshate guanyltransferase which can play a major regulatory role in early stages of protein glycosylation. Southern analysis showed that this strain contained only one copy of the pyr2 gene in addition to the native copy indicating that one disruption event had taken place (not shown).

Since the insertion at this site was shown to be the only genetic change made in the MAGI 10-8 g strain, it follows that disruption of the mpg1 gene was responsible for the observed morphological changes.

TABLE 2

Primers used in Example 1.

| Primer | Sequence | SEQ ID NO |
|---|---|---|
| RPG253 | 5'-TTCCTGACAACGAGGACATCTCAAGCTGT-3' | 17 |
| RPG255 | 5'-CAAACATAGCAGCGTCCATTGCACGA-3' | 18 |
| RPG239 | 5'-GGGGACAAGTTTGTACAAAAAAGCAGGCTTG-ATGGTTGACTATTGGGTTTCTGTGC-3' | 19 |
| RPG207 | 5'-GTCGCCCGTCTCCGTTGT-3' | 20 |
| RPG256 | 5'-GCTTTCGAGCTCACACGACATCCTTCA-3' | 21 |
| RPG268 | 5'-TCCCCGAGACGCCAAACGA-3' | 22 |
| RPG269 | 5'-GGCCGAGGACCCTTCCATCA-3' | 23 |

Example 2

Deletion of the Mpg1 Gene from *T. reesei* Mutant 77B7

A. Morph Strain TrGA 77B7

The Morph strain, described above, was previously transformed with a native *Trichoderma* glucoamylase gene (TrGA) under control of the CBH1 promoter, using amds as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoro-orotic acid (FOA) selection.

B. Generation of a Mpg1 Disruption Cassette

The *Trichoderma reesei* mpg1 ((jgi|Trire2|122551) was deleted from mutant Morph 77B7.

Figure 2:
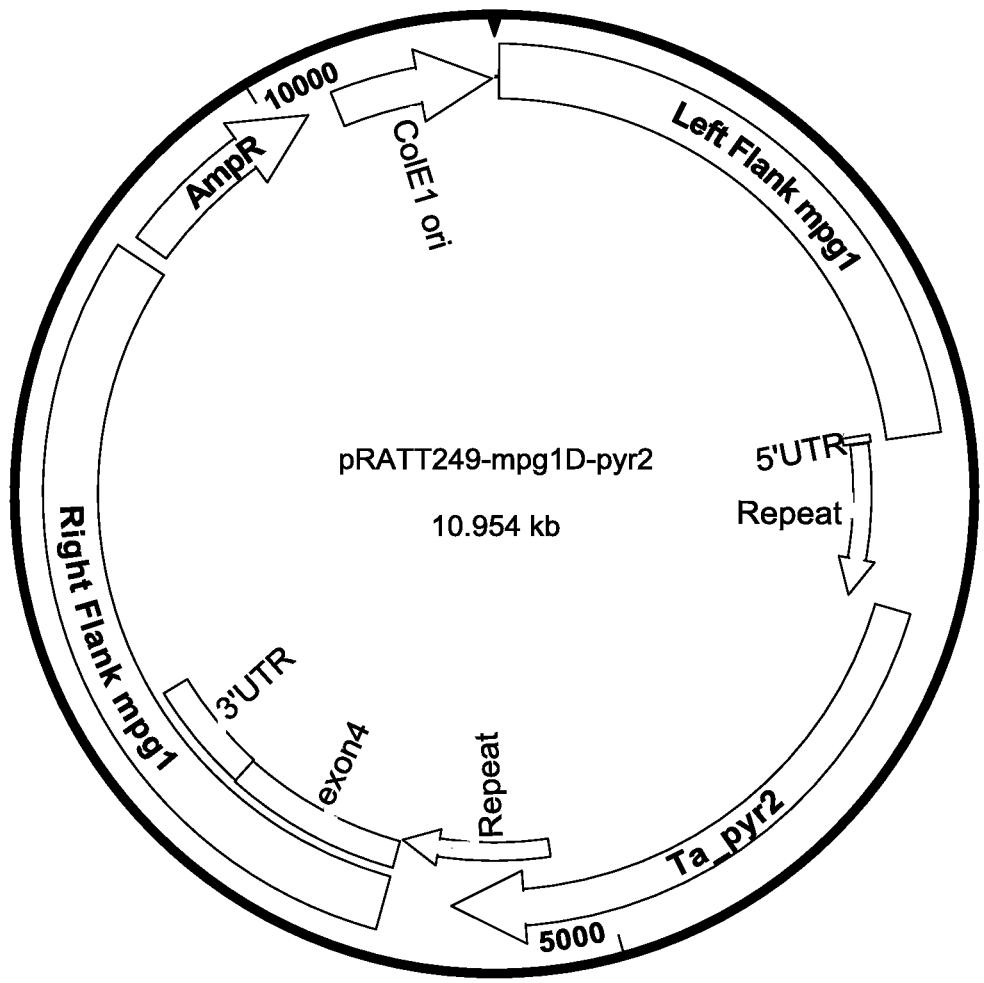
FIG. 2 is a map of the mpg1 disruption vector.

The mpg1 disruption cassette plasmid pRATT249 (FIG. 2) was prepared using standard molecular biology procedures. This plasmid included a DNA sequence having a 2.5 Kb region homologous to the DNA sequence spanning part of the 5' untranslated region and contiguous upstream sequences (Left Flank). Also included within the plasmid was a DNA sequence having a 3.3 Kb region homologous to the DNA sequence spanning part of the fourth exon of the mpg/gene and contiguous downstream sequences (Right Flank). These sequences were designed to target the mpg1 gene and replace the regions of the genome between the Left and Right Flanks with the intervening cassette sequences. These intervening sequences included a pyr2 selection marker from *Trichoderma atroviride* intended to minimize homology to the endogenous *T. reesei* pyr2 in the genome of the strain to be transformed. Immediately upstream of the pyr2 selection marker was a directly repeated duplication of the 3' end of the marker, which facilitated the subsequent loss of the marker and isolation of useful pyr2 mutant derivatives of the transformants/disruptants. This full mpg1 disruption cassette was amplified by PCR using primers RPG388 and RPG391. Multiple PCR reactions were pooled and cleaned using standard molecular biology procedures for use in the subsequent steps.

C. Generation of Strain Morph 77B7 Δmpg1

Strain Morph TrGA 77B7 Δ pyr2 was transformed with the mpg1 disruption cassette using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the mpg1 disruption cassette integrated at the mpg1 locus by homologous recombination. Homologous integration of the Δmpg1 disruption cassette at the mpg1 locus was verified by amplifying DNA fragments of the expected sizes using two primer pairs. Primer pair RPG394 and RPG253 amplified a DNA fragment starting outside the 5' end of the disruption cassette region and ending within the 3' region. Primer pair RPG395 and RPG273 amplified a DNA fragment starting within the 5' region of the disruption cassette and ending outside the 3' end of the disruption cassette region. The generated strain with confirmed homologous integration of the mpg 1 disruption cassette was named Morph 77B7 Δ mpg1. Primer sequences are listed in Table 4

Strains Morph 77B7 and Morph 77B7 Δ mpg1 were grown under identical conditions in submerged (liquid) culture, and their growth phenotypes were compared. Briefly, spores of each strain were added separately to 500-mL of medium in a 3-L flask with both side and bottom baffles. The medium contained 5 g/L $(NH_4)_2SO_4$, 4.5 g/L $KH_2PO_4$, 1 g/L $MgSO_4.7H_2O$, and 14.4 g/L citric acid, adjusted to pH 5.5 with 5% NaOH. After autoclaving for 30 minutes, sterile 60% glucose was added to a final concentration of 27.5 g/L, along with 2.5 mL/L of a trace element solution containing 175 g/L citric acid, 200 g/L $FeSO_4.7H_2O$, 16 g/L $ZnSO_4.7H_2O$, 3.2 g/L $CuSO_4.5H_2O$, 1.4 g/L $MnSO_4.H_2O$, and 0.8 g/L $H_3BO_3$. The culture was grown for 48 hrs at 34° C. in a shaking incubator.

After 48 hrs, the contents of each flask were added separately to 14-L fermentors containing 9.5 L of medium containing 4.7 g/L $KH_2PO_4$, 1.0 g/L $MgSO_4.7H_2O$, 4.3 g/L $(NH_4)_2SO_4$ and 2.5 mL/L of the same trace element solution. These components were heat sterilized together at 121° C. for 30 minutes. A solution of 60% glucose and 0.48% $CaCl_2.2H_2O$ was separately autoclaved, cooled, and added to the fermentor to a final concentration of 75 g/L glucose and 0.6 g/L $CaCl_2.2H_2O$. The medium was adjusted to pH 3.5 with 28% $NH_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO levels dropped, at least partly as a consequence of the increased viscosity of the broth due to the proliferation of filamentous fungus hyphae. When DO fell below 40%, the agitation rate was increased to maintain the dissolved oxygen at 40%. Upon reaching 750 rpm agitation, DO would be allowed to drop below 40%. If the DO did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for all both strains.

The DO level in each fermentor at a given level of agitation, and the amount of agitation required to maintain a given DO level are indirect measures of the viscosity of the different broths, due to the different strain growth phenotypes. Although it would be ideal to vary only one variable (i.e., DO or agitation) and measure the other, it is desirable to prevent the DO from falling below 40% to ensure the production of sufficient biomass in each fermentor, thereby permitting a more meaningful comparison between the growth of the different strains.

Generally, where it is necessary to increase the agitation rate to maintain a target DO level, the amount of agitation can be estimated by the amount of power supplied to the motor driving the fermentor turbine, which provides a metric that correlates with the viscosity of the broth. In particular, the extra power required to agitate the suspended culture is proportional to the agitation rate raised to the 3rd power.

For strains where the % DO does not fall below 40%, the metric is based on the minimal dissolved oxygen levels that were maintained at the preselected agitation rate), As shown in Table 3, deletion of the mpg1 gene from strain Morph 77B7 resulted in a strain (Morph 77B7 Δ mpg1) having a reduction in broth viscosity. At the end of the batch growth phase, when all the glucose has been consumed, both strains had achieved a similar biomass concentration. To get there, the control strain saw agitation increased to 616 rpm when the DO drop down to as low as 40%. The mpg1-deleted strain did not require as much energy to achieve the same biomass concentration. Agitation rate was never increased above 500 rpm and DO dropped only as low as 102%.

TABLE 3

Broth viscosity in Morph 77B7 with and without the mpg1 gene

| Strain | Deletion | DO (%) | Agitation (rpm) | Biomass (g/kg) | CER (mmol/L/hr) |
|---|---|---|---|---|---|
| Morph77B7 | None | 40 | 616 | 40 | 141 |
| Morph 77B7Δmpg1 | mpg1 | 102 | 500 | 42 | 118 |

TABLE 4

Primers used in Example 2

| Primer | Sequence | SEQ ID NO |
|---|---|---|
| RPG388 | 5'-CCCCTCCGGATGAGGTGGCTTGTGGCT-3' | 24 |
| RPG391 | 5'-GGCGGCTAGCAGACGCACTCGTAGAGCAAGGT-3' | 25 |
| RPG394 | 5'-AGGTCCGATCAACGACTCTGGCAAC-3' | 26 |
| RPG253 | 5'-TTCCTGACAACGAGGACATCTCAAGCTGT-3' | 27 |
| RPG395 | 5'-GGGTTGTCGTTAGCTAACCAGAGCGTAA-3' | 28 |
| RPG273 | 5'-GGTCAGTAACATAGCAGGACTATAGTAGTGGCTCAC-3' | 29 |

Example 3

Additive Viscosity Reduction in Mutants Having Disrupted Mpg1 and Seb1 Genes

A. Morph 77B7 Δ mpg1, described above, was previously transformed with a native *Trichoderma* glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce mutant (77B7) having altered morphology associated with a low viscosity phenotype. The mpg1 gene was deleted as described above. The pyr2 gene was subsequently spontaneously deleted by selecting for resistance to 5-fluoroorotic acid creating strain Morph 77B7 Δ mpg1, Δpyr2.

B. Generation of a Seb1 Disruption Cassette

Figure 3:
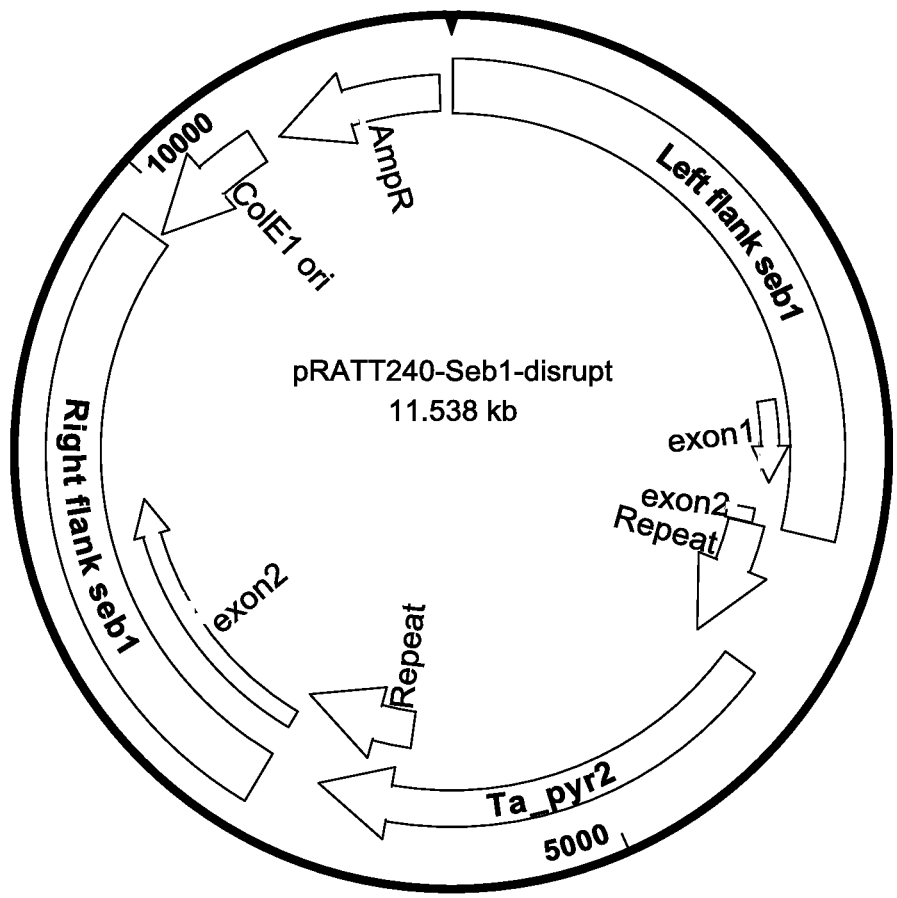
FIG. 3 is a map of the seb1 disruption vector.

The seb1 disruption cassette plasmid pRATT240 (FIG. 3) was prepared using standard molecular biology procedures. These intervening sequences included a pyr2 selection marker from *Trichoderma atroviride* intended to minimize homology to the endogenous *T. reesei* pyr2 in the genome of the strain to be transformed. Immediately upstream of the pyr2 selection marker was a duplication of the 3' end of the marker, which direct repeat facilitated the subsequent loss of the marker and isolation of useful pyr2 mutant derivatives of the transformants/disruptants. This full seb1 disruption cassette was amplified by PCR using primers RPG257 and RPG264 (referring to Table 6). Multiple PCR reactions were pooled and cleaned using standard molecular biology procedures for use in the subsequent steps.

C. Generation of Strain Morph 77B7 Δ mpg1Δseb1 and Morph 77B7 Δ Seb1

Morph 77B7 Δpyr2 and Morph 77B7 Δmpg1 Δpyr2 were transformed with the seb1 disruption cassette using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the seb1 disruption cassette integrated at the seb1 locus by homologous recombination. Homologous integration of the Δseb1 disruption cassette at the seb1 locus was verified by amplifying DNA fragments of the expected sizes using two primer pairs. Primer pair RPG297 and RPG253 amplified a DNA fragment starting outside the 5' end of the disruption cassette region and ending within 3' region. Primer pair RPG296 and RPG273 amplified a DNA fragment starting within the 5' region of the disruption cassette and ending outside the 3' end of the disruption cassette region. Consistent with disruption, a third primer pair, RPG133 and RPG220, amplified a 1.6 kb DNA fragment spanning the insertion site using template DNA from the untransformed parental strain but failed to amplify this fragment using template DNA from the seb1 disruption strain. The generated strains with confirmed homologous integration of the seb1 disruption cassette was named Morph 77B7 Δseb1 and Morph 77B7 Δ mpg1 Δ seb1.

D. Growth of Morph 77B7 Δ Mpg1 Δseb1 in Submerged Culture

Strains Morph 77B7 Δ mpg1 and Morph 77B7 Δ mpg1 Δseb1 were grown under identical conditions in submerged (liquid) culture as described in Example 2, and their growth phenotypes were compared. As shown in Table 5, disruption of the seb1 gene in the Morph 77B7 Δ mpg1 strain resulted in a strain having a further reduction in viscosity (based on the minimal maintained dissolved oxygen levels at the preselected agitation rate), indicating that disruption of the seb1 gene and disruption of the mpg1 gene have an additive effect with respect to morphology and viscosity reduction. Protein production of Morph 77B7 Δmpg1 Δseb1 was at least 85% or higher of that of Morph TrGA 77B7 and Morph TrGA 77B7Δseb1.

TABLE 5

Broth viscosity of Morph 77B7 Δ seb1, Morph 77B7 Δmpg1, and Morph Δ mpg1 Δseb1

| Strain | Deletion | DO (%) | Agitation (rpm) | Biomass (g/kg) | CER (mmol/L/hr) |
|---|---|---|---|---|---|
| Morph 77B7Δseb1 | seb1 | 101 | 500 | 41 | 127 |
| Morph 77B7 Δmpg1 | mpg1 | 102 | 500 | 42 | 118 |
| Morph TrGA 77B7Δmpg1Δseb1 | mpg1, seb1 | 110 | 500 | 47 | 112 |

TABLE 6

Primers used in Example 3.

| Primer | Sequence | SEQ ID NO |
|---|---|---|
| RPG257 | 5'-AGATACTAGTGCGAGGCATCCGTGATGGATCTC-3' | 30 |
| RPG264 | 5'-GGGTCCCGGGCTCGGGAGCGTAACTCTTGTCC-3' | 31 |

TABLE 6-continued

Primers used in Example 3.

| Primer | Sequence | SEQ ID NO |
|---|---|---|
| RPG297 | 5'-CGCCGTCAGTTGACGACAGTGCT-3' | 32 |
| RPG253 | 5'-TTCCTGACAACGAGGACATCTCAAGCTGT-3' | 33 |
| RPG296 | 5'-CACCGGTGAAGCCTTCCGTGAGT-3' | 34 |
| RPG273 | 5'-GGTCAGTAACATAGCAGGACTATAGTAGTGGCTCAC-3' | 35 |
| RPG133 | 5'-GGAGCCAACAGAGACGGTCAGGTT-3' | 36 |
| RPG220 | 5'-GCCCAGCGTCGAGTGAGACAAGT-3' | 37 |

Example 4

Additive Viscosity Reduction in Mutants Having Disrupted Mpg1 and Sfb3 Genes

A. Morph Strain TrGA #32

The Morph strain, described above, was previously transformed with a native Trichoderma glucoamylase gene (TrGA) under control of the CBH1 promoter, using amds as a marker. A transformant containing two tandom copies of glucoamylase (TrGA 29-9) was subsequently isolated, and random chemical mutagenesis was used to produce a cell wall mutant (70H2) having altered morphology associated with a reduced viscosity phenotype. This reduced viscosity phenotype was later determined to be the result of a truncated sfb3 gene (data not shown). A 70H2 strain transformed with additional copies of TrGA (i.e., TrGA #32) has further been useful for over-expressing TrGA.

B. Generation of a Mpg1 Disruption Cassette

The mpg1 gene was disrupted as described in Example 2 to make strain TrGA #32 Δmpg1.

C. Growth of TrGA#32 Δmpg1 in Submerged Culture

Strains TrGA#32 and TrGA#32 Δmpg1 were grown under identical conditions in submerged (liquid) culture as described in Example 2, and their growth phenotypes were compared. As shown in Table 7, deletion of the mpg1 gene from the TrGA#32 strain resulted in a strain having a further reduction in viscosity (based on the rpm required to maintain a preselected level of dissolved oxygen), indicating that disruption of the mpg1 gene and disruption of the sfb3 gene have an additive effect with respect to morphology and viscosity reduction. Protein production was not affected by the mpg1 deletion (not shown).

TABLE 7

Growth characteristics of TrGA #32 and TrGA #32 Δmpg1 in liquid medium.

| Strain | Deletion(s) | DO (%) | Agitation (rpm) | Biomass (g/kg) | CER (mmol/L/hr) |
|---|---|---|---|---|---|
| TrGA #32 | sfb3 | 40 | 618 | 38 | 147 |
| TrGA #32 Δmpg1 | sfb3\|mpg1 | 40 | 589 | 41 | 153 |

Example 5

Additive Viscosity Reduction in Mutants Having Disrupted at Least One of Gas1, Crz1 and Tps2 Genes in Conjunction with Disrupted Mpg1, Seb1, and/or Sbf3

A. Viscosity Reduction in Disrupted Gas1

The Gel/Gas/Phr family of fungal β(1,3)-glucanosyltransferases plays an important role in cell wall biogenesis by processing the main component β(1,3)-glucan (Popolo et al., 2008). gas1 (PID 22914) encodes a beta-1,3-glucanosyltransferase that is a GPI (and/or glucan)-anchored protein capable of breaking and joining beta-1,3-glucans. There are multiple paralogs in many fungal genomes including T. reesei, which has five. Separate studies have shown that mutation of the gas1 gene (or the gel1 gene as it is known in Aspergillus fumigatus) affects fungal cell wall structure, and can lead to morphological changes as well as hypersensitivity to Calcofluor White, Congo Red and sodium dodecyl sulfate (Schirawski, J. et al. 2005, Mouyna, I. et al. 2005).

A Trichoderma reesei Morph strain was deleted for four major cellulase genes, including cbhI, cbhII, egII and egIV, which makes it particular suitable for expressing other proteins in the absence of or in reduced cellulase background. See, WO 05/001036. The Morph strain had been previously transformed with a native Trichoderma glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoroorotic acid (FOA) selection. The Trichoderma reesei gas1 (PID 22914) was deleted from mutant Morph 77B7.

Strain Morph TrGA 77B7 Δpyr2 was transformed with a gas1 disruption cassette using PEG-mediated transformation, and plated on Vogel's minimal medium containing sorbitol to select for candidates based on uridine prototrophy acquired by the pyr2 marker. As shown in Table 8, Morph 77B7 Δgas1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δgas1 did not require as much energy (i.e., rpm increase in agitation) to achieve the same biomass concentration. Agitation rate never increased above 500 rpm and the % DO never dropped below 115. Protein production was not adversely affected in Morph 77B7 Δgas1 compared to Morph 77B7 (data not shown). Details of the gas1 disruption can be found in U.S. Provisional Application No. 61/480,602, filed Apr. 29, 2011, incorporated by reference herein in its entirety.

TABLE 8

Broth viscosity of Morph 77B7 compared to Morph 77b7 Δgas1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δgas1 | gas1 | 115 | 500 | 39 | 147 |

B. Viscosity Reduction in Disrupted Crz1

In fungi, calcineurin mediated $Ca^{2+}$ signaling has been shown to be required for growth, development, and virulence in many organisms. It is necessary for adaption to diverse environmental conditions including high cation levels and alkaline pH. The gene crz1 encodes a calcineurin-regulated transcription factor. The Crz1p transcription factor is dephosphorylated when the phosphatase calcineurin is activated by $Ca^{2+}$/calmodulin. It then enters the nucleus and induces expression of a number of genes, many of which encode proteins with cell wall-related functions (Yoshimoto et al., 2002; Lagorce et al., 2003; Garcia et al., 2004; Karababa et al., 2006; Pardini et al., 2006, Munro, C. et al. 2009). Deletion of crz1 or a homolog can result in alterations in hyphal morphology (Kothe, G. and Free, S. 1998, Prokisch, H. et al. 1997).

A *Trichoderma reesei* Morph strain was prepared as described above. The *Trichoderma reesei* crz1 (PID 36391) was deleted from mutant Morph 77B7. Strain Morph TrGA 77B7 Δpyr2 was transformed with the crz1 disruption cassette using PEG-mediated transformation, and plated on Vogel's minimal medium containing sorbitol to select for candidates based on uridine prototrophy acquired by the pyr2 marker. As shown in Table 9, Morph 77B7 Δcrz1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δcrz1 did not require as much energy to achieve the same biomass concentration. Agitation rate never increased above 500 rpm and the % DO never dropped below 100. Details of the crz1 disruption can be found in U.S. Provisional Application No. 61/480,610, filed Apr. 29, 2011, incorporated by reference herein in its entirety.

TABLE 9

Broth viscosity of Morph 77B7 compared to Morph 77b7 Δcrz1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δcrz1 | crz1 | 100 | 500 | 39 | 120 |

C. Viscosity Reduction in Disrupted Tps1

The gene tps2 encodes a trehalose-phosphate phosphatase involved in the synthesis of the disaccharide trehalose. Trehalose is a stress induced sugar that buffers the refolding of denatured proteins in the cytoplasm and ER (Singer, M et al. 1998, Simola, M et al. 2000). This disaccharide is produced in large quantities by diverse organisms in response to a variety of stresses. In yeast, trehalose stabilizes proteins at high temperatures and assists in refolding heat damaged proteins (Simola, M et al. 2000).

A *Trichoderma reesei* Morph strain was prepared as described above. The *Trichoderma reesei* tps2 (PID 48707) was deleted from mutant Morph 77B7. Strain Morph TrGA 77B7 Δpyr2 was transformed with the tps2 disruption cassette using PEG-mediated transformation, and plated on Vogel's minimal medium containing sorbitol to select for candidates based on uridine prototrophy acquired by the pyr2 marker. As shown in Table 10, Morph 77B7 Δtps2 has a reduction in broth viscosity compared to the parent Morph 77B7. At the end of the batch growth phase, when all the glucose had been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δtps2 did not require as much energy to achieve the same biomass concentration. Agitation rate never increased above 500 rpm and the % DO never dropped below 110. Details of the tps1 disruption can be found in U.S. Provisional Application No. 61/480,629, filed Apr. 29, 2011, incorporated by reference herein in its entirety.

TABLE 10

Broth viscosity of Morph 77B7 compared to Morph 77b7 Δtps2

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δtps2 | tps2 | 110 | 500 | 41 | 94 |

Although the foregoing compositions and methods have been described in some detail by way of illustration and examples for purposes of clarity of understanding, it will be apparent to those skilled in the art that certain changes and modifications can be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

REFERENCES

The following references, and additional reference cited herein, are hereby incorporated by reference:

Caracuel, Z. et al. (2005) *Molecular Plant-Microbe Interactions* 18:1140-47.
Hajdukiewiez, P. et al. (1994) *Plant Molecular Biology* 25:989-94.
Hood, E. E. et al. (1993) *Trangenic Research* 2:208-18.
Hughes, H. and Stephens, D. J. (2008) *Cell Biol.* 129: 129-51.
Karhinen, L. et al. (2005) *Traffic* 6:562-74.
Mouyna, I. et al. (2005) *Molecular Microbiology* 56:1675-88.
Passolunghi, S. et al. (2010) *Microbial Cell Factories* 9:7-17.
Peng, R. et al. (2000) *J. Biol. Chem.* 275:11521-28.
Popolo, L et al. (2008) *J. Biol. Chem.* 283:18553-18565
Kruszewska et al. (1998) *Curr. Genet.* 33:445-450.
Zakrzewska et al. (2003) *Appl Environ Microbiol.* 69:4383-4389.
Roberg, K. J. et al. (1999) *J. Cell. Biol.* 145:659-72.
Shimoni, Y. et al. (2000) *J. Cell. Biol.* 151:973-84.
Schirawski, J. et al. (2005) *Plant Cell* 17: 3532-3543.
Turchini, A. et al. (2000) *J. Bacteriol.* 182:1167-71.
Yoshimoto et al. (2002) *J. Biol. Chem.* 227:31079-31088.
Lagorce et al. (2003) *J. Biol. Chem.* 278:20345-20357.
Garcia et al. (2004) *J. Bio. Chem.* 279:15183-15195.
Karababa et al. (2006) *Mol. Microbiol.* 59:1429-1451.
Pardini et al. (2006) *J. Biol. Chem.* 281:40399-40411.

Munro, C. et al. (2009) *Mol. Microbiol.* 63:1399-1413.
Kothe, G. and Free, S. (1998) *Fungal Genet. Biol* 23:248-258.

Prokisch, H., et al. (1997) *Gen. Genet.* 256:104-114.
Simola, M et al. (2000) *Mol. Microbiol.* 37:42-53.
Singer, M. and Lindquist S. (1998) *Mol. Cell.* 5:639-48.

---

What is claimed is:

1. A variant strain of *Trichoderma reesei* derived from a parental strain, the variant strain comprising a genetic alteration that causes cells of the variant strain to produce a reduced amount of functional mannose-1-phoshate guanyltransferase (Mpg1) protein compared to cells of the parental strain, wherein the genetic alteration comprises a disruption of the mpg1 gene present in the parental strain, wherein the cells of the variant strain produce, during aerobic fermentation in submerged culture, a cell broth that (i) requires a reduced amount of agitation to maintain a preselected dissolved oxygen content compared to the cells of the parental strain, and/or (ii) maintains an increased dissolved oxygen content at a preselected amount of agitation, compared to the cells of the parental strain.

2. The variant strain of claim 1, wherein disruption of the mpg1 gene is the result of deletion of all or part of the mpg1 gene.

3. The variant strain of claim 1, wherein disruption of the mpg1 gene is the result of deletion of a portion of genomic DNA comprising the mpg1 gene.

4. The variant strain of claim 1, wherein disruption of the mpg1 gene is the result of mutagenesis of the mpg1 gene.

5. The variant strain of claim 1, wherein disruption of the mpg1 gene is performed using site-specific recombination.

6. The variant strain of claim 1, wherein disruption of the mpg1 gene is performed in combination with introducing a selectable marker at the genetic locus of the mpg1 gene.

7. The variant strain of claim 1, wherein the variant strain does not produce functional Mpg1 protein.

8. The variant strain of claim 1, wherein the variant strain does not produce Mpg1 protein.

9. The variant strain of claim 1, wherein the variant strain further comprises a gene encoding a protein of interest.

10. The variant strain of claim 1, further comprising a disruption of the sfb3 gene.

11. The variant strain of claim 1, further comprising a disruption of at least one gene selected from the group consisting of the sfb3 gene, the seb1 gene, the gas1 gene, the crz1 gene, and the tps2 gene.

12. The variant strain of claim 1, wherein the variant strain produces substantially the same amount of, or more, total protein per unit amount of biomass as the parental strain.

13. A variant strain of *Trichoderma reesei* derived from a parental strain, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, wherein the genetic alteration comprises a disruption of the mpg1 gene present in the parental strain, and
(b) a gene encoding a protein of interest,
wherein the gene encoding the protein of interest is present in the variant strain prior to the genetic alteration in (a).

14. The variant strain of claim 13, wherein disruption of the mpg1 gene is performed in combination with introducing a selectable marker at the genetic locus of the mpg1 gene.

15. The variant strain of claim 13, wherein disruption of the mpg1 gene is performed in combination with disrupting at least one gene selected from the group consisting of the sfb3 gene, the seb1 gene, the gas1 gene, the crz1 gene, and the tps2 gene.

16. The variant strain of claim 13, wherein disruption of the mpg1 gene is performed in combination with disrupting the seb1 gene.

* * * * *